(12) United States Patent
Skalla et al.

(10) Patent No.: US 10,337,073 B2
(45) Date of Patent: Jul. 2, 2019

(54) MICRORNA POLYMORPHISMS CONFERRING ENHANCED DROUGHT TOLERANCE IN A PLANT

(71) Applicant: Syngenta Participations AG, Basel (CH)

(72) Inventors: Dale Wayne Skalla, Research Triangle Park, NC (US); Joseph Dallas Clarke, V, Research Triangle Park, NC (US); Ju-Kyung Yu, Slater, IA (US); Daolong Wang, Research Triangle Park, NC (US); Jianwei Lu, Research Triangle Park, NC (US)

(73) Assignee: Syngenta Participations AG, Basel (CH)

( * ) Notice: Subject to any disclaimer, the term of this patent is extended or adjusted under 35 U.S.C. 154(b) by 74 days.

(21) Appl. No.: 15/477,147

(22) Filed: Apr. 3, 2017

(65) Prior Publication Data

US 2017/0204476 A1    Jul. 20, 2017

Related U.S. Application Data

(62) Division of application No. 15/242,767, filed on Aug. 22, 2016, now Pat. No. 9,644,243, which is a division of application No. 15/057,516, filed on Mar. 1, 2016, now abandoned, which is a division of application No. 13/160,506, filed on Jun. 14, 2011, now Pat. No. 9,309,526.

(60) Provisional application No. 61/354,594, filed on Jun. 14, 2010.

(51) Int. Cl.
*A01H 1/04*    (2006.01)
*C12Q 1/6895*    (2018.01)
*C12N 15/82*    (2006.01)
*A01H 5/02*    (2018.01)

(52) U.S. Cl.
CPC ............ *C12Q 1/6895* (2013.01); *A01H 1/04* (2013.01); *A01H 5/02* (2013.01); *C12N 15/8218* (2013.01); *C12Q 2600/13* (2013.01); *C12Q 2600/156* (2013.01); *C12Q 2600/178* (2013.01)

(58) Field of Classification Search
None
See application file for complete search history.

(56) References Cited

PUBLICATIONS

Ehrenreich et al., MicroRNAs in plants: Possible contributions to phenotypic diversity. Plant Signal Behav., Oct. 2008, 3(10):829-830.
Collard et al., Euphytica, 2005, 142: pp. 169-196.
Zhang et al., "A genome-wide characterization of MicroRNA genes in maize," PLOS Genetics, Nov. 2009; 5(11):1-16.
Ehrenreich, I.M. and Purugganan, M.D., Sequence variation of MicroRNAs and their binding sites in *Arabidopsis*, Plant Physiology, Apr. 2008, vol. 146, p. 1974-1982.
GenBank entry BZ969809, PUGHP42TB ZM_0.6_1.0_KB *Zea mays* genomic clone ZMMBTa386G12, genomic survey sequence, Mar. 25, 2003[online], Retrieved on Aug. 11, 2011. Retrieved on the internet:URL:http//www.ncbi.nim.nih.gov/nucgss/BZ969809.
Chuck et al., Big impacts by small RNAs in plant development. Curr Opin Plant Biol., Feb. 2009 (published online Nov. 6, 2008), 12(1):81-86.

*Primary Examiner* — Brent T Page
(74) *Attorney, Agent, or Firm* — R. Kody Jones

(57) ABSTRACT

Methods of identifying a single nucleotide polymorphism associated with a plant trait and methods of identifying a plant having an improved trait. The plant trait is correlated with at least one single nucleotide polymorphism in a microRNA region of a plant genome. Isolated nucleic acids, transgenic plants, and methods of producing the same are also disclosed.

12 Claims, 46 Drawing Sheets
Specification includes a Sequence Listing.

FIG. 1A
miR169g Alignment

```
ID7002./1775      --------------------------------------------------|
AA3941./1769      --------------------------------------------------|
AF4031./1743      --------------------------------------------------|
AX5707./1782      --------------------------------------------------|
BB3004./1775      --------------------------------------------------|
CC8032./1763      --------------------------------------------------|
CE8415./1747      --------------------------------------------------|
FSNU505./1735     --------------------------------------------------|
HT7049HL./1754    --------------------------------------------------|
ID2618./1738      --------------------------------------------------|
ID5829./1759      --------------------------------------------------|
IJ6208./1719      --------------------------------------------------|
IQ1332./1775      --------------------------------------------------|
WR0588./1759      --------------------------------------------------|
XF7110./1788      --------------------------------------------------|
XO5744./1759      --------------------------------------------------|
XPFF003./1771     --------------------------------------------------|
XPCC003./1731     --------------------------------------------------|
PJ7065./1732      --------------------------------------------------|
FF6096./1784      --------------------------------------------------|
CC7752./1770      --------------------------------------------------|
pre_miRNA./1141   --------------------------------------------------|
mature_miRNA./123 --------------------------------------------------|
PUGHP42.R         tatgcatgaggtcaaactcaatttgagggaacaaaaacgactttaaatagtggcgcgt
```

FIG. 1B

```
ID7002./1775      --------------------------------------------------AcGaAtTCC--TTC
AA3941./1769      --------------------------------------------------AcGaAtTCC--TTC
AF4031./1743      -------------------------------------------------------------TTC
AX5707./1782      --------------------------------------------------AcGaAtTCC--TTC
BB3004./1775      ---------------------------------------CAGGGCAGGGAGTCC--TTC
CC8032./1763      --------------------------------------------------AcGaAtTCC--TTC
CE8415./1747      ------------------------------------------------------AtTCC--TTC
FSNU505./1735     ----------------------------------------------------------------
HT7049HL./1754    --------------------------CCAGAGCAGrGsAGrGAGTCCyTTC
ID2618./1738      ----------------------------------------------------------------
ID5829./1759      ----------------------------------------------------C--TTC
IJ6208./1719      ----------------------------------------------------------------
IQ1332./1775      ---------------------------------------AGGGCAGGGAGTCC--TTC
WR0588./1759      --------------------------------------------------AcGaAtTCC--TTC
XF7110./1788      ---------------------------------GAGCAGGGmAGGGAGTCC--TTC
XO5744./1759      --------------------------------------------------AcGaAtTCC--TTC
XPFF003./1771     ---------------------------------------AGCAGGGCAGGGAGTCC--TTC
XPCC003./1731     ----------------------------------------------------------------
PJ7065./1732      ----------------------------------------------------------------
FF6096./1784      ---------------------------------GAGCAGGGCAGGGAGTCC--TTC
CC7752./1770      ---------------------------------AGAGCAGGGCAGGGAGTCC--TTC
pre_miRNA./1141   ----------------------------------------------------------------
mature_miRNA./123 ----------------------------------------------------------------
PUGHP42.R         gacgctgactcctcgcagaagaatcgtcagcgacccCAGAGCAGGGCAGGGAGTCC--TTC
```

FIG. 1C

```
ID7002./1775       CTCCCACCAGCTAGCTAGCGATACTACTACTATCCAAAGAGAATATGGAGAGAGATTTCCCTGAG
AA3941./1769       CTCCCACCAGCTAGCTAGCGATACTACTACTATCCAAAGAGAATATGGAGAGAGATTTCCCTGAG
AF4031./1743       ------CACCAGCTAGCTAGCGATACTACTACTATCCAAAGAGAATATGGAGAGAGATTTCCCTGAG
AX5707./1782       CTCCCACCAGCTAGCTAGCGATACTACTACTATCCAAAGAGAATATGGAGAGAGATTTCCCTGAG
BB3004./1775       CTCCCACC----AGCTAGCGATACTACTACTATCCAAAGAGAATATGGAGAGAGATTTCCCTGAG
CC8032./1763       CTCCCmCCAGCTAGCTAGCGATACTACTACTATCCAAAGAGAATATGGAGAGAGATTTCCCTGAG
CE8415./1747       CTCCCACCAGCTAGCTAGCGATACTACTACTATCCAAAGAGAATATGGAGAGAGATTTCCCTGAG
FSNU505./1735      --------GCTAGCTAGCGATACTACTACTATCCAAAGAGAATATGGAGAGAGATTTCCCTGAG
HT7049HL./1754     CyCCCACCAGCTAGCTAGCGATACTACTACTATCCAAAGAGAATATGGAGAGAGATTTCCCTGAG
ID2618./1738       ---CCCACCAGCTAGCTAGCGATACTACTACTATCCAAAGAGAATATGGAGAGAGATTTCCCTGAG
ID5829./1759       CTCCCACCAGCTAGCTAGCGATACTACTACTATCCAAAGAGAATATGGAGAGAGATTTCCCTGAG
IJ6208./1719       ----------TAGCTAGCGATACTACTACTATCCAAAGAGAATATGGAGAGAGATTTCCCTGAG
IQ1332./1775       CTtCCtCCcaCcAGCTAGCGATACTACTACTATCCAAAGAGAATATGGAGAGAGATTTCCCTGAG
WR0588./1759       CTCCCACCAGCTAGCTAGCGATACTACTACTATCCAAAGAGAATATGGAGAGAGATTTCCCTGAG
XF7110./1788       CTCCCACCAGCTAGCTAGCGATACTACTACTATCCAAAGAGAATATGGAGAGAGATTTCCCTGAG
XO5744./1759       CTCCCACCAGCTAGCTAGCGATACTACTACTATCCAAAGAGAATATGGAGAGAGATTTCCCTGAG
XPFF003./1771      CTCCCACCAGCTAGCTAGCGATACTACTACTATCCAAAGAGAATATGGAGAGAGATTTCCCTGAG
XPCC003./1731      -----ACCAGCTAGCTAGCGATACTACTACTATCCAAAGAGAATATGGAGAGAGATTTCCCTGAG
PJ7065./1732       ------CCAGCTAGCTAGCGATACTACTACTATCCAAAGAGAATATGGAGAGAGATTTCCCTGAG
FF6096./1784       CTCCCACCAGCTAGCTAGCGATACTACTACTATCCAAAGAGAATATGGAGAGAGATTTCCCTGAG
CC7752./1770       CTCCCACCAGCTAGCTAGCGATACTACTACTATCCAAAGAGAATATGGAGAGAGATTTCCCTGAG
pre_miRNA./1141    ----------------------------------------------------------------
mature_miRNA./123  ----------------------------------------------------------------
PUGHP42.R          CTCCCACCAGCTAGCTAGCGATACTACTACTATCCAAAGAGAATATGGAGAGAGATTTCCCTGAG
```

FIG. 1D

```
ID7002./1775      ATTGCGCGAATCAGTCACT-------GCACGTACGTGTGGAGCTTTTCTGTTTTCTCATAAA
AA3941./1769      ATTGCGCGAATCAGTCACTCACTGCACTGCACGTACGTGTGGAGCTTTTCTGTTTTCTCATAAA
AF4031./1743      ATTGCGCGAATCAGTCACTCACTGCACTGCACGTACGTGTGGAGCTTTTCTGTTTTCTCATAAA
AX5707./1782      ATTGCGCGAATCAGTCACTCACTGCACTGCACGTACGTGTGGAGCTTTTCTGTTTTCTCATAAA
BB3004./1775      ATTGCGCGAATCAGTCACT-------GCACGTACGTGTGGAGCTTTTCTGTTTTCTCATAAA
CC8032./1763      ATTGCsCsAATCAGTCACTGCACTGCACGTACsTGTGGAGCTTTTCTGTTTTCTCATAAA
CE8415./1747      ATTGCsCGAATCAGTCACTCACTGCACTGCACGTACGTGTGGAGCTTTTCTGTTTTCTCATAAA
FSNU505./1735     ATTGCGCGAATCAGTCACT-------GCACGTACGTGTGGAGCTTTTCTGTTTTCTCATAAA
HT7049HL./1754    ATTGCGCGAATCAGTCACT-------GCACGTACGTGTGGAGCTTTTCTGTTTTCTCATAAA
ID2618./1738      ATTGCGCGAATCAGTCACTCACTGCACTGCACGTACGTGTGGAGCTTTTCTGTTTTCTCATAAA
ID5829./1759      ATTGCGCGAATCAGTCACT-------GCACGTACGTGTGGAGCTTTTCTGTTTTCTCATAAA
IJ6208./1719      ATTGCGCGAAwsAGTCACTGCmCTGCACGTGCACGTACGTGTGGAGCTTTTCTGTTTTCTCATAAA
IQ1332./1775      ATTGCGCGAATCAGTCACT-------GCACGTACGTGTGGAGCTTTTCTGTTTTCTCATAAA
WR0588./1759      ATTGCGCGAATCAGTCACTCACTGCACTGCACGTACGTGTGGAGCCTTTCTGTTTTCTCATAAA
XF7110./1788      ATTGCGCGAATCAGTCACTCACTGCACTGCACGTACGTGTGGAGCTTTTCTGTTTTCTCATAAA
XO5744./1759      ATTGCGCGAATCAGTCACT-------GCACGTACGTGTGGAGCTTTTCTGTTTTCTCATAAA
XPFF003./1771     ATTGCGCGAATCAGTCACTCACTGCACTGCACGTACGTGTGGAGCTTTTCTGTTTTCTCATAAA
XPCC003./1731     ATTGCGCGAATCAGTCACT-------GCACGTACGTGTGGAGCTTTTCTGTTTTCTCATAAA
PJ7065./1732      ATTGCGCGAATCAGTCACT-------GCACGTACGTGTGGAGCTTTTCTGTTTTCTCATAAA
FF6096./1784      ATTGCGCGAATCAGTCACTCACTGCACTGCACGTACGTGTGGAGCTTTTCTGTTTTCTCATAAA
CC7752./1770      ATTGCGCGAATCAGTCACT-------GCACGTACGTGTGGAGCTTTTCTGTTTTCTCATAAA
pre_miRNA./1141   ---------------------------------------------------------------
mature_miRNA./123 ---------------------------------------------------------------
PUGHP42.R         ATTGCGCGAATCAGTCACT-------GCACGTACGTGTGGAGCTTTTCTGTTTTCTCATAAA
SM1480DQA1FM                                                          ACGTGTGGAGCCTTT
SM1480DQA2TT                                                          ACGTGTGGAGCTTTTC
```

FIG. 1E

```
ID7002./1775      CGGCAAATGCAGCAGCAGCAGGAGGC-TTTGGGTATTTTTTTATTTTCTCTCAACGATTGGTAAT
AA3941./1769      CGGCAAATGCAGCAGCAGCAGGAGGC-TTTGGGTATTTTTTATTTTCTCTCAACGATTGGTAAT
AF4031./1743      CGGCAAATGCAGCAGCAGCAGGAGGC-TTTGGGTATTTTTTATTTTCTCTCAACGATTGGTAAT
AX5707./1782      CGGCAAATGCmGCAGCAGCAGGAGGC-TTTGGGTATTTTTTATTTTCTCTCAACGATTGGTAAT
BB3004./1775      CGGCAAATGCAGCAGCAGCAGGAGGC-TTTGGGTATTTTTTATTTTCTCTCAACGATTGGTAAT
CC8032./1763      CsGCAAATGCAGCAGCAGCAGGAGGCTTTTGGGTATTTTTTATTTTCTCTCAACGATTGGTAAT
CE8415./1747      CGGCAAATGCmGCAGCAGCAGGAGGC-TTTGGGTATTTTTTATTTTCTCTCAACGATTGGTAAT
FSNU505./1735     CGrCAAATrCAGCAGCAGCAGGAGGC-TTTGGGTATTTTTTATTTTCTCTCAACGATTGGTAAT
HT7049HL./1754    CGGCAAATGCAGCAGCAGCAGGAGGC-TTTGGGTATTTTTTATTTTCTCTCAACGATTGGTAAT
ID2618./1738      mGGCAAATGCAGCAGCAGCAGGAGGC-TTTGGGTATTTTTTATTTTCTCTCAACGATTGGTAAT
ID5829./1759      CGGCAAATGCAGCAGCAGCAGGAGGC-TTTGGGTATTTTTTATTTTCTCTCAACGATTGGTAAT
IJ6208./1719      CGGCAAATGCAGCAGCAGCAGGAGGC-TTTGGGTATTTTTTATTTTCTCTCAACGATTGGTAAT
IQ1332./1775      CGGCAAATGCAGCAGCAGCCGGAGGC-TTTGGGTATTTTTTATTTTCTCTCAgCGATTGGTAAT
WR0588./1759      CGGCAAATGCAGCAGCAGCAGGAGGC-TTTGGGTATTTTTTATTTTCTCTCAACGATTGGTAAT
XF7110./1788      CGGCAAATGCAGCAGCAGCAGGAGGC-TTTGGGTATTTTTTATTTTCTCTCAACGATTGGTAAT
XO5744./1759      CGGCAAATGCAGCAGCAGCAGGAGGC-TTTGGGTATTTTTTATTTTCTCTCAACGATTGGTAAT
XPFF003./1771     CGGCAAATGCAGCAGCAGCAGGAGGC-TTTGGGTATTTTTTATTTTCTCTCAACGATTGGTAAT
XPCC003./1731     CGGCAAATGCAGCAGCAGCAGGAGGC-TTTGGGTATTTTTTATTTTCTCTCAACGATTGGTAAT
PJ7065./1732      CGGCAAATGCAGCAGCAGCAGGAGGC-TTTGGGTATTTTTTATTTTCTCTCAACGATTGGTAAT
FF6096./1784      CGGCAAATGCAGCAGCAGCAGGAGGC-TTTGGGTATTTTTTATTTTCTCTCAACGATTGGTAAT
CC7752./1770      CGGCAAATGCAGCAGCAGCAGGAGGC-TTTGGGTATTTTTTATTTTCTCTCAACGATTGGTAAT
pre_miRNA./1141   ----------------------------------------------------------------
mature_miRNA./123 ----------------------------------------------------------------
PUGHP42.R         CGGCAAATGCAGCAGCAGCAGGAGGC-TTTGGGTATTTTTTATTTTCTCTCAACGATTGGTAAT
SM1480BQA2TT                                                                  TTGGTAAT
SM1480BQA1FM                                                                      TAAT
```

FIG. 1F

| | |
|---|---|
| ID7002./1775 | CAGTATCCGGGAAAAGCTGTGTGGATGTGGTAGACCGACGTGCGTTGAGTCGGCATCGTCCGG |
| AA3941./1769 | CAGTATCCGGGAAAAGCTGTGTGGATGTGGTAGACCGACGTGCGTTGAGTCGGCATCGTCCGG |
| AF4031./1743 | CAGTATCCGGGAAAAGCTGTGTGGATGTGGTAGACCGACGTGCGTTGAGTCGGCATCGTCCGG |
| AX5707./1782 | CAGTATCCGGGAAAAGCTGTGTGGATGTGGTAGACCGACGTGCGTTGAGTCGGCATCGTCCGG |
| BB3004./1775 | CAGTATCCGGGAAAAGCTGTGTGGATGTGGTAGACCGACGTGCGTTGAGTCGGCATCGTCCGG |
| CC8032./1763 | CAGTATCCGGGAAAAGCTGTGTGGATGTGGTAGACCGACGTGCGTTGAGTCGGCATCGTCCGG |
| CE8415./1747 | CAGTATCCGGGAAAAGCTGTGTGGATGTGGTAGACCGACGTGCGTTGAGTCGGCATCGTCCGG |
| FSNU505./1735 | CAGTATCtGGGAAAAGCTGTGTGGATGTGGTAGACCGACGTGCGTTGAGTCGGCATCGTCCGG |
| HT7049HL./1754 | CAGTATCCGGGAAAAGCTGTGTGGATGTGGTAGACCGACGTGCGTTGAGTCGGCATCGTCCGG |
| ID2618./1738 | CAGTATCCGGGAAAAGCTGTGTGGATGTGGTAGACCGACGTGCGTTGAGTCGGCATCGTCCGG |
| ID5829./1759 | CAGTATCtGGGAAAAGCTGTGTGGATGTGGTAGACCGACGTGCGTTGAGTCGGCATCGTCCGG |
| IJ6208./1719 | CAGTATCCGGGAAAAGCTGTGTGGATGTGGTAGACCGACGTGCGTTGAGTCGGCATCGTCCGG |
| IQ1332./1775 | CAGTATCCGGGAAAAGCTGTGTGGATGTGGTAGACCGACGTGCGTTGAGTCGGCATCGTCCGG |
| WR0588./1759 | CAGTATCCGGGAAAAGCTGTGTGGATGTGGTAGACCGACGTGCGTTGAGTCGGCATCGTCCGG |
| XF7110./1788 | CAGTATCtGGGAAAAGCTGTGTGGATGTGGTAGACCGACGTGCGTTGAGTCGGCATCGTCCGG |
| XO5744./1759 | CAGTATCCGGGAAAAGCTGTGTGGATGTGGTAGACCGACGTGCGTTGAGTCGGCATCGTCCGG |
| XPFF003./1771 | CAGTATCtGGGAAAAGCTGTGTGGATGTGGTAGACCGACGTGCGTTGAGTCGGCATCGTCCGG |
| XPCC003./1731 | CAGTATCtGGGAAAAGCTGTGTGGATGTGGTAGACCGACGTGCGTTGAGTCGGCATCGTCCGG |
| PJ7065./1732 | CAGTATCtGGGAAAAGCTGTGTGGATGTGGTAGACCGACGTGCGTTGAGTCGGCATCGTCCGG |
| FF6096./1784 | CAGTATCtGGGAAAAGCTGTGTGGATGTGGTAGACCGACGTGCGTTGAGTCGGCATCGTCCGG |
| CC7752./1770 | CAGTATCtGGGAAAaGCTGTGTGGATGTGGTAGACCGACGTGCGTTGAGTCGGCATCGTCCGG |
| pre_miRNA./1141 | ------------------------------------------------------------- |
| mature_miRNA./123 | ------------------------------------------------------------- |
| PUGHP42.R | CAGTATCtGGGAAAAGCTGTGTGGATGTGGTAGACCGACGTGCGTTGAGTCGGCATCGTCCGG |
| SM1480BQA2TT | CAGTATCTGG |
| SM1480BQA1FM | CAGTATCCGGGAA |

FIG. 1G

```
ID7002./1775     TTCATCCTATGTATTCCCTTTCCTGCTATAAATACCGGCCGGGCCGAGGGTGTCGAAGCC
AA3941./1769     TTCATCCTATGTATTCCCTTTCCTGCTATAAATACCGGCCGGGCCGAGGGTGTCGAAGCC
AF4031./1743     TTCATCCTATGTATTCCCTTTCCTGCTATAAATACCGGCCGGGCCGAGGGTGTCGAAGCC
AX5707./1782     TTCATCCTATGTATTCCCTTTCCTGCTATAAATACCGGCCGGGCCGAGGGTGTCGAAGCC
BB3004./1775     TTCATCCTATGTATTCCCTTTCCTGCTATAAATACCGGCCGGGCCGAGGGTGTCGAAGCC
CC8032./1763     TTCATCCTATGTATTCCCTTTCCTGCTATAAATACCGGCCGGGCCGAGGGTGTCGAAGCC
CE8415./1747     TTCATCCTATGTATTCCCTTTCCTGCTATAAATACCGGCCGGGCCGAGGGTGTCGAAGCC
FSNU505./1735    TTCATCCTATGTATTCCCTTTCyTGCTATAAATACCGGCCGGGCCGAGGGTGTCGAAGCC
HT7049HL./1754   TTCATCCTATGTATTCCCTTTCCTGCTATAAATACCGGCCGGGCCGAGGGTGTCGAAGCC
ID2618./1738     TTCATCCTATGTATTCCCTTTCCTGCTATAAATACCGGCCGGGCCGAGGGTGTCGAAGCC
ID5829./1759     TTCATCCTATGTATTCCCTTTCCTGCTATAAATACCGGCCGGGCCGAGGGTGTCGAAGCC
IJ6208./1719     TTCATCCTATGTATTCCCTTTCCTGCTATAAATACCGGCCGGGCCGAGGGTGTCGAAGCC
IQ1332./1775     TTCATCCTATGTATTCCCTTTCCTGCTATAAATACCGGCCGGGCCGAGGGTGTCGAAGCC
WR0588./1759     TTCATCCTATGTATTCCCTTTCCTGCTATAAATACCGGCCGGGCCGAGGGTGTCGAAaCC
XF7110./1788     TTCATCCTATGTATTCCCTTTCCTGCTATAAATACCGGCCGGGCCGAGGGTGTCGAAGCC
XO5744./1759     TTCATCCTATGTATTCCCTTTCCTGCTATAAATACCGGCCGGGCCGAGGGTGTCGAAGCC
XPFF003./1771    TTCATCCTATGTATTCCCTTTCCTGCTATAAATACCGGCCGGGCCGAGGGTGTCGAAGCC
XPCC003./1731    TTCATCCTATGTATTCCCTTTCCTGCTATAAATACCGGCCGGGCCGAGGGTGTCGAAGCC
PJ7065./1732     TTCATCCTATGTATTCCCTTTCCTGCTATAAATACCGGCCGGGCCGAGGGTGTCGAAGCC
FF6096./1784     TTCATCCTATGTATTCCCTTTCCTGCTATAAATACCGGCCGGGCCGAGGGTGTCGAAGCC
CC7752./1770     TTCATCCTATGTATTCCCTTTCCTGCTATAAATACCGGCCGGGCCGAGGGTGTCGAAGCC
pre_miRNA./1141  ------------------------------------------------------------
mature_miRNA./123 -----------------------------------------------------------
PUGHP42.R        TTCATCCTATGTATTCCCTTTCCTGCTATAAATACCGGCCGGGCCGAGGGTGTCGAAGCC
```

FIG. 1H

```
ID7002./1775       GCAGATCAATGCATGGC----CGCCGGCGCCGGTAGGGATGGAGGAGGAGGAGGAAGAAG
AA3941../1769      GCAGATCAATGCATGGC----CGCCGGCGCCGGTAGGGATGGAGGAGGAGGAGGAAGAAG
AF4031./1743       GCAGATCAATGCATGGC----CGCCGGCGCCGGTAGGGATGGAGGAGGAGGAGGAAGAAG
AX5707./1782       GCAGATCAATGCATGGC----CGCCGGCGCCGGTAGGGATGGAGGAGGAGGAGGAAGAAG
BB3004./1775       GCAGATCA-----ATGGC----CGCCGGCGCCGGTAGGGAT----GGAGGAGGAGGAGGAAGAAG
CC8032./1763       GCAGATCAATGCATGGC----CGCCGGCGCCGGTAGGGATGGAGGAGGAGGAGGAAGAAG
CE8415./1747       GCAGATCAATGCATGGC----CGCCGGCGCCGGTAGGGATGGAGGAGGAGGAGGAAGAAG
FSNU505./1735      GCAGATCAATGCATGGCCGCGCGCCGGCGCCGGTAGGGATGGAGGAGGAGGAGGAAGAAG
HT7049HL./1754     GCAGATCAATGCATGGC----CGCCGGCGCCGGTAGGGATGGAGGAGGAGGAGGAAGAAG
ID2618./1738       GCAGATCAATGCATGGCCGCCGCCCGGCGCCGGTAGGGATGGAGGAGGAGGAGGAAGAAG
ID5829./1759       GCAGATCAATGCATGGC----CGCCGGCGCCGGTAGGGATGGAGGAGGAGGAGGAAGAAG
IJ6208./1719       GCAGATCAATGCATGGC----CGCCGGCGCCGGTAGGGATGGAGGAGGAGGAGGAAGAAG
IQ1332./1775       GCAGATCA-----ATGGC----CGCCGGCGCCGGTAGGGAT----GGAGGAGGaGAAGAAG
WR0588./1759       GCAGATCAATGCATGGC----CGCCGGCGCCGGTAGGGATGGAGGAGGGGGAGGAAGAAG
XF7110./1788       GCAGATCAATGCATGGCCGCCGCCCGGCGCCGGTAGGGATGGAGGAGGAGGAGGAAGAAG
XO5744./1759       GCAGATCAATGCATGGC----CGCCGGCGCCGGTAGGGATGGAGGAGGAGGAGGAAGAAG
XPFF003./1771      GCAGATCAATGCATGGC----CGCCGGCGCCGGTAGGGATGGAGGAGGAGGAGGAAGAAG
XPCC003./1731      GCAGATCAATGCATGGC----CGCCGGCGCCGGTAGGGATGGAGGAGGAGGAGGAAGAAG
PJ7065./1732       GCAGATCAATGCATGGC----CGCCGGCGCCGGTAGGGATGGAGGAGGAGGAGGAAGAAG
FF6096./1784       GCAGATCAATGCATGGC----CGCCGGCGCCGGTAGGGATGGAGGAGGAGGAGGAAGAAG
CC7752./1770       GCAGATCAATGCATGGC----CGCCGGCGCCGGTAGGGATGGAGGAGGAGGAGGAAGAAG
pre_miRNA./1141    ------------------------------------------------------------
mature_miRNA./123  ------------------------------------------------------------
PUGHP42.R          GCAGATCAATGCATGGCCGCCGCCCGGCGCCGGTAGGGAT----GGAGGAGGAAGAAG
```

FIG. 1I

```
ID7002./1775      AGGCGGCCTTGCATGAGGGCCAGAGCTAGCCTGCCTCTGGTAGCCAAGGATGACTTGCCT
AA3941./1769      AGGCGGCCTTGCATGAGGGCCAGAGCTAGCCTGCCTCTGGTAGCCAAGGATGACTTGCCT
AF4031./1743      AGGCGGCCTTGCATGAGGGCCAGAGCTAGCCTGCCTCTGGTAGCCAAGGATGACTTGCCT
AX5707./1782      AGGCGGCCTTGCATGAGGGCCAGAGCTAGCCTGCCTCTGGTAGCCAAGGATGACTTGCCT
BB3004./1775      AGGCGGCCTTGCATGAGGGCCAGAGCTAGCCTGCCTCTGGTAGCCAAGGATGACTTGCCT
CC8032./1763      AGGCGGCCTTGCATGAGGGCCAGAGCTAGCCTGCCTCTGGTAGCCAAGGATGACTTGCCT
CE8415./1747      AGGCGGCCTTGCATGAGGGCCAGAGCTAGCCTGCCTCTGGTAGCCAAGGATGACTTGCCT
FSNU505./1735     AGGCGGCCTTGCATGAGGGCCAGAGCTAGCCTGCCTCTGGTAGCCAAGGATGACTTGCCT
HT7049HL./1754    AGGCGGCCTTGCATGAGGGCCAGAGCTAGCCTGCCTCTGGTAGCCAAGGATGACTTGCCT
ID2618./1738      AGGCGGCCTTGCATGAGGGCCAGAGCTAGCCTGCCTCTGGTAGCCAAGGATGACTTGCCT
ID5829./1759      AGGCGGCCTTGCATGAGGGCCAGAGCTAGCCTGCCTCTGGTAGCCAAGGATGACTTGCCT
IJ6208./1719      AGGCGGCCTTGCATGAGGGCCAGAGCTAGCCTGCCTCTGGTAGCCAAGGATGACTTGCCT
IQ1332./1775      AGGCGGCCTTGCATGAGGGCCAGAGCTAGCCTGCCTCTGGTAGCCAAGGATGACTTGCCT
WR0588./1759      AGGCGGCCTTGCATGAGGGCCAGAGCTAGCCTGCCTCTGGTAGCCAAGGATGACTTGCCT
XF7110./1788      AGGCGGCCTTGCATGAGGGCCAGAGCTAGCCTGCCTCTGGTAGCCAAGGATGACTTGCCT
XO5744./1759      AGGCGGCCTTGCATGAGGGCCAGAGCTAGCCTGCCTCTGGTAGCCAAGGATGACTTGCCT
XPFF003./1771     AGGCGGCCTTGCATGAGGGCCAGAGCTAGCCTGCCTCTGGTAGCCAAGGATGACTTGCCT
XPCC003./1731     AGGCGGCCTTGCATGAGGGCCAGAGCTAGCCTGCCTCTGGTAGCCAAGGATGACTTGCCT
PJ7065./1732      AGGCGGCCTTGCATGAGGGCCAGAGCTAGCCTGCCTCTGGTAGCCAAGGATGACTTGCCT
FF6096./1784      AGGCGGCCTTGCATGAGGGCCAGAGCTAGCCTGCCTCTGGTAGCCAAGGATGACTTGCCT
CC7752./1770      AGGCGGCCTTGCATGAGGGCCAGAGCTAGCCTGCCTCTGGTAGCCAAGGATGACTTGCCT
pre_miRNA./1141   ---------------------------CAGAGCTAGCCTGCCTCTGGTAGCCAAGGATGACTTGCCT
mature_miRNA./123 ----------------------------------------------TAGCCAAGGATGACTTGCCT
PUGHP42.R         AGGCGGCCTTGCATGAGGGCCAGAGCTAGCCTGCCTCTGGTAGCCAAGGATGACTTGCCT
```

FIG. 1J

```
ID7002./1775     ACATGGTCTCGCTAGTTCCGGTTGTTGTTGCATGCATGCCACTATGCCAGTCCTGCTGGGTTT
AA3941./1769     ACATGGTCTCGCTAGTTCCGGTTGTTGTTGCATGCATGCCACTATGCCAGTCCTGCTGGGTTT
AF4031./1743     ACATGGTCTCGCTAGTTCCGGTTGTTGTTGCATGCATGatgCatgCCACTATGCCAGTCCTGCTGGGTTT
AX5707./1782     ACATGGTCTCGCTAGTTCCGGTTGTTGTTGCATGCATGatgCatgCCACTATGCCAGTCCTGCTGGGTTT
BB3004./1775     ACATGGTCTCGCTAGTTCCGGTTGTTGTTGCATGCATGatgCatgCCACTATGCCAGTCCTGCTGGGTTT
CC8032./1763     ACATGGTCTCGCTAGTTCCGGTTGTTGTTGCATGCATGatgCatgCCACTATGCCAGTCCTGCTGGGTTT
CE8415./1747     ACATGGTCTCGCTAGTTCCGGTTGTTGTTGCATGCATGatgCatgCCACTATGCCAGTCCTGCTGGGTTT
FSNU505./1735    ACATGGTCTCGCTAGTTCCGGTTGTTGTTGCATGCATGCCACTATGCCAGTCCTGCTGGGTTT
HT7049HL./1754   ACATGGTCTCGCTAGTTCCGGTTGTTGTTGCATGCATGatgCatgCCACTATGCCAGTCCTGCTGGGTTT
ID2618./1738     ACATGGTCTCGCTAGTTCCGGTTGTTGTTGCATGCATGCCACTATGCCAGTCCTGCTGGGTTT
ID5829./1759     ACATGGTCTCGCTAGTTCCGGTTGTTGTTGCATGCATGatgCCACTATGCCAGTCCTGCTGGGTTT
IJ6208./1719     ACATGGTCTCGCTAGTTCCGGTTGTTGTTGCATGCATGmyrCTAkGCCACTATGCCAGTCCTGCTGGGTTT
IQ1332./1775     ACATGGTCTCGCTAGTTCCGGTTGTTGTTGCATGCATGatgCatgCCACTATGCCAGTCCTGCTGGGTTT
WR0588./1759     ACATGGTCTCGCTAGTTCCGGTTGTTGTTGCATGCATGatgCatgCCACTATGCCAGTCCTGCTGGGTTT
XF7110./1788     ACATGGTCTCGCTAGTTCCGGTTGTTGTTGCATGCATGatgCatgCCACTATGCCAGTCCTGCTGGGTTT
XO5744./1759     ACATGGTCTCGCTAGTTCCGGTTGTTGTTGCATGCATGatgCatgCCACTATGCCAGTCCTGCTGGGTTT
XPFF003./1771    ACATGGTCTCGCTAGTTCCGGTTGTTGTTGCATGCATGCCACTATGCCAGTCCTGCTGGGTTT
XPCC003./1731    ACATGGTCTCGCTAGTTCCGGTTGTTGTTGCATGCATGCCACTATGCCAGTCCTGCTGGGTTT
PJ7065./1732     ACATGGTCTCGCTAGTTCCGGTTGTTGTTGCATGCATGCCACTATGCCAGTCCTGCTGGGTTT
FF6096./1784     ACATGGTCTCGCTAGTTCCGGTTGTTGTTGCATGCATGCCACTATGCCAGTCCTGCTGGGTTT
CC7752./1770     ACATGGTCTCGCTAGTTCCGGTTGTTGTTGCATGCATGCCACTATGCCAGTCCTGCTGGGTTT
pre_miRNA./1141  ACATGGTCTCGCTAGTTCCGGTTGTTGTTGCATGCATGCCACTATGCCAGTCCTGCTGGGTTT
mature_miRNA./123 AC------------------------------------------------------------
PUGHP42.R        ACATGGTCTCGCTAGTTCCGGTTGTTGTTGCATGCATGCCACTATGCCAGTCCTGCTGGGTTT
```

FIG. 1K

| | |
|---|---|
| ID7002./1775 | GTGGGCGGTCTCCTTGGCTAGCCTGAGTGGCTCTTGCCTGTCATGGAAGGCCTCTTCTTC |
| AA3941./1769 | GTGGGCGGTCTCCTTGGCTAGCCTGAGTGGCTCTTGCCTGTCATGGAAGGCCTCTTCTTC |
| AF4031./1743 | GTGGGCGGTCTCCTTGGCTAGCCTGAGTGGCTCTTGCCTGTCATGGAAGGCCTCTTCTTC |
| AX5707./1782 | GTGGGCGGTCTCCTTGGCTAGCCTGAGTGGCTCTTGCCTGTCATGGAAGGCCTCTTCTTC |
| BB3004./1775 | GTGGGCGGTCTCCTTGGCTAGCCTGAGTGGCTCTTGCCTGTCATGGAAGGCCTCTTCTTC |
| CC8032./1763 | GTGGGCGGTCTCCTTGGCTAGCCTGAGTGGCTCTTGCCTGTCATGGAAGGCCTCTTCTTC |
| CE8415./1747 | GTGGGCGGTCTCCTTGGCTAGCCTGAGTGGCTCTTGCCTGTCATGGAAGGCCTCTTCTTC |
| FSNU505./1735 | GTGGGCGGTCTCCTTGGCTAGCCTGAGTGGCTCTTGCCTGTCATGGAAGGCCTCTTCTTC |
| HT7049HL./1754 | GTGGGCGGTCTCCTTGGCTAGCCTGAGTGGCTCTTGCCTGTCATGGAAGGCCTCTTCTTC |
| ID2618./1738 | GTGGGCGGTCTCCTTGGCTAGCCTGAGTGGCTCTTGCCTGTCATGGAAGGCCTCTTCTTC |
| ID5829./1759 | GTGGGCGGTCTCCTTGGCTAGCCTGAGTGGCTCTTGCCTGTCATGGAAGGCCTCTTCTTC |
| IJ6208./1719 | GTGGGCGGTCTCCTTGGCTAGCCTGAGTGGCTCTTGCCTGTCATGGAAGGCCTCTTCTTC |
| IQ1332./1775 | GTGGGCGGTCTCCTTGGCTAGCCTGAGTGGCTCTTGCCTGTaTCATGGAAGGCCTCTTCTTC |
| WR0588./1759 | GTGGGCGGTCTCCTTGGCTAGCCTGAGTGGCTCTTGCCTGTCATGGAAGGCCTCTTCTTC |
| XF7110./1788 | GTGGGCGGTCTCCTTGGCTAGCCTGAGTGGCTCTTGCCTGTCATGGAAGGCCTCTTCTTC |
| XO5744./1759 | GTGGGCGGTCTCCTTGGCTAGCCTGAGTGGCTCTTGCCTGTCATGGAAGGCCTCTTCTTC |
| XPFF003./1771 | GTGGGCGGTCTCCTTGGCTAGCCTGAGTGGCTCTTGCCTGTCATGGAAGGCCTCTTCTTC |
| XPCC003./1731 | GTGGGCGGTCTCCTTGGCTAGCCTGAGTGGCTCTTGCCTGTCATGGAAGGCCTCTTCTTC |
| PJ7065./1732 | GTGGGCGGTCTCCTTGGCTAGCCTGAGTGGCTCTTGCCTGTCATGGAAGGCCTCTTCTTC |
| FF6096./1784 | GTGGGCGGTCTCCTTGGCTAGCCTGAGTGGCTCTTGCCTGTCATGGAAGGCCTCTTCTTC |
| CC7752./1770 | GTGGGCGGTCTCCTTGGCTAGCCTGAGTGGCTCTTGCCTG-------------------- |
| pre_miRNA./1141 | ------------------------------------------------------------ |
| mature_miRNA./12.3 | ------------------------------------------------------------ |
| PUGHP42.R | GTGGGCGGTCTCCTTGGCTAGCCTGAGTGGCTCTTGCCTGTCATGGAAGGCCTCTTCTTC |

FIG. 1L

```
ID7002./1775       TCTGCCACGTACTCTCGCCTAGCTAGTCGCCT--TATG-------GTACGTAC---CGTC
AA3941./1769       TCTGCCACGTACTCTCGCCTAGCTAGTCGCCT--TATG-------GTACGTAC---CGTC
AF4031./1743       TCTGCCACGTACaCTCGCCTAGCTAGTCGCCT--TATG-------GTACGTACCGTCGTC
AX5707./1782       TCTGCCACGTACaCTCGCCTAGCTAGTCGCCTTATATG-------GTACGTACCGTCGTC
BB3004./1775       TCTGCCACGTACaCTCGCC-cGCTAGTCGCCTTATATGgtacgacGTACGTACCGTCGTC
CC8032./1763       TCTGCCACGTACaCTCGCCTAGCTAGTCGCCTTATATG-------GTACGTACCGTCGTC
CE8415./1747       TCTGCCACGTACaCTCGCCTAGCTAGTCGCCTTATATG-------GTACGTACCGTCGTC
FSNU505./1735      TCTGCCACGTACTCTCGCCTAGCTAGTCGCCT--TATG-------GTACGTAC---CGTC
HT7049HL./1754     TCTGCCACGTACaCTCGCCTAGCTAGTCGCCTTATATG-------GTACGTACCGTCGTC
ID2618./1738       TCTGCCACGTACaCTCGCCTAGCTAGTCGCCTTATATG-------GTACGTACCGTCGTC
ID5829./1759       TCTGCCACGTACTCTCGCCTAGCTAGTCGCCT--TATG-------GTACGTAC---CGTC
IJ6208./1719       TCTGCCACGTACwCTCGCCTAGCTAGTCGCCT--TATn-------nnnnn------nnnn
IQ1332./1775       TCTGCCACGTACaCTCGCCTAaCTAGTCGCCT--TATG-------GTACGTAC---CGTC
WR0588./1759       TCTGCCACGTACaCTCGCCTAGCTAGTCGCCTTATATG-------GTACGTACCGTCGTC
XF7110./1788       TCTGCCACGTACTCTCGCCTAGCTAGTCGCCT--TATG-------GTACGTAC---CGTC
XO5744./1759       TCTGCCACGTACaCTCGCCTAGCTAGTCGCCTTATATG-------GTACGTACCGTCGTC
XPFF003./1771      TCTGCCACGTACTCTCGCCTAGCTAGTCGCCT--TATG-------GTACGTAC---CGTC
XPCC003./1731      TCTGCCACGTACTCTCGCCTAGCTAGTCGCCT--TATG-------GTACGTAC---CGTC
PJ7065./1732       TCTGCCACGTACTCTCGCCTAGCTAGTCGCCT--TATG-------GTACGTAC---CGTC
FF6096./1784       TCTGCCACGTACTCTCGCCTAGCTAGTCGCCT--TATG-------GTACGTAC---CGTC
CC7752./1770       TCTGCCACGTACTCTCGCCTAGCTAGTCGCCT--TATG-------GTACGTAC---CGTC
pre_miRNA./1141    ------------------------------------------------------------
mature_miRNA./123  ------------------------------------------------------------
PUGHP42.R          TCTGCCACGTACTCTCGCCTAGCTAGTCGCCT--TATG-------GTACGTAC---CGTC
```

FIG. 1M

```
ID7002./1775      TGCCTCAGTGGCTCTGGCCTGTGCTTCGTTGGGTTTGCCAGGTAAGTATGGCTGT--CGT
AA3941./1769      TGCCTCAGTGGCTCTGGCCTGTGCTGTGCTTCGTTGTTGGGTTTGCCAGGTAAGTATGGCTGT--CGT
AF4031./1743      TGCCTC--TGGC---GGCCTGTGCTGTGCTTCGTTGTTGGGTTTGCCAGGTATGTATGGCTGT--CGT
AX5707./1782      TGCCTC---TGGC---GGCCTGTGCTGTGCTTCGTTtGGTTTGCCAGGTATGTATGGCTGTTCaaT
BB3004./1775      TGCCTC-------TGGCCTGTGCTTCGTTTGGTTTGCCAGGTATGTATGGCTGTTCaaT
CC8032./1763      TGCCTC---TGGC---GGCCTGTGCTGTGCTTCGTTtGGTTTGCCAGGTATGTATGGCTGTTCaaT
CE8415./1747      TGCCTC---TGGC---GGCCTGTGCTGTGCTTCGTTTGGTTTGCCAGGTATGTATGGCTGTTCaaT
FSNU505./1735     TGCCTCAGTGGCTCTGGCCTGTGCTTCGTTTGGGTTTGCCAGGTAAGTATGGCTGT--CGT
HT7049HL./1754    TGCCTC--TGGC---GGCCTGTGCTGTGCTTCGTTtGGTTTGCCAGGTATGTATGGCTGTTCaaT
ID2618./1738      TGCCTC---TGGC---GGCCTGTGCTGTGCTTCGTTtGGTTTGCCAGGTATGTATGGCTGTTCaaT
ID5829./1759      TGCCTCAGTGGCTCTGGCCTGTGCTTCGTTTGGGTTTGCCAGGTAAGTATGGCTGT--CGT
IJ6208./1719      nnnnnnnnnnnnnnnnnnnnnnnnnnnnnnnnnnnnnnnnnnnnnnnnnnnnnnnnmrT
IQ1332./1775      TGgCTCAGTGGCTCTGGCCTGTGCTTCGTTTGGGTTTGCCAGGTAAGTATGGCTGTTCaaT
WR0588./1759      TGCCTC--TGGC---GGCCTGTGCTGTGCTTCGTTCGTTGTTGGGTTTGCCAGGTATGTATGGCTGT--CGT
XF7110./1788      TGCCTCAGTGGCTCTGGCCTGTGCTGTGCTTCGTTGTTGGGTTTGCCAGGTAAGTATGGCTGTTCaaT
XO5744./1759      TGCCTC---TGGC---GGCCTGTGCTGTGCTTCGTTtGGTTTGCCAGGTATGTATGGCTGTTCaaT
XPFF003./1771     TGCCTCAGTGGCTCTGGCCTGTGCTGTGCTTCGTTGTTGGGTTTGCCAGGTAAGTATGGCTGT--CGT
XPCC003./1731     TGCCTCAGTGGCTCTGGCCTGTGCTGTGCTTCGTTGTTGGGTTTGCCAGGTAAGTATGGCTGT--CGT
PJ7065./1732      TGCCTCAGTGGCTCTGGCCTGTGCTGTGCTTCGTTGTTGGGTTTGCCAGGTAAGTATGGCTGT--CGT
FF6096./1784      TGCCTCAGTGGCTCTGGCCTGTGCTGTGCTTCGTTGTTGGGTTTGCCAGGTAAGTATGGCTGT--CGT
CC7752./1770      TGCCTCAGTGGCTCTGGCCTGTGCTGTGCTTCGTTGTTGGGTTTGCCAGGTAAGTATGGCTGT--CGT
pre_miRNA./1141   ------------------------------------------------------------
mature_miRNA./123 ------------------------------------------------------------
PUGHP42.R         TGCCTCAGTGGCTCTGGCCTGTGCTGTGCTTCGTTGTTGGGTTTGCCAGGTAAGTATGGCTGT--CGT
SM1480AQA1FM-RC                                               AGGTATGTATGGCTGT
SM1480AQA2TT-RC                                               AGGTAAGTATGGCTGT
```

FIG. 1N

```
ID7002./1775     TCATTGCTGATTCATCAGCTGGCTCATATATATGTAATGCTGCATGCAACGCTAATATCG
AA3941./1769     TCATTGCTGATTCATCAGCTGGCTCATATATATGTAATGCTGCATGCAACGCTAATATCG
AF4031./1743     TCATTGgTGATTCATCAGCTGGCTCATATATATGTAATGCTGCATGCAACGCTAATATtG
AX5707./1782     TCATTGgTGATTCATCAGCTGGCTCATATATATGTAATGCTGCATGCAACGCTAATATtG
BB3004./1775     TCATTGgTGATTCATCAGCTGGCTCATATATATGTAATGCTGCATGCAACGCTAATATtG
CC8032./1763     TCATTGgTGATTCATCAGCTGGCTCATATATATGTAATGCkGCATGCAACGCTAATATtG
CE8415./1747     TCATTGgTGATTCATCAGCTGGCTCATATATATGTAATGCkGCATGCAACGCTAATATtG
FSNU505./1735    TCATTGCTGATTCATCAGCTGGCTCATATATATGTAATGCTGCATGCAACGCTAATATCG
HT7049HL./1754   TCATTGgTGATTCATCAGCTGGCTCATATATATGTAATGCTGCATGCAACGCTAATATCG
ID2618./1738     TCATTGgTGATTCATCAGCTGGCTCATATATATGTAATGCkGCATGCAACGCTAATATtG
ID5829./1759     TCATTGgTGATTCATCAGCTGGCTCATATATATGTAATGCTGCATGCAACGCTAATATCG
IJ6208./1719     TCATTGsTGATTCATCAGCkGGCTCATATATATGTAATGCTGCATGCAACGCTAATATyG
IQ1332./1775     TCATTGgTGATTCATCAGCTGGCTCATATATATGTAATGCTGCATGCAACGCTAATATtG
WR0588./1759     TCATTGgTGATTCATCAGCTGGCTCATATATATGTAATGCTGCATGCAACGCTAATATtG
XF7110./1788     TCATTGCTGATTCATCAGCTGGCTCATATATATGTAATGCTGCATGCAACGCTAATATCG
XO5744./1759     TCATTGCTGATTCATCAGCTGGCTCATATATATGTAATGCTGCATGCAACGCTAATATkG
XPFF003./1771    TCATTGCTGATTCATCAGCTGGCTCATATATATGTAATGCTGCATGCAACGCTAATATCG
XPCC003./1731    TCATTGCTGATTCATCAGCTGGCTCATATATATGTAATGCTGCATGCAACGCTAATATCG
PJ7065./1732     TCATTGCTGATTCATCAGCTGGCTCATATATATGTAATGCTGCATGCAACGCTAATATCG
FF6096./1784     TCATTGCTGATTCATCAGCTGGCTCATATATATGTAATGCTGCATGCAACGCTAATATCG
CC7752./1770     TCATTGCTGATTCATCAGCTGGCTCATATATATGTAATGCTGCATGCAACGCTAATATCG
pre_miRNA./1141  ------------------------------------------------------------
mature_miRNA./123 ------------------------------------------------------------
PUGHP42.R        TCATTGCTGATTCATCAGCTGGCTCATATATATGTAATGCTGCAACGCTAATATC-
```

FIG. 10

```
IJ7002./1775    TTTTCTTAATTATTTTGTTATTACCTGTGCGTGCTTGCAGATTGTTCTGAATTCTGAAAT
AA3941./1769    TTTTCTTAATTATTTTGTTATTACCTGTGCGTGCTTGCAGATTGTTCTGAATTCT-----
AF4031./1743    TTTTCTTAATTATTTTGTTATTACCTGTGCCgGCTTGCAGATT-----------------
AX5707./1782    TTTTCTTAATTATTTTGTTATTACCTGTGCCgGCTTGCrGATwGTTCTGAATTCTGAAAT
BB3004./1775    TTTTCTTAATTATTTTGTTATTACCTGTGCCgGCTTGCAGATTGTTCTGAATTCTGAAAT
CC8032./1763    TTTTCTTAATTATTTTGTTATTACCTGTGCCgGCTTGCAGATTGTT--------------
CE8415./1747    TTTTCTTAATTATTTTGTTATTACCTGTGCCgGC--------------------------
FSNU505./1735   TTTTCTTAATTATTTTGTTATTACCTGTGCGTGCTTGCAGATT-----------------
HT7049HL./1754  TTTTCTTAATTATTTTGTTATwACCTGTGC------------------------------
ID2618./1738    TTTTCTTAATTATTTTGTTATTACCTGTGCCgGCTT------------------------
ID5829./1759    TTTTCTTAATTATTTTGTTATTACCTGTGCGTGCTTGCAGATTGTTCTGAATTC------
IJ6208./1719    TTTTCTTAATTATTTTGTTATwACCTsT--------------------------------
IQ1332./1775    TTTTCTTAATTATTTTGTTATTACCTGTGCGTGCTTGCAGATTGTTCTGAATTCTGAAAT
WR0588./1759    TTTTCTTAATTATTTTGTTATTACCTGTGCCgGCTTGCAGATT-----------------
XF7110./1788    TTTTCTTAATTATTTTGTTATTACCTGTGCGTGCTTGCAGATTGTTCTGAATTCTGAAAT
XO5744./1759    TTTTCTTAATTATTTTGTTATTACCTGTGCCgGCTTGCAGATT-----------------
XPFF003./1771   TTTTCTTAATTATTTTGTTATTACCTGTGCGTGCTTGCAGATTGTTCTGA----------
XPCC003./1731   TTTTCTTAATTATTTTGTTATTACCTGTGCGTGCT-------------------------
PJ7065./1732    TTTTCTTAATTATTTTGTTATTACCTGTGCGTGCTTGCAGATTGTTCTG-----------
FF6096./1784    TTTTCTTAATTATTTTGTTATTACCTGTGCGTGCTTGCAGATTGTTCTGAATTCTGAAAT
CC7752./1770    TTTTCTTAATTATTTTGTTATTACCTGTGCGTGCTTGCAGATTGTTC-------------
pre_miRNA./1141 ------------------------------------------------------------
mature_miRNA./123 ----------------------------------------------------------
PUGHP42.R       ------------------------------------------------------------
```

FIG. 1P

```
ID7002./1775      GTATGGG
AA3941./1769      -------
AF4031./1743      -------
AX5707./1782      GTATGGG
BB3004./1775      GTATGGG
CC8032./1763      -------
CE8415./1747      -------
FSNU505./1735     -------
HT7049HL./1754    -------
ID2618./1738      -------
ID5829./1759      -------
IJ6208./1719      -------
IQ1332./1775      GTATGGG
WR0588./1759      -------
XF7110./1788      GTATGG-
XO5744./1759      -------
XPFF003./1771     -------
XPCC003./1731     -------
PJ7065./1732      GT-----
FF6096./1784      -------
CC7752./1770      -------
pre_miRNA./1141   -------
mature_miRNA./123 -------
PUGHP42.R
```

FIG. 2A
miR171a Alignment

```
IJ6208./1643          -AGTCGGCCGATGCTCGGCGCGTGCCTCGATTCTTTTCTCGAGGCTAGCTAGCTACCTACA
AO1008./1626          ----TCGGCCGATGCTCGGCGCGTGCCTGCCTCGATTCTTTTCTCGAGGCTAGCTAGCTACCTACA
chr4_240118217..240118861  CAGTCGGCCGATGCTCGGCGCGTGCCTGCCTCGATTCTTTTCTCGAGGCTAGCTAGCTACCTACA
BB3004./1644          CAGTCGGCCGATGCTCGGCGCGTGCCTCGATTCTTTTCTCGAGGCTAGCTAGCTACCTACA
CE8415./1573          --------------------------------------------TyTCGwGGCTAGCTAGCTACCTACA
DC4015./1587          ----------------------------------------------------AGCkAgCTACA
FF6096./2619          CAGTCGGCCGATGCTCGCGCGTGCCTCGATTCTTTTCTCGAGGCTAGCTAGCTACCTACA
PJ7065./1595          ---------------------GtCTCGATTCTTTTTCTCGAGGCTAGCTAG----CTACA
WR0588./1570          ------------------------------------------------------------
XF7110./1464          --------------------------TCGATTCTTTTyTCGAGGCTAGCTAG----CTACA
XO5744./1604          -----------GGGCGTGCCTCGATTCTTTTCTCGAGGCTAGCTAGCTrCCTACA
XPCC003./1613         ------------GCCTCkATTCTTTTCTCGAGGCTAGCTAGCTACCTACA
XPFF003./1622         ------------------------------------------------------------
zma-MIR171a           ------------------------------------------------------------
mature_miR171a        ------------------------------------------------------------
```

FIG. 2B

```
IJ6208./1643            GGTGACGCGCATGCA-TGCATATATAGTTGCATCTGCGTGTGTTAGATGAGCACTTGTAAAA
AO1008./1626            GGTGACGCGCATGCA-TGCATATATAGTTGCATCTGCGTGTGTTAGATGAGCACTTGTAAAA
chr4_240118217..240118861  GGTGACGCGCATGCA-TGCATATATAGTTGCATCTGCGTGTGTTAGATGAGCACTTGTAAAA
BB3004./1644            GGTGACGCGCATGCA-TGCATATATAGTTGCATCTGCGTGTGTTAGATGAsCACTTGTAAAA
CE8415./1573            GGTGACGyATGCA--TGCATATATAGTTGCATCTGCGTGTGTTAGATGAGCACTTGTAAAA
DC4015./1587            GGTGACGCGCAyaCA--wGCATATATAGTTGCATCTGCGTGTGTTAGATGAGCACTctTg----
FF6096./2619            GGTGACGCGCATGCA-TGCATATATAGTTGCATCTGCGTGTGTTAGATGAGCACTTGTAAAA
PJ7065./1595            GGTGACGCGCATaCAATGCATATATAGTTGCATCTGCGTGTGTTAGATGAGCACTctTgtA-
WR0588./1570            -GTGACGCGCATaCrATGCATATATAGTTGCATCTGCGTGTGTTAGATGAGCACTctTgtAA
XF7110./1464            ------------------------------------------------------------
XO5744./1604            GGTGACGCGCATaCAATGCATATATAGTTGCATCTGCGTGTGTTAGATGAGCACTctTgtA-
XPCC003./1613           GGTGACGCGCATGCA-TGCATATATAGTTGCATCTGCGTGTGTTAGATGAsCACTTGTAAAA
XPFF003./1622           GGTGACGCGCATGCA-TGCATATATAwGTTGCATCTGCGTGTGTTAGATGAGnnnnnnnnnn
zma-MIR171a             ------------------------------------------------------------
mature_miR171a          ------------------------------------------------------------
```

FIG. 2C

```
IJ6208./1643              GAGATCATGTGATG-AGGGGgGGGGGGGGGAGAGAG------AGAGAGAGAGGAG
AO1008./1626              GAGATCATGTGATG-AGGGGgGGGGGGGGGAGAGAG------AGAGAGAGAGGAG
chr4_24011821..240118861  GAGATCATGTGATGaGgGGGGGGGGGGGGGAGAGAG------AGAGAGAGAGGAG
BB3004./1644              GAGATC---------AtGtGAtGaGGGGGGGGGGGGGGrrnnnnnnnnGAGGAG
CE8415./1573              GAGATCATGTGATG-AGGGGgGGGGGGGGGrGAGAGAG------AGAGAGAGGAG
DC4015./1587              -----------taaaAGaGatcatGtGatGAGAG--------gGgGgGAGAGGAG
FF6096./2619              GAGATCATGTGATG-AGGGGgGGGGGrGAGAGAG------AGAGAGAGGAG
PJ7065./1595              ----------aaaGAGatcatGtGatGAGAGgG---------gGgG-GAGAGGAG
WR0588./1570              aAGA-------------GatcAtGtGatGaGaGGgGgGgG------AGAGgGAGAGGAG
XF7110./1464              ---------------GGGGGGAGAGAG------AGAGAGAGAGGAG
XO5744./1604              --------aaaGAGatcatGtGatGAGAGgG---------gGgGGAGAGGAG
XPCC003./1613             GAGATCATGTGATG-AGGGGnnnGGGGGGAGAGAG------AGAGAGAGGAG
XPFF003./1622             nnnnnnnnnnnnn--nnnnnnnnkGGGGGGGGAGAGAG------AGAGAGAGGAG
zma-MIR171a               ------------------------------------------------
mature_miR171a            ------------------------------------------------
```

FIG. 2D

```
IJ6208./1643              GAAGACGCGGCCCGGACTATTTAGCTATCCGTGTGTGTGATGAAGGGCAGTAGCAGTATATGT
AO1008./1626              GAAGACGCGGCCCGGACTATTTAGCTATCCGTGTGTGTGATGATGAAGGGCAGTAGCAGTATATGT
chr4_240118217..240118861 GAAGACGCGGCCCGGACTATTTAGCTATCCGTGTGTGTGATGATGAAGGGCAGTAGCAGTATATGT
BB3004./1644              GAAGACGCGGCCCGGACTATTTAGCTATCCGTGTGTGTGATGATGAAGGGCAGTAGCAGTATATGT
CE8415./1573              GAAGACGCGGCCCGGACTATTTAGCTATCCGTGTGTGTGATGAAGGGCAGTAGCAGTATATGT
DC4015./1587              GAAGACGCGGCCCGGACTATTTAGCTATCCGTGTGTGTGATGAAGGGCAGTAGCAGTATATGT
FF6096./2619              GAAGACGCGGCCCGGACTATTTAGCTATCCGTGTGTGTGATGAAGGGCAGTAGCAGTATATGT
PJ7065./1595              GAAGACGCGGCCCGGACTATTTAGCTATCCGTGTGTGTGATGATGAAGGGCAGTAGCAGTATATGT
WR0588./1570              GAAGACGtGGCCCGGACTATTTAGCTATCCGTGTGTGTGATGATGAAGGGCAGTAGCAGTATATGT
XF7110./1464              GAAGACGtGGCCCGGACTATTTAGCTATCCGTGTGTGTGATGATGAAGGGCAGTAGCAGTATATGT
XO5744./1604              GAAGACGCGGCCCGGACTATTTAGCTATCCGTGTGTGTGATGAAGGGCAGTAGCAGTATATGT
XPCC003./1613             GAAGACGtGGCCCGGACTATTTAGCTATCCGTGTGTGTGATGATGAAGGGCAGTAGCAGTATATGT
XPFF003./1622             GAAGACGCGGCCCGGACTATTTAGCTATCCGTGTGTGTGATGATGAAGGGCAGTAGCAGTATATGT
zma-MIR171a               -------------------------------------------------------------
mature_miR171a            -------------------------------------------------------------
```

FIG. 2E

```
IJ6208./1643           GCTGCTTTGATGAATTCCATGGTTGGATGGCATGGAGGGAGCGATATTGGCGAGGTTCAA
AO1008./1626           GCTGCTTTGATGAATTCCATGGTTGGATGGCATGGAGGGAGCGATATTGGCGAGGTTCAA
chr4_240118217..240118861  GCTGCTTTGATGAATTCCATGGTTGGATGGCATGGAGGGAGCGATATTGGCGAGGTTCAA
BB3004./1644           GCTGCTTTGATGAATTCCATGGTTGGATGGCATGGAGGGAGCGATATTGGCGAGGTTCAA
CE8415./1573           GCTGCTTTGATGAATTCCATGGTTGGATGGCATGGAGGGAGCGATATTGGCGAGGTTCAA
DC4015./1587           GCTGCTTTGATGAATTCCATGGTTGGATGGCATGGAGGGAGCGATATTGGCGAGGTTCAA
FF6096./2619           GCTGCTTTGATGAATTCCATGGTTGGATGGCATGGAGGGAGCGATATTGGCGAGGTTCAA
PJ7065./1595           GCTGCTTTGATGAATTCCATGGTTGGATGGCATGGAGGGAGCGATATTGGCGAGGTTCAA
WR0588./1570           GCTGCTTTGATGAATTCCATGGTTGGATGGCATGGAGGGAGCGATATTGGCGAGGTTCAA
XF7110./1464           GCTGCyTTGATGAATTCCATGGTTGGATGGCATGGAGGGAGCGATATTGGCGAGGTTCAA
XO5744./1604           GCTGCTTTGATGAATTCCATGGTTGGATGGCATGGAGGGAGCGATATTGGCGAGGTTCAA
XPCC003./1613          GCyGCTTTGATGAATTCCATGGTTGGATGGCATGGAGGGAGCGATATTGGCGAGGTTCAA
XPFF003./1622          GCTGCTTTGATGAATTCCATGGTTGGATGGCATGGAGGGAGCGATATTGGCGAGGTTCAA
zma-MIR171a            -----------------------------------------GATATTGGCGAGGTTCAA
mature_miR171a         ------------------------------------------------------------
```

FIG. 2F

```
IJ6208./1643          TCAGATGATGTATTTTTCTTATATATAAATTTGCATGCATGAAGGTGTGAATCCAGTGTC
AO1008./1626          TCAGATGATGTATTTTTCTTATATATAAATTTGCATGCATGAAGGTGTGAATCCAGTGTC
chr4_240118217..240118861  TCAGATGATGTATTTTTCTTATATATAAATTTGCATGCATGAAGGTGTGAATCCAGTGTC
BB3004./1644          TCAGATGATGTATTTTTCTTATATATAAATTTGCATGCATGAAGGTGTGAATCCAGTGTC
CE8415./1573          TCAGATGATGTATTTTTCTTATATATAAATTTGCATGCATGAAGGTGTGAATCCAGTGTC
DC4015./1587          TCAGATGATGTATTTTTCTTATATATAAATTTGCATGCATGAAGGTGTGAATCCAGTGTC
FF6096./2619          TCAGATGATGTATTTTTCTTATATATAAATTTGCATGCATGAAGGTGTGAATCCAGTGTC
PJ7065./1595          TCAGATGATGTATTTTTCTTATATATAAATTTGCATGCATGAAGGTGTGAATCCAGTGTC
WR0588./1570          TCAGATGATGTATTTTTCTTATATATAAATTTGCATGCATGAAGGTGTGAATCCAGTGTC
XF7110./1464          TCAGATGATGTATTTTTCTTATATATAAATTTGCATGCATGAAGGTGTGAATCCAGTGTC
XO5744./1604          TCAGATGATGTATTTTTCTTATATATAAATTTGCATGCATGAAGGTGTGAATCCAGTGTC
XPCC003./1613         TCAGATGATGTATTTTTCTTATATATAAATTTGCATGCATGAAGGTGTGAATCCAGTGTC
XPFF003./1622         TCAGATGATGTATTTTTCTTATATATAAATTTGCATGCATGAAGGTGTGAATCCAGTGTC
zma-MiR171a           TCAGATGATGTATTTTTCTTATATATAAATTTGCATGCATGAAGGTGTGAATCCAGTGTC
mature_miR171a        ------------------------------------------------------------
```

FIG. 2G

```
IJ6208./1643              TGATTGAGCCGCGCCAATATCACTTCCTTCCACCATAAGTTTACACACAGAGAGGATTGC
AO1008./1626              TGATTGAGCCGCGCCAATATCACTTCCTTCCACCATAAGTTTACACACAGAGAGGATTGC
chr4_240118217..240118861 TGATTGAGCCGCGCCAATATCACTTCCTTCCACCATAAGTTTACACACAGAGAGGATTGC
BB3004./1644              TGATTGAGCCGCGCCAATATCACTTCCTTCCACCATAAGTTTACACACAGAGAGGATTGC
CE8415./1573              TGATTGAGCCGCGCCAATATCACTTCCTTCCACCATAAGTTTACACACAGAGAGGATTGC
DC4015./1587              TGATTGAGCCGCGCCAATATCACTTCCTTCCACCATAAGTTTACACACAGAGAGGATTGC
FF6096./2619              TGATTGAGCCGCGCCAATATCACTTCCTTCCACCATAAGTTTACACACAGAGAGGATTGC
PJ7065./1595              TGATTGAGCCGCGCCAATATCACTTCCTTCCACCATAAGTTTACACACAGAGAGGATTGC
WR0588./1570              TGATTGAGCCGCGCCAATATCACTTyCTTCCTTCCACCATAAGTTTACACACAGAGAGGATTGC
XF7110./1464              TGATTGAGCCGCGCCAATATCACTTCCTTCCACCATAAGTTTACACACAGAGAGGATTGC
XO5744./1604              TGATTGAGCCGCGCCAATATCACTTCCTTCCACCATAAGTTTACACACAGAGAGGATTGC
XPCC003./1613             TGATTGAGCCGCGCCAATATCACTTCCTTCCACCATAAGTTTACACACAGAGAGGATTGC
XPFF003./1622             TGATTGAGCCGCGCCAATATCACTTCCTTCCACCATAAGTTTACACACAGAGAGGATTGC
zma-MiR171a               TGATTGAGCCGCGCCAATATC---------------------------------------
mature_miR171a            TGATTGAGCCGCGCCAATATC---------------------------------------
```

FIG. 2H

```
IJ6208./1643              AGCGAGCCGCGTCTACTTCCAAAGGTTAGACCACTCGTTATTCCCTCATTTCCAAAATTACA
AO1008./1626              AGCGAGCCGCGTCTACTTCCAAAGGTTAGACCACTCGTTATTCCCTCATTTCCAAAATTACA
chr4_240118217..240118861 AGCGAGCCGCGTCTACTTCCAAAGGTTAGACCACTCGTTATTCCCTCATTTCCAAAATTACA
BB3004./1644              AGCGAGCCGCGTCTACTTCCAAAGGTTAGACCACTCGTTATTCCCTCATTTCCAAAATTACA
CE8415./1573              AGCGAGCCGCGTCTACTTCCAAAGGTTAGACCACTCGTTATTCCCTCATTTCCAAAATTACA
DC4015./1587              AGCGAGCCGCGTCTACTTCCAAAGGTTAGACCACTCGTTATTCCCTCATTTCCAAAATTACA
FF6096./2619              AGCGAGCCGCGTCTACTTCCAAAGGTTAGACCACTCGTTATTCCCTCATTTCCAAAATTACA
PJ7065./1595              AGCGAGCCGCGTCTACTTCCAAAGGTTAGACCACTCGTTATTCCCTCATTTCCAAAATTACA
WR0588./1570              AGCGAGCCGCGTCTACTTCCAAAGGTTAGACCACTCGTTATTCCCTCATTTCCAAAATTACA
XF7110./1464              AGCGAGCCGCGTCTACTTCCAAAGGTTAGACCACTCGTTATTCCCTCATTTCCAAAATTACA
XO5744./1604              AGCGAGCCGCGTCTACTTCCAAAGGTTAGACCAgTCGTTATTCCCTCATTTCCAAAATTACA
XPCC003./1613             AGCGAGCCGCGTCTACTTCCAAAGGTTAGACCAgTCGTTATTCCCTCATTTCCAAAATTACA
XPFF003./1622             AGCGAGCCGCGTCTACTTCCAAAGGTTAGACCAgTCGTTATTCCCTCATTTCCAAAATTACA
zma-MIR171a               --------------------------------------------------------------
mature_miR171a            --------------------------------------------------------------
SM1479BQA1FM                                    AGGTTAGACCACTCGTT
SM1479BQA2TT                                   AAGGTTAGACCAGTCGTT
```

FIG. 2I

```
IJ6208./1643              CTTGTCTCTATTATACTCCCCTCTGTGCCATTATATAGTGTTCGTTTTTAGCTTTTCTTTGTCCAT
AO1008./1626              CTTGTCTCTATTATACTCCCCTCTGTGCCATTATATAGTGTTCGTTTTTAGCTTTTCTTTGTCCAT
chr4_240118217..240118861 CTTGTCTCTATTATACTCCCCTCTGTGCCATTATATAGTGTTCGTTTTTAGCTTTTCTTTGTCCAT
BB3004./1644              CTTGTCTCTATTATACTCCCCTCTGTGCCATTmTmGTGTTCGTTTTTAGCTTTTCTTTGTCCAT
CE8415./1573              CTTGTCTCTATTATACTCCCCTCTGTGCCAyTATwGTGTTCGTTTTTAGCTTTTCTTTGTCCAT
DC4015./1587              CTTGTCTCTATTATACTCCCCTCTGTGCCATCATAGTGTTCGTTTTTAGCTTTTCTTTGTCCAT
FF6096./2619              CTTGTCTCTATTATACTCCCCTCTGTGCCATTAyAsTGTTCGTTTTTAGCTTTTCTTTGTCCAT
PJ7065./1595              CTTGTCTCTATTATACTCCCCTCTGTGCCATCATAGTGTTCGTTTTTAGCTTTTCTTTGTCCAT
WR0588./1570              CTTGTCTCTATTATACTCCCCTCTGTGCCATTATATAGTGTTCGTTTTAGCTTTTCTTTGTtCAT
XF7110./1464              CTTGTCTCTATTATACTCCCCTCTGTGCCATTATAsTGTTCGTTTTAGCTTTTCTTTGTCCAT
XO5744./1604              CTTGTCTCTATTATACTCCCCTCTGTGCCATCATAGTGTTCGTTTTTAGCTTTTCTTTGTtCAT
XPCC003./1613             CTTGTCTCTATTATACTCCCCTCTGTGCCATTATmGTGTTCGTTTTAGCTTTTCTTTGTCCAT
XPFF003./1622             CTTGTCTCTATTATACTCCCCTCTGTGCCATTATATAGTGTTCGTTTTTAGCTTTTCTTTGTCCAT
zma-MIR171a               ----------------------------------------------------------------
mature_miR171a            ----------------------------------------------------------------
SM1479AQA1FM                                              CTGTGCCATCATAGTG
SM1479AQA2VC                                            CCTCTGTGCCATTATAG
```

FIG. 2J

```
IJ6208./1643              ATTAAAATAGATATCAATGA--------------ATATATATATATATAATAATATTTTTGGAGCAC
AO1008./1626              ATTAAAATAGATATCAATGA----------------ATATATATATATATAATAATATTTTTGGAGCAC
chr4_240118217..240118861 ATTAAAATAGATATCAATGA----------------ATATATATATATATAATAATATTTTTGGAGCAC
BB3004./1644              ATTAAAATAGATATCAATGA--------------ATATATATATATATATAATAATATTTTTGGAGCAC
CE8415./1573              ATTAAAATAGATATCAATGA----------------ATATATATATATATAATAATATTTTTGGAGCAC
DC4015./1587              ATTAAAATAGATATCArTGAatatatATATATATATATATATATATATAATAATATTTTTGGAGCAC
FF6096./2619              ATTAAAATAGATATCAATGA--------ATATATATATATATATATATATAATAATATTTTTGGAGCAC
PJ7065./1595              ATTAAAATAGATATCAATGA--------ATATATATATATATATATATATAATAATATTTTTGGAGCAC
WR0588./1570              ATTAAAATAGATATCwATGA--------ATATATATATATATATATATATAATAATATTTTTGGAGCAC
XF7110./1464              ATTAAAATAGATATCAATGA----------------ATATATATATATATAATAATATTTTTGGAGCAC
XO5744./1604              ATTAAAATAGATATCAATGA--------ATATATATATATATATATATATAATAATATTTTTGGAGCAC
XPCC003./1613             ATTAAAATAGATATCAATGA----------------ATATATATATATATAATAATATTTTTGGAGCAC
XPFF003./1622             ATTAAAATAGATATCAATGA----------------ATATATATATATATAATAATATTTTTGGAGCAC
zma-MIR171a               --------------------------------------------------------------------
mature_miR171a            --------------------------------------------------------------------
```

FIG. 2K

```
IJ6208./1643            TAGACTTCTAATGACTACACGAAGCCCTGACCCAACGGTGCCATCCGGTTCAGCCACATC
AO1008./1626            TAGACTTCTAATGACTACACGAAGCCCTGACCCAACGGTGCCATCCGGTTCAGCCACATC
chr4_240118217..240118861 TAGACTTCTAATGACTACACGAAGCCCTGACCCAACGGTGCCATCCGG------------
BB3004./1644            TAGACTTCTAATGACTACACGAAGCCCTGACCCAACGGTGCCATCCGGTTCAGCCACATC
CE8415./1573            TAGACTTCTAATGACTACACGAAGCCCTGACCCAACGGTGCCATCCGGTTCAGCCACATC
DC4015./1587            TAGACTTCTAATGACTACACGAAGCCCTGACCCAACGGTGCCATCCGGTTCAGCCACATC
FF6096./2619            TAGACTTCTAATGACTACACGAAGCCCTGACCCAAmG-----------------------
PJ7065./1595            TAGACTTCTAATGACTACACGAAGCCCTGACCCAACGGTGCCATCCGGTTCA--------
WR0588./1570            TAGACTTCTAATGACTACACGAAGCCCTGACCCAACGGTGCCATCCGGTTCAGCCA----
XF7110./1464            TAGACTTCTAATGACTACACGAAGCC----------------------------------
XO5744./1604            TAGACTTCTAATGACTACACGAAGCCCTGACCCAACGGTGCCATCCGGTTCAGCCACATC
XPCC003./1613           TAGACTTCTAATGACTACACGAAGCCCTGACCCAACGGTGCCATCCGG------------
XPFF003./1622           TAGACTTCTAATGACTACACGAAGCCCTGACCCAACGGTGCCATCCGGTTCAGCCACATC
zma-MIR171a             ------------------------------------------------------------
mature_miR171a          ------------------------------------------------------------
```

FIG. 2L

```
IJ6208./1643                              AGAT
AO1008./1626                              ----
chr4_240118217..240118861                 AGAT
BB3004./1644                              AGAT
CE8415./1573                              ----
DC4015./1587                              ArA-
FF6096./2619                              ----
PJ7065./1595                              ----
WR0588./1570                              ----
XF7110./1464                              ----
XO5744./1604                              AGAT
XPCC003./1613                             ----
XPFF003./1622                             AGAT
zma-MIR171a                               ----
mature_miR171a                            ----
```

FIG. 3A
miR393a Alignment

```
AO1008./1792      ------------------------------------TCCGTGTCCCCTTCGGCCCGGGATGGCCACGTGCACGTC
XF7110./1766      -----------------------TGGTGGGCCCTCCGTGTCCGTGTCCCTTCGGCCCGGGATGGCCACGTGCACGTC
FF6096./1757      -----------------------------CCGTGTCCGTGTCCCTTCGGCCCGGGATGGCCACGTGCACGTC
chr2_736214..736992  AGCATCTCCGTGGGTGGGCCCTCCGTGTCCGTGTCCCTTCGGCCCGGGATGGCCACGTGCACGTC
XO5744./1755      ---------------------------------TCsGTGTCCCTTCGGCCCGGGATGGCCACGTGCACGTC
ID5829./1612      --------------------------------------------------------------------------
FSNU505./1739     --------------------------------CCGTGTCCCTTCGGCCCGGGATGGCCACGTGCACGTC
HT7049HL./1566    ----------------------------------TTCGGCCCGGATGGCCCACGTGCACGTC
AX5707./1763      ----------------------------------TTCGGCCCGGGATGGCCACGTGCACGTC
CC7752./1698      --------------------------------CGTGTCCCCTTCGGCCCGGGATGGCCACGTGCACGTC
AF4031./1757      --------------------------------CGTGTCCCCTTCGGCCCGGGATGGCCACGTGCACGTC
PJ7065./1782      --------------------------------CsGTGTCCCCTTCGGCCCGGGATGGCCACGTGCACGTC
HH5982./1566      ---------------------------------TTCGGCCCGGGATGGCCACGTGCACGTC
CE8415./1733      ---------------GTGGTGGGCCCTCsGTGTCCCCTTCGGCCCGGGATGGCCACGTGCACGTC
IQ1332./1762      --------------------------------CGTGTCCCCTTCGGCCCGGGATGGCCACGTGCACGTC
ID2618./1625      --------------------------------------------------------------------------
XPFF003./1746     AGCATCTCCGTGGGTGGGCCCTCCGTGTCCCGTGTCCCCTTCGGCCCGGGATGGCCACGTGCACGTC
AA3941./1745      -------------------------TGTCCCCTTCGGCCCGGGATGGCCACGTGCACGTC
WR0588./1758      ---------------------------CCCCTTCGGCCCGGGATGGCCACGTGCACGTC
IJ6208./1765      ----------------------------CTTCGGCCCGGGATGGCCACGTGCACGTC
ID7002./1758      ----------------------mmTCCGTGTCCCCTTCGGCCCGGGATGGCCACGTGCACGTC
XPCC003./1670     -----------------------------------------------------------GTC
CC8032./1708      --------------------------------CCGTGTCCCCTTCGGCCCGGGATGGCCACGTGCACGTC
DC4015./1698      ---------------------------------TCCCTTCGGCCCGGGATGGCCACGTGCACGTC
BB3004./1415      ---------------------------------CCCTTCGGCCCGGGATGGCCACGTGCACGTC
mature_miRNA./123 --------------------------------------------------------------------------
pre_miRNA./1127   --------------------------------------------------------------------------
```

FIG. 3B

```
AO1008./1792       GAAAGCGTGAGAGCGA------------GAGGAGGACGCCTACCTAAGCGAGCAATGCAACAGCCA
XF7110./1766       GAAAGCGTGAGAGCGA------------GAGGAGGACGCCTACCTAAGCGAGCAATGCAACAGCCA
FF6096./1757       GAAAGCGTGAGAGCGA------------GAGGAGGACGCCTACCTAAGCGAGCAATGCAACAGCCA
chr2_736214..736992 GAAAGCGTGAGAGCGA------------GAGGAGGACGCCTACCTAAGCGAGCAATGCAACAGCCA
XO5744./1755       GAAAGCGTGAGAGCGA------------GAGGAGGACGgCTACCTAAGCGAGCAATGCAACAGCCA
ID5829./1612       ----------------------------------------------------------AGCCA
FSNU505./1739      GAAAGCGTGAGAGCGAGAGCGAGAGGAGGAGGAGGAGGACGCCTACCTAAGCGAGCAATGCAACAGCCA
HT7049HL./1566     GAAAGCGTGAGAGCGAGAGCGAGAGGAGGAGGAGGAGGAGGACGCCTACCTAAGCGAGCAATGCAACAGCCA
AX5707./1763       GAAAGCGTGAGAGCGA------------GAGGAGGACGCGCCTACCTAAGCGAGCAATGCAACAGCCA
CC7752./1698       GAAAGCGTGAGAGCGA------------GAGGAGGACGCCTACCTAAGCGAGCAATGCAACAGCCA
AF4031./1757       GAAAGCGTGAGAGCGA------------GAGGAGGACGCCTACCTAAGCGAGCAATGCAACAGCCA
PJ7065./1782       GAAAGCGTGAGAGCGAGAGCGAGAGGAGGAGGAGGAGGACGCCTACCTAAGCGAGCAATGCAACAGCCA
HH5982./1566       GAAAGCGTGAGAGCGA------------GAGGAGGACGCCTACCTAAGCGAGCAATGCAACAGCCA
CE8415./1733       GAAAGCGTGAGAGCGA------------GAGGAGGACGCCTACCTAAGCGAGCAATGCAACAGCCA
IQ1332./1762       GAAAGCGTGAGAGCGA------------GAGGAGGACGCCTACCTAAGCGAGCAATGCAACAGCCA
ID2618./1625       ----------------------------------------------------------AGCCA
XPFF003./1746      GAAAGCGTGAGAGCGA------------GAGGAGGACGCCTACCTAAGCGAGCAATGCAACAGCCA
AA3941./1745       GAAAGCGTGAGAGCGAGAGCGAGAGGAGGAGGAGGAGGAGCGCCTACCTAAGCGAGCAATGCAACAGCCA
WR0588./1758       GAAAGCGTGAGAGCGAGAGCGAGAGGAGGAGGAGGAGGAGCGCCTACCTAAGCGAGCAATGCAACAGCCA
IJ6208./1765       GAAAGCGTGAGAGCGA------------GAGGAGGACGCCTACCTAAGCGAGCAATGCAACAGCCA
ID7002./1758       GAAAGCGTGAGAGCGA------------GAGGAGGACGCCTACCTAAGCGAGCAATGCAACAGCCA
XPCC003./1670      GAAAGCGTGAGAGCGA------------GAGGAGGACGCCTACCTAAGCGAGCAATGCAACAGCCA
CC8032./1708       GAAAGCGTGAGAGCGA------------GAGGAGGACGCCTACCTAAGCGAGCAATGCAACAGCCA
DC4015./1698       GAAAGCGTGAGAGCGA------------GAGGAGGACGCCTACCTAAGCGAGCAATGCAACAGCCA
BB3004./1415       GAAAGCGTGAGAGCGA------------GAGGAGGACGCCTACCTAAGCGAGCAATGCAACAGCCA
mature_miRNA./123  ----------------------------------------------------------------
pre_miRNA./1127    ----------------------------------------------------------------
```

FIG. 3C

```
AO1008./1792        TCATCGTCATTCACCTTGCCTATCCATCATCCTCGTCTTCTTCTTCTTCTGTCTATCCATGGCGAT
XF7110./1766        TCATCGTCATTCACCTTGCCTATCCATCATCCTCGTCTTCTTCTTCTTCTGTCTATCCATGGCGAT
FF6096./1757        TCATCGTCATTCACCTTGCCTATCCATCATCCTCGTCTTCTTCTTCTTCTGTCTATCCATGGCGAT
chr2_736214..736992 TCATCGTCATTCACCTTGCCTATCCATCATCCTCGTCTTCTTCTTCTTCTGTCTATCCATGGCGAT
XO5744./1755        TCATCGTCATTCACCTTGCCTATCCATCATCCTCGTCTTCTTCTTCTTCTGTCTATCCATGGCGAT
ID5829./1612        TCATCG------------------------------TGTCTTCTTCTTCTTCTGTCTATCCATGGCGAT
FSNU505./1739       TCATCGTCATTCACCTTGCCTATCCATCATCGTCGTCTTCTTCTTCTTCTGTCTATCCATGGCGAT
HT7049HL./1566      TCATCGTCATTCACCTTGCCTATCCATCATCGTCGTCTTCTTCTTCTTCTGTCTATCCATGGCGAT
AX5707./1763        TCATCGTCATTCACCTTGCCTATCCATCATCCTCGTCTTCTTCTTCTTCTGTCTATCCATGGCGAT
CC7752./1698        TCATCGTCATTCACCTTGCCTATCCATCATCCTCGTCTTCTTCTTCTTCTGTCTATCCATGGCGAT
AF4031./1757        TCATCGTCATTCACCTTGCCTATCCATCATCGTCGTCTTCTTCTTCTTCTGTCTATCCATGGCGAT
PJ7065./1782        TCATCGTCATTCACCTTGCCTATCCATCATCGTCGTCTTCTTCTTCTTCTGTCTATCCATGGCGAT
HH5982./1566        TCATCGTCATTCACCTTGCCTATCCATCATCCTCGTCTTCTTCTTCTTCTGTCTATCCATGGCGAT
CE8415./1733        TCATCGTCATTCACCTTGCCTATCCATCATCCTCGTCTTCTTCTTCTTCTGTCTATCCATGGCGAT
IQ1332./1762        TCATCG------------------------------TCGTCTTCTTCTTCTTCTGTCTATCCATGGCGAT
ID2618./1625        TCATCG------------------------------TCGTCTTCTTCTTCTTCTGTCTATCCATGGCGAT
XPFF003./1746       TCATCGTCATTCACCTTGCCTATCCATCATCCTCGTCTTCTTCTTCTTCTGTCTATCCATGGCGAT
AA3941./1745        TCATCGTCATTCACCTTGCCTATCCATCATCGTCGTCTTCTTCTTCTTCTGTCTATCCATGGCGAT
WR0588./1758        TCATCGTCATTCACCTTGCCTATCCATCATCCTCGTCTTCTTCTTCTTCTGTCTATCCATGGCGAT
IJ6208./1765        TCATCGTCATTCACCTTGCCTATCCATCATCCTCGTCTTCTTCTTCTTCTGTCTATCCATGGCGAT
ID7002./1758        TCATCGTCATTCACCTTGCCTATCCATCATCCTCGTCTTCTTCTTCTTCTGTCTATCCATGGCGAT
XPCC003./1670       TCATCGTCATTCACCTTGCCTATCCATCATCCTCGTCTTCTTCTTCTTCTGTCTATCCATGGCGAT
CC8032./1708        TCATCGTCATTCACCTTGCCTATCCATCATCCTCGTCTTCTTCTTCTTCTGTCTATCCATGGCGAT
DC4015./1698        TCATCGTCATTCACCTTGCCTATCCATCATCCTCGTCTTCTTCTTCTTCTGTCTATCCATGGCGAT
BB3004./1415        TCATCGTCATTCACCTTGCCTATCCATCATCCTCGTCTTCTTCTTCTTCTGTCTATCCATGGCGAT
mature_miRNA./123   ------------------------------------------------------------------
pre_miRNA./1127     ------------------------------------------------------------------
SM1481AQA1FM                                                            CCATCATCCTCGTCT
SM1481AQA2TT                                                            CCATCATCGTCGTCT
```

FIG. 3D

```
AO1008./1792         TTGGCGTTATAACCACCCCC-ACCCCCACC------CTTCTCTGGCTACGTCCTCGCTTT
XF7110./1766         TTGGCGTTATAACCACCCCC-ACCCCCACC------CTTCTCTGGCTACGTCCTCGCTTT
FF6096./1757         TTGGCGTTATAACCACCCCC-ACCCCCACC------CTTCTCTGGCTACGTCCTCGCTTT
chr2_736214..736992  TTGGCGTTATAACCACCCCC-ACCCCCACC------CTTCTCTGGCTACGTCCTCGCTTT
XO5744./1755         TTGGCGTTATAACCACCCCC-ACCCCCACC------CTTCTCTGGCTACGTCCTCGCTTT
ID5829./1612         -TGGCGTTATAACCACCCCCCACCCCCACC------CTTCTCTGGCTACGTCCTCGCTTT
FSNU505./1739        TTGGCGTTATAACCACCCC----aCCCCCACC----CTTCCCTGGCTACGaCCTCGCTTT
HT7049HL./1566       TTGGCGTTATAACCACCCC----aCCCCCACC----CTTCcCTGGCTACGaCCTCGCTTT
AX5707./1763         TTGGCGTTATAACCACCCCC-ACCCCCACC------CTTCTCTGGCTACGTCCTCGCTTT
CC7752./1698         TTGGCGTTATAACCACCCCC-ACCCCCACC------CTTCTCTGGCTACGTCCTCGCTTT
AF4031./1757         TTGGCGTTATAACCACCCCC-ACCCCCACC------CTTCTCTGGCTACGTCCTCGCTTT
PJ7065./1782         TTGGCGTTATAACCACCCCC-ACCCCCACC------CTTgcCTGGCTACGaCCTCGCTTT
HH5982./1566         TTGGCGTTATAACCACCCC----aCCCCCACC----CTTCcCTGGCTACGaCCTCGCTTT
CE8415./1733         TTGGCGTTATAACCACCCCC-ACCCCCACC------CTTCTCTGGCTACGTCCTCGCTTT
IQ1332./1762         TTGGCGTTATAACCACCCCC-ACCCCCACC------CTTCTCTGGCTACGTCCTCGCTTT
ID2618./1625         gTGGCGTTATAACCACCCCC-ACCCCCACCcccacyCTTCTCTGGCTACGTCCTCGCTTT
XPFF003./1746        TTGGCGTTATAACCACCCCC-ACCCCCACC------CTTCTCTGGCTACGTCCTCGCTTT
AA3941./1745         TTGGCGTTATAACCACCCC----aCCCCCACC----CTTgCTGGCTACGaCCTCGCTTT
WR0588./1758         TTGGCGTTATAACCACCCCC-ACCCCCACC------CTTCTCTGGCTACGaCCTCGCTTT
IJ6208./1765         TTGGCGTTATAACCACCCC----aCCCCCACC----CTTCTCTGGCTACGTCCTCGCTTT
ID7002./1758         TTGGCGTTATAACCACCCCC-ACCCCCACC------CTTCTCTGGCTACGTCCTCGCTTT
XPCC003./1670        TTGGCGTTATAACCACCCCC-ACCCCCACC------CTTCTCTGGCTACGTCCTCGCTTT
CC8032./1708         TTGGCGTTATAACCACCCCC-ACCCCCACC------CTTCTCTGGCTACGTCCTCGCTTT
DC4015./1698         TTGGCGTTATAACCACCCCC-ACCCCCACC------CTTCTCTGGCTACGTCCTCGCTTT
BB3004./1415         TTGGCGTTATAACCACCCCC-ACCCCCACC------CTTCTCTGGCTACGTCCTCGCTTT
mature_miRNA./123    ------------------------------------------------------------
pre_miRNA./1127      ------------------------------------------------------------
SM1481BQA2TT                                                              TGGCTACGACCTCG
SM1481BQA1FM                                                              TGGCTACGTCCTCG
```

FIG. 3E

```
AO1008./1792      CCCTTCCTCCCAGCTGCCTGCCCCCC-T--CCCTACCCyAGCTACGCACGCTACCAGC
XF7110./1766      CCCTTCCTCCCAGCTGCCTGCCCCCCT-T--CCCTACCCTAGCTACGCACGCTACCAGC
FF6096./1757      CCCTTCCTCCCAGCTGCCTGCCCCCCT-T--CCCTACCCTAGCTACGCACGCTACCAGC
chr2_736214..736992  CCCTTCCTCCCAGCTGCCTGCCCCCCT-T--CCCTACCCTAGCTACGCACGCTACCAGC
XO5744./1755      CCCTTCCTCCCAGCTGCCTGCCCCCCT-T--CCCTACCCTAGCTACGCACGCTACCAGC
ID5829./1612      CCCTTCCTCCCAGCTGCCTGCCCCCCT-T--CCCTACCCTAGCTACGCACGCTACCAGC
FSNU505./1739     CCCTTCCTCCCAGCTGCCTGCCCCCCT-T--CCCTACCCTAGCTACGCACGCTACCAGC
HT7049HL./1566    CCCTTCCTCCCAGCTGCCTGCCCCCCccttCCCTACCCTAGCTACGCACGCTACCAGC
AX5707./1763      CCCTTCCTCCCAGCTGCCTGCCCCCCT-T--CCCTACCCTAGCTACGCACGCTACCAGC
CC7752./1698      CCCTTCCTCCCAGCTGCCTGCCCCCCT-T--CCCTACCCTAGCTACGCACGCTACCAGC
AF4031./1757      CCCTTCCTCCCAGCTGCCTGCCCCCCT-T--CCCTACCCTAGCTACGCACGCTACCAGC
PJ7065./1782      CCCTTCCTCCCAGCTGCCTGCCCCCCCT-T--CCCTACCCTAGCTACGCACGCTACCAGC
HH5982./1566      CCCTTCCTCCCAGCTGCCTGCCCCCC-T--CCCTACCCTAGCTACGCACGCTACCAGC
CE8415./1733      CCCTTCCTCCCAGCTGCCTGCCCCCCT-T--CCCTACCCTAGCTACGCACGCTACCAGC
IQ1332./1762      CCCTTCCTCCCAGCTGCCTGCCCCCC-c--CCCTACCCwAGCTACGCACGCTACCAGC
ID2618./1625      CCCTTCCTCCCAGCTGCCTGCCCCCCT-T--CCCTACCCTAGCTACGCACGCTACCAGC
XPFF003./1746     CCCTTCCTCCCAGCTGCCTGCCCCCCT-T--CCCTACCCTAGCTACGCACGCTACCAGC
AA3941./1745      CCCTTCCTCCCAGCTGCCTGCCCCCCCctT--CCCTACCCTAGCTACGCACGCTACCAGC
WR0588./1758      CCCTTCCTCCCAGCTGCCTGCCCCCCCT-a--CCCTACCCTAGCTACGCACGCTACCAGC
IJ6208./1765      CCCTTCCTCCCAGCTGCCTGCCCCCCT-T--CCCTACCCTAGCTACGCACGCTACCAGC
ID7002./1758      CCCTTCCTCCCAGCTGCCTGCCCCCCT-T--CCCTACCCTAGCTACGCACGCTACCAGC
XPCC003./1670     CCCTTCCTCCCAGCTGCCTGCCCCCCT-T--CCCTACCCTAGCTACGCACGCTACCAGC
CC8032./1708      CCCTTCCTCCCAGCTGCCTGCCCCCCT-T--CCCTACCCTAGCTACGCACGCTACCAGC
DC4015./1698      CCCTTCCTCCCAGCTGCCTGCCCCCCT-T--CCCTACCCTAGCTACGCACGCTACCAGC
BB3004./1415      CCCTTCCTCCCAGCTGCCTGCCCCCCT-T--CCCTACCCTAGCTACGCACGCTACCAGC
mature_miRNA./123 ------------------------------------------------
pre_miRNA./1127   ------------------------------------------------
```

FIG. 3F

```
AO1008./1792      TGCCCCCCATCCATGCCGTCCAGGAAGCTGGTGGAGGACTCCAAAGGGATCGCAyTGATm
XF7110./1766      TGCCCCCCATCCATGCCGTCCAGGAAGCTGGTGGAGGACTCCAAAGGGATCGCATTGATC
FF6096./1757      TGCCCCCCATCCATGCCGTCCAGGAAGCTGGTGGAGGACTCCAAAGGGATCGCATTGATC
chr2_736214..736992  TGCCCCCCATCCATGCCGTCCAGGAAGCTGGTGGAGGACTCCAAAGGGATCGCATTGATC
XO5744./1755      TGCCCCCCATCCATGCCGTCCAGGAAGCTGGTGGAGGACTCCAAAGGGATCGCATTGATC
ID5829./1612      TGCCCCCCATCCATGCCGTCCAGGAAGCTGGTGGAGGACTCCAAAGGGATCGCATTGATC
FSNU505./1739     TGCCCCCCATCCATGCCGTCCAGGAAGCTGGTGGAGGACTCCAAAGGGATCGCATTGATC
HT7049HL./1566    TGCCCCCCATCCATGCCGTCCAGGAAGCTGGTGGAGGACTCCAAAGGGATCGCATTGATC
AX5707./1763      TGCCCCCCATCCATGCCGTCCAGGAAGCTGGTGGAGGACTCCAAAGGGATCGCATTGATC
CC7752./1698      TGCCCCCCATCCATGCCGTCCAGGAAGCTGGTGGAGGACTCCAAAGGGATCGCATTGATC
AF4031./1757      TGCCCCCCATCCATGCCGTCCAGGAAGCTGGTGGAGGACTCCAAAGGGATCGCATTGATC
PJ7065./1782      TGCCCCCCATCCATGCCGTCCAGGAAGCTGGTGGAGGACTCCAAAGGGATCGCATTGATC
HH5982./1566      TGCCCCCCATCCATGCCGTCCAGGAAGCTGGTGGAGGACTCCAAAGGGATCGCATTGATC
CE8415./1733      TGCCCCCCATCCATGCCGTCCAGGAAGCTGGTGGAGGACTCCAAAGGGATCGCATTGATC
IQ1332./1762      TGCCCCCCATCCATGCCGTCCAGGAAGCTGGTGGAGGACTCCAAAGGGATCGCATTGATC
ID2618./1625      TGCCCCCCATCCATGCCGTCCAGGAAGCTGGTGGAGGACTCCAAAGGGATCGCATTGATC
XPFF003./1746     TGCCCCCCATCCATGCCGTCCAGGAAGCTGGTGGAGGACTCCAAAGGGATCGCATTGATC
AA3941./1745      TGCCCCCCATCCATGCCGTCCAGGAAGCTGGTGGAGGACTCCAAAGGGATCGCATTGATC
WR0588./1758      TGCCCCCCATCCATGCCGTCCAGGAAGCTGGTGGAGGACTCCAAAGGGATCGCATTGATC
IJ6208./1765      TGCCCCCCATCCATGCCGTCCAGGAAGCTGGTGGAGGACTCCAAAGGGATCGCATTGATC
ID7002./1758      TGCCCCCCATCCATGCCGTCCAGGAAGCTGGTGGAGGACTCCAAAGGGATCGCATTGATC
XPCC003./1670     TGCCCCCCATCCATGCCGTCCAGGAAGCTGGTGGAGGACTCCAAAGGGATCGCATTGATC
CC8032./1708      TGCCCCCCATCCATGCCGTCCAGGAAGCTGGTGGAGGACTCCAAAGGGATCGCATTGATC
DC4015./1698      TGCCCCCCATCCATGCCGTCCAGGAAGCTGGTGGAGGACTCCAAAGGGATCGCATTGATC
BB3004./1415      TGCCCCCCATCCATGCCGTCCAGGAAGCTGGTGGAGGACTCCAAAGGGATCGCATTGATC
mature_miRNA./123 ------------------------------------TCCAAAGGGATCGCATTGATC
pre_miRNA./1127   -----------------CCAGGAAGCTGGTGGAGGACTCCAAAGGGATCGCATTGATC
```

FIG. 3G

```
AO1008./1792        TATTCTCACCTGCmGCCTGyTGCAyGCGATGCGAGTyGACGACAAGATCAGTGCAATCCC
XF7110./1766        TATTCTCACCTGCGCCTGCTGCATGCGATGCGAGTGGACGACAAGATCAGTGCAATCCC
FF6096./1757        TATTCTCACCTGCGCCTGCTGCATGCGATGCGAGTGGACGACAAGATCAGTGCAATCCC
chr2_736214..736992 TATTCTCACCTGCGCCTGCTGCATGCGATGCGAGTGGACGACAAGATCAGTGCAATCCC
XO5744./1755        TATTCTCACCTGCGCCTGCTGCATGCGATGCGAGTGGACGACAAGATCAGTGCAATCCC
ID5829./1612        TATTCTCACCTGCGCCTGCTGCATGCGATGCGAGTGGACGACAAGATCAGTGCAATCCC
FSNU505./1739       TATTCTCACCTGCGCCTGCTGCATGCGATGCGAGTGGACGACAAGATCAGTGCAATCCC
HT7049HL./1566      TATTCTCACCTGCGCCTGCTGCATGCGATGCGAGTGGACGACAAGATCAGTGCAATCCC
AX5707./1763        TATTCTCACCTGCGCCTGCTGCATGCGATGCGAGTGGACGACAAGATCAGTGCAATCCC
CC7752./1698        TATTCTCACCTGCGCCTGCTGCATGCGATGCGAGTGGACGACAAGATCAGTGCAATCCC
AF4031./1757        TATTCTCACCTGCGCCTGCTGCATGCGATGCGAGTGGACGACAAGATCAGTGCAATCCC
PJ7065./1782        TATTCTCACCTGCGCCTGCTGCATGCGATGCGAGTGGACGACAAGATCAGTGCAATCCC
HH5982./1566        TATTCTCACCTGCGCCTGCTGCATGCGATGCGAGTGGACGACAAGATCAGTGCAATCCC
CE8415./1733        TATTCTCACCTGCGCCTGCTGCATGCGATGCGAGTGGACGACAAGATCAGTGCAATCCC
IQ1332./1762        TATTCTCACCTGCGCCTGCTGCATGCGATGCGAGTGGACGACAAGATCAGTGCAATCCC
ID2618./1625        TATTCTCACCTGCGCCTGCTGCATGCGATGCGAGTGGACGACAAGATCAGTGCAATCCC
XPFF003./1746       TATTCTCACCTGCGCCTGCTGCATGCGATGCGAGTGGACGACAAGATCAGTGCAATCCC
AA3941./1745        TATTCTCACCTGCGCCTGCTGCATGCGATGCGAGTGGACGACAAGATCAGTGCAATCCC
WR0588./1758        TATTCTCACCTGCGCCTGCTGCATGCGATGCGAGTGGACGACAAGATCAGTGCAATCCC
IJ6208./1765        TATTCTCACCTGCGCCTGCTGCATGCGATGCGAGTGGACGACAAGATCAGTGCAATCCC
ID7002./1758        TATTCTCACCTGCGCCTGCTGCATGCGATGCGAGTGGACGACAAGATCAGTGCAATCCC
XPCC003./1670       TATTCTCACCTGCGCCTGCTGCATGCGATGCGAGTGGACGACAAGATCAGTGCAATCCC
CC8032./1708        TATTCTCACCTGCGCCTGCTGCATGCGATGCGAGTGGACGACAAGATCAGTGCAATCCC
DC4015./1698        TATTCTCACCTGCGCCTGCTGCATGCGATGCGAGTGGACGACAAGATCAGTGCAATCCC
BB3004./1415        TATTCTCACCTGCGCCTGCTGCATGCGATGCGAGTGGACGACAAGATCAGTGCAATCCC
mature_miRNA./123   T-----------------------------------------------------------
pre_miRNA./1127     TATTCTCACCTGCGCCTGCTGCATGCGATGCGAGTGGACGACAAGATCAGTGCAATCCC
```

FIG. 3H

```
AO1008./1792      TTTGGAATTTTCCACTCGCGCCTTCACCCCCGCCCCsC--cCCtCcatgCaCGCATAAAT
XF7110./1766      TTTGGAATTTTCCACTCGCGCCTTCACCCCCGCCCCGCCACGTGCCACACGCCCC-----T
FF6096./1757      TTTGGAATTTTCCACTCGCGCCTTCACCCCCGCCCCGCCACGTGCCACACGCCCC-----T
chr2_736214..736992  TTTGGAATTTTCCACTCGCGCCTTCACCCCCGCCCCGCCACGTGCCACACGCCCC-----T
XO5744./1755      TTTGGAATTTTCCACTCGCGCCTTCACCCCCGCCCCGCCACGTGCCACACGCCCC-----T
ID5829./1612      TTTGGAATTTTCCACTCGCGCCTTCACCCCCGCCCCGCCACGTGCCACACGCCCC-----T
FSNU505./1739     TTTGGAATTTTCCACTCGCGCCTTCACCCCCGCCCCGCCACGTGCCACACGCCCC-----T
HT7049HL./1566    TTTGGAATTTTCCACTCGCGCCTTCACCCCCGCCCCGCCACGTGCCACACGCCCC-----T
AX5707./1763      TTTGGAATTTTCCACTCGCGCCTTCACCCCCGCCCCGCCACGTGCCACACGCCCC-----T
CC7752./1698      TTTGGAATTTTCCACTCGCGCCTTCACCCCCGCCCCgC--cCCtCcatCCaCGCATAAAT
AF4031./1757      TTTGGAATTTTCCACTCGCGCCTTCACCCCCGCCCCGCCACGTGCCACACGCCCC-----T
PJ7065./1782      TTTGGAATTTTCCACTCGCGCCTTCACCCCCGCCCCGCCACGTGCCACACGCCCC-----T
HH5982./1566      TTTGGAATTTTCCACTCGCGCCTTCACCCCCGCCCCGCCACGTGCCACACGCCCC-----T
CE8415./1733      TTTGGAATTTTCCACTCGCGCCTTCACCCCCGCCCCGCCACGTGCCACACGCCCC-----T
IQ1332./1762      TTTGGAATTTTCCACTCGCGCCTTCACCCCCGCCCCGCCACGTGCCACACGCCCC-----T
ID2618./1625      TTTGGAATTTTCCACTCGCGCCTTCACCCCCGCCCCGCCACGTGCCACACGCCCC-----T
XPFF003./1746     TTTGGAATTTTCCACTCGCGCCTTCACCCCCGCCCCGCCACGTGCCACACGCCCC-----T
AA3941./1745      TTTGGAATTTTCCACTCGCGCCTTCACCCCCGCCCCGCCACGTGCCACACGCCCC-----T
WR0588./1758      TTTGGAATTTTCCACTCGCGCCTTCACCCCCGCCCCGCCACGTGCCACACGCCCC-----T
IJ6208./1765      TTTGGAATTTTCCACTCGCGCCTTCACCCCCGCCCCGCCACGTGCCACACGCCCC-----T
ID7002./1758      TTTGGAATTTTCCACTCGCGCCTTCACCCCCGCCCCGCCACGTGCCACACGCCCC-----T
XPCC003./1670     TTTGGAATTTTCCACTCGCGCCTTCACCCCCGCCCCgC----------------------
CC8032./1708      TTTGGAATTTTCCACTCGCGCCTTCACCCCCGCCCCgC----------------------
DC4015./1698      TTTGGAATTTTCCACTCGCGCCTTCACCCCCGCCCCgC----------------------
BB3004./1415      TTTGGAATTTTCCACTCGCGCCTTCACCCCCGCCCCgC----------------------
mature_miRNA./123 ------------------------------------------------------------
pre_miRNA./1127   TTTGGAATTTTCCACTCGCGCCTTC-----------------------------------
```

FIG. 3I

```
AO1008./1792        CCAaTTCCAA------gCtTTCCATGGATTCCATCTCTCATCAGtTA--TCTCTCTCTC
XF7110./1766        CCAT----------------CTTCCATGGATTCCATCTCTCATCAGGTA----TCTCTCTCTC
FF6096./1757        CCAT----------------CTTCCATGGATTCCATCTCTCATCAGGTA----TCTCTCTCTC
chr2_736214..736992 CCAT----------------CTTCCATGGATTCCATCTCTCATCAGGTA----TCTCTCTCTC
XO5744./1755        CCAT----------------CTTCCATGGATTCCATCTCTCATCAGGTA----TCTCTCTCTC
ID5829./1612        CCAT----------------CTTCCATGGATTCCATCTCTCATCAGGTA----TCTCTCTCTC
FSNU505./1739       CCAT----------------CTTCCATGGATTCCATCTCTCATCAGGTA----TCTCTCTCTC
HT7049HL./1566      CCAT----------------CTTCCATGGATTCCATCTCTCATCAGGTATCTCTCcCTaTa
AX5707./1763        CCAT----------------CTTCCATGGATTCCATCTCTCATCAGGTA----TCTCTCTCTC
CC7752./1698        CCAaTTCCAAatgcttCCTTCCATGGATTCCATCTCTCATCAGGTA----TCTCTCTCTC
AF4031./1757        CCAT----------------CTTCCATGGATTCCATCTCTCATCAGGTA----TCTCTCTCTC
PJ7065./1782        CCAT----------------CTTCCATGGATTCCATCTCTCATCAGGTATCTCTCcCTaTa
HH5982./1566        CCAT----------------CTTCCATGGATTCCATCTCTCATCAGGTA----TCTCTCTCTC
CE8415./1733        CCAT----------------CTTCCATGGATTCCATCTCTCATCAGGTA----TCTCTCTCTC
IQ1332./1762        CCAT----------------CTTCCATGGATTCCATCTCTCATCAGGTA----TCTCTCTCTC
ID2618./1625        CCAT----------------CTTCCATGGATTCCATCTCTCATCAGGTA----TCTCTCTCTC
XPFF003./1746       CCAT----------------CTTCCATGGATTCCATCTCTCATCAGGTA----TCTCTCTCTC
AA3941./1745        CCAT----------------CTTCCATGGATTCCATCTCTCATCAGGTATCTCTCcCTaTa
WR0588./1758        CCAT----------------CTTCCATGGATTCCATCTCTCATCAGGTA----TCTCTCTCTC
IJ6208./1765        CCAT----------------CTTCCATGGATTCCATCTCTCATCAGGTA----TCTCTCTCTC
ID7002./1758        CCAT----------------CTTCCATGGATTCCATCTCTCATCAGGTA----TCTCTCTCTC
XPCC003./1670       --------------------CATGGATTCCATCTCTCATCAGGTATCTCTCTCTCTCTCTC
CC8032./1708        --------------------CATGGATTCCATCTCTCATCAGGTATCTCTCTCTCTCTCTC
DC4015./1698        --------------------CATGGATTCCATCTCTCATCAGGTATCTCTCTCTCTCTCTC
BB3004./1415        ------------------------------------------------------------
mature_miRNA./123   ------------------------------------------------------------
pre_miRNA./1127     ------------------------------------------------------------
```

FIG. 3J

```
AO1008./1792         TATCTGCTCTTGCAAGCTACTTCCATGGATTTGATTTTTGTTAAGTTCGCCTACTTGCTC
XF7110./1766         TATCTGCTCTTGCAAGCTACTTCCATGGATTTGATTTTTGTTAAGTTCGCCTACTTGCTC
FF6096./1757         TATCTGCTCTTGCAAGCTACTTCCATGGATTTGATTTTTGTTAAGTTCGCCTACTTGCTC
chr2_736214..736992  TATCTGCTCTTGCAAGCTACTTCCATGGATTTGATTTTTGTTAAGTTCGCCTACTTGCTC
XO5744./1755         TATCTGCTCTTGCAAGCTACTTCCATGGATTTGATTTTTGTTAAGTTCGCCTACTTGCTC
ID5829./1612         TATCTGCTCTTGCAAGCTACTTCCATGGATTTGATTTTTGTTAAGTTCGCCTACTTGCTC
FSNU505./1739        TATCTGCTCTTGCAAGCTACTTCCATGGATTTGATTTTTGTTAAGTTCGCCTACTTGCTC
HT7049HL./1566       TATCTGCTCTTGCAAGCTACTTCCATGGATTTGATTTTTGTTAAGTTCGCCTACTTGCTC
AX5707./1763         TATCTGCTCTTGCAAGCTACTTCCATGGATTTGATTTTTGTTAAGTTCGCCTACTTGCTC
CC7752./1698         TATCTGCTCTTGCAAGCTACTTCCATGGATTTGATTTTTGTTAAGTTCGCCTACTTGCTC
AF4031./1757         TATCTGCTCTTGCAAGCTACTTCCATGGATTTGATTTTTGTTAAGTTCGCCTACTTGCTC
PJ7065./1782         TATCTGCTCTTGCAAGCTACTTCCATGGATTTGATTTTTGTTAAGTTCGCCTACTTGCTC
HH5982./1566         TATCTGCTCTTGCAAGCTACTTCCATGGATTTGATTTTTGTTAAGTTCGCCTACTTGCTC
CE8415./1733         TATCTGCTCTTGCAAGCTACTTCCATGGATTTGATTTTTGTTAAGTTCGCCTACTTGCTC
IQ1332./1762         TATCTGCTCTTGCAAGCTACTTCCATGGATTTGATTTTTGTTAAGTTCGCCTACTTGCTC
ID2618./1625         TATCTGCTCTTGCAAGCTACTTCCATGGATTTGATTTTTGTTAAGTTCGCCTACTTGCTC
XPFF003./1746        TATCTGCTCTTGCAAGCTACTTCCATGGATTTGATTTTTGTTAAGTTCGCCTACTTGCTC
AA3941./1745         TATCTGCTCTTGCAAGCTACTTCCATGGATTTGATTTTTGTTAAGTTCGCCTACTTGCTC
WR0588./1758         TATCTGCTCTTGCAAGCTACTTCCATGGATTTGATTTTTGTTAAGTTCGCCTACTTGCTC
IJ6208./1765         TATCTGCTCTTGCAAGCTACTTCCATGGATTTGATTTTTGTTAAGTTCGCCTACTTGCTC
ID7002./1758         TATCTGCTCTTGCAAGCTACTTCCATGGATTTGATTTTTGTTAAGTTCGCCTACTTGCTC
XPCC003./1670        TATCTGCTCTTGCAAGCTACTTCCATGGATTTGATTTTTGTTAAGTTCGCCTACTTGCTC
CC8032./1708         TATCTGCTCTTGCAAGCTACTTCCATGGATTTGATTTTTGTTAAGTTCGCCTACTTGCTC
DC4015./1698         TATCTGCTCTTGCAAGCTACTTCCATGGATTTGATTTTTGTTAAGTTCGCCTACTTGCTC
BB3004./1415         TATCTGCTCTTGCAAGCTACTTCCATGGATTTGATTTTTGTTAAGTTCGCCTACTTGCTC
mature_miRNA./123    ------------------------------------------------------------
pre_miRNA./1127      ------------------------------------------------------------
```

FIG. 3K

```
AO1008./1792       TCCACGTACGTACTAGCTACATCGTTTCcaCCAGCCCAtGAGGAGTtAttCAatCtaCga
XF7110./1766       TCCACGTACGTACTggCTACATCGTTTCTGC------GCAC------------CACACACCCACCAG
FF6096./1757       TCCACGTACGTACTggCTACATCGTTTCTGC------GCAC------------CACACACCCACCAG
chr2_736214..736992 TCCACGTACGTACTggCTACATCGTTTCTGC------GCAC------------CACACACCCACCAG
XO5744./1755       TCCACGTACGTACTggCTACATCGTTTCTGC------GCAC------------CACACACCCACCAG
ID5829./1612       TCCACGTACGTACTggCTACATCGTTTCTGC------GCAC------------CACACACCCACCAG
FSNU505./1739      TCCACGTACGTACTAGCTACATCGTTTCcaCCAGgcCAtGAGGAGTtAttCAatCtaCga
HT7049HL./1566     TCCACGTACGTACTAGCTACATCGTTTC---------------------------------
AX5707./1763       TCCACGTACGTACTAGCTACATCGTTTCcaCCAGCCCAtGAGGAGTtAttCAatCtaCga
CC7752./1698       TCCACGTACGTACTAGCTACATCGTTTCcaCCAGCCCAAgcCAtGAGGAaTtAttCAatCtaCga
AF4031./1757       TCCACGTACGTACTAGCTACATCGTTTCcaCCAGCCCAtGAGGAGTtAttCAatCtaCga
PJ7065./1782       TCCACGTACGTACTAGCTACATCGTTTCcaCCAGgcCAtGAGGAGTtAtcCAaCagaCga
HH5982./1566       TCCACGTACGTACTAGCTACATCGTTTC---------------------------------
CE8415./1733       TCCACGTACGTACTggCTACATCGTTTCTGC------GCAC------------CACACACCCACCAG
IQ1332./1762       TCCACGTACGTACTAGCTACATCGTTTCcaCCAGCCCAtGAGGAGTtAttCAatCtaCga
ID2618./1625       TCCACGTACGTACwgCTACATCGTTTCTGC------GCAC------------CACACACCCACCAG
XPFF003./1746      TCCACGTACGTACTggCTACATCGTTTCTGC------GCAC------------CACACACCCACCAG
AA3941./1745       TCCACGTACGTACTAGCTACATCGTTTCcaCCAGCCCAtGAGGAGTtAttCAatCtaCga
WR0588./1758       TCCACGTACGTACTAGCTACATCGTTTCTGC------GCAC------------CACACACCCACCAG
IJ6208./1765       TCCACGTACGTACTAGCTACATCGTTTCCaGC------CCAtGAGGAGTtAttCAatCtaCga
ID7002./1758       TCCACGTACGTACTggCTACATCGTTTCTGC------GCAC------------CACACACCCACCAG
XPCC003./1670      TCCACGTACGTACTAGCTACATCGTTTCTGC------GCAC------------CACACACCCACCAG
CC8032./1708       TCCACGTACGTACTAGCTACATCGTTTCTGC------GCAC------------CACACACCCACCAG
DC4015./1698       TCCACGTACGTACTAGCTACATCGTTTCTGC------GCAC------------CACACACCCACCAG
BB3004./1415       ------------------------------------------------------------
mature_miRNA./123                                               ACGTACTGGCTACATC
pre_miRNA./1127                                                 CACGTACGTACTAGCT
SM1481CQA2TT
SM1481CQA1FM
```

FIG. 3L

```
AO1008./1792        Gt----CtgctGcctCCTTCAATTTGCTCATGGGAGCATGmTGATAGATGCAGACAAGTAC
XF7110./1766        GC----CATGAGGAA----TCAATTTGCTCATGGGAGCATGAT----GATGCAGACAAGTAC
FF6096./1757        GC----CATGAGGAA----TCAATTTGCTCATGGGAGCATGAT----GATGCAGACAAGTAC
chr2_736214..736992 GC----CATGAGGAA----TCAATTTGCTCATGGGAGCATGAT----GATGCAGACAAGTAC
XO5744./1755        GC----CATGAGGAA----TCAATTTGCTCATGGGAGCATGAT----GATGCAGACAAGTAC
ID5829./1612        GC----CATGAGGAA----TCAATTTGCTCATGGGAGCATGAT----GATGCAGACAAGTAC
FSNU505./1739       GC----CtgctGcctCCTTCAATTTGCTCATGGGAGCATGATGATGATAGATGCAGACAAGTAC
HT7049HL./1566      ------------------------------------------------------------
AX5707./1763        Gt----CtgctGcctCCTTCAATTTGCTCATGGGAGCATGAT----GAwGCAGACAAGTAC
CC7752./1698        Gt----CtgctGcctCCTTCAATTTGCTCATGGGAGCATGATGATGATAGATGCAGACAAGTAC
AF4031./1757        Gt----CtgctGcctCCTTCAATTTGCTCATGGGAGCATGAT----GATGCAGACAAGTAC
PJ7065./1782        GtaggatgctGcctCC--TCAATTTGCTCATGGGAGCATGAT----GATGCAGACAAGTAC
HH5982./1566        ------------------------------------------------------------
CE8415./1733        GC----CATGAGGAA----TCAATTTGCTCATGGGAGCATGAT----GATGCAGACAAGTAC
IQ1332./1762        Gt----CtgctGcctCCTTCAATTTGCTCATGGGAGCATGATGATGATAGATGCAGACAAGTAC
ID2618./1625        GC----CATGAGGAA----TCAATTysCTCATGGGAGCATGAT----GATGCAGACAAGTAC
XPFF003./1746       GC----CATGAGGAA----TCAATTTGCTCATGGGAGCATGATGATGATAGATGCAGACAAGTAC
AA3941./1745        Gt----CtgctGcctCCTTCAATTTGCTCATGGGAGCATGATGATGATAGATGCAGACAAGTAC
WR0588./1758        GC----CATGAGGAA----TCAATTTGCTCATGGGAGCATGAT----GATGCAGACAAGTAC
IJ6208./1765        Gt----CtgctGcctCCTTCAATTTGCTCATGGGAGCATGATGATGATAGATGCAGACAAGTAC
ID7002./1758        GC----CATGAGGAA----TCAATTTGCTCATGGGAGCATGAT----GATGCAGACAAGTAC
XPCC003./1670       GC----CATGAGGAA----TCAATTTGCTCATGGGAGCATGAT----GATGCAGACAAGTAC
CC8032./1708        GC----CATGAGGAA----TCAATTTGCTCATGGGAGCATGAT----GATGCAGACAAGTAC
DC4015./1698        GC----CATGAGGAA----TCAATTTGCTCATGGGAGCATGAT----GATGCAGACAAGTAC
BB3004./1415        ------------------------------------------------------------
mature_miRNA./123   ------------------------------------------------------------
pre_miRNA./1127     ------------------------------------------------------------
```

FIG. 3M

```
AO1008./1792       AAACATAGTATATAATAAAAAATAGCTGCCGATTCATTCTTyCCTTTCGCTCATCGTTTTC
XF7110./1766       AAACATAGTATATAATAAAAAATAGCTGCCGATTCATTCTTCCTTTCGCTCATCGTTTTC
FF6096./1757       AAACATAGTATATAATAAAAAATAGCTGCCGATTCATTCTTCCTTTCGCTCATCGTTTTC
chr2_736214..736992 AAACATAGTATATAATAAAAAATAGCTGCCGATTCATTCTTCCTTTCGCTCATCGTTTTC
XO5744./1755       AAACATAGTATATAATAAAAAATAGCTGCCGATTCATTCTTCCTTTCGCTCATCGTTTTC
ID5829./1612       AAACATAGTATATAATAAAAAATAGCTGCCGATTCATTCTTCCTTTCGCTCATCGTTTTC
FSNU5O5./1739      AAACATAGTATATAATAAAAAATAGCwGCCGATTmATTCTTyCCTTTCrCTCATCGTTTTC
HT7049HL./1566     ------------------------------------------------------------
AX5707./1763       AAACATAGTATATAATAAAAAATAGCTGCCGATTCATTCTTyCCTTTCGCTCATCGTTTTC
CC7752./1698       AAACATAGTATATAATAAAAAATAGCTGC-------------------------------
AF4031./1757       AAACATAGTATATAATAAAAAATAGCTGCCGATTCATTCTTCCTTTCGCTCATCGTTTTC
PJ7065./1782       AAACATAGTATATAATAAAAAATAGCTGCCGATTCATTCTTCCTTTCGCTCATCGTTTTC
HH5982./1566       ------------------------------------------------------------
CE8415./1733       AAACATAGTATATAATAAAAAATAGCTGCCGATTCATTCTTyCCTTTCGCTCATCGTTTTC
IQ1332./1762       AAACATAGTATATAATAAAAAATAGCTGCCGATTCATTCTTCCTTTCGCTCATCGTTTTC
ID2618./1625       AAACATAGTATATAATAAAAAATAGCTGCCGATTCATTCTTCCTTTCGCTCATCGTTTTC
XPFF003./1746      AAACATAGTATATAATAAAAAATAGCTGCCGATTCATTCTTCCTTTCGCTCATCGTTTTs
AA3941./1745       AAACATAGTATATAATAAAAAATAGCTGCCGATTCATTCTTCCTTTCGCTCATCGTTTTC
WR0588./1758       AAACATAGTATATAATAAAAAATAGCTGCCGATTaATTCTTCCTTTCGCTCATCGTTTTC
IJ6208./1765       AAACATAGTATATAATAAAAAATAGCTGCCGATTCATTCTTyCCTTTCGCTCATCGTTTTC
ID7002./1758       AAACATAGTATATAATAAAAAATAGCTGCCGATTCATTCTTCCTTTCGCTCATCGTTTTC
XPCC003./1670      AAACATAGTATATAATAAAAAATAGCTGCCGATTaATTCTTCCTTTCGCTCATCGTTTTC
CC8032./1708       AAACATAGTATATAATAAAAAATAGCTGCCGATTaATTCTTCCTTTCGCTCATCGTTTTC
DC4015./1698       AAACATAGTATATAATAAAAAATAGCTGCCGATTaATTCTTTCTTTCGCTCATCGTTTTC
BB3004./1415       ------------------------------------------------------------
mature_miRNA./123  ------------------------------------------------------------
pre_miRNA./1127    ------------------------------------------------------------
```

FIG. 3N

```
AO1008./1792       GTAGTTAATTCATTCATTGGCATGGTTAAGTATGTGTAAATACTTACATGTAGATATAT-
XF7110./1766       GTAGTTAATTCATTCATTGGCATGGTTAAGTATGTGTAAATACTTACATGTAGATA----
FF6096./1757       GTAGTTAATTCATTCATTGGCATGGTTAAGTATGTGTAAATACTTACATGTAGATATA--
chr2_736214..736992 GTAGTTAATTCATTCATTGGCATGGTTAAGTATGTGTAAATACTTACATGTAGATATA--
XO5744./1755       GTAGTTAATTCATTCATTGGCATGGTTAAGTATGTGTAAATACTTACATGTAGATATATC
ID5829./1612       GTAGTTAATTCATTCATTGGCATGGTT---------------------------------
FSNU505./1739      GTAGTTAATTC-------------------------------------------------
HT7049HL./1566     ------------------------------------------------------------
AX5707./1763       GTAGTTAATTCATTCATTGGCATGGTTAAGTATGTGTAAATACTTACATGTAGA------
CC7752./1698       ------------------------------------------------------------
AF4031./1757       GTAGTTAATTCATTCATTGGCATGGTTAAGTATGTGTAA---------------------
PJ7065./1782       GTAGTTAATTCATTCATTGGCATGGTTAAGTATGTGTAAATACTTACATGTAGATATATC
HH5982./1566       ------------------------------------------------------------
CE8415./1733       GTAGTTAATTCATTCATTGGCA--------------------------------------
IQ1332./1762       GTAGTTAATTCATTCATTGGCATGGTTAAGTATGTGTAAATACT----------------
ID2618./1625       GTAGTTAATTCATTCATTGGCATGGTTAAGTATGGTTAAGTA------------------
XPFF003./1746      GTAGTTAATTCATTCATTGGCATGGT----------------------------------
AA3941./1745       GTAGTTAATTCATTCATTGGCA--------------------------------------
WR0588./1758       GTAGTTAATTCATTCATTGGCATGGTTAAGTATGTGTAAATACTTACATGTAGATAT---
IJ6208./1765       GTAGTTAATTCATTCATTGGCATGGTTAAGTATGTGTAAATACTTACATGTAGATATAT-
ID7002./1758       GTAGTTAATTCATTCATTGGCATGGTTAAGTATGTGTAAATACTTACATGTAGATA----
XPCC003./1670      GTAGTTAATTCATTCATTGGCATGGT----------------------------------
CC8032./1708       GTAGTTAATTCATTCATTGGCATGGTTA--------------------------------
DC4015./1698       GTAGTTAATTCATTCATTGGCAT-------------------------------------
BB3004./1415       ------------------------------------------------------------
mature_miRNA./123  ------------------------------------------------------------
pre_miRNA./1127    ------------------------------------------------------------
```

FIG. 5

```
ctttaaatag tggcgcgtga cgctgactcc tcgcagaaga atcgtcagcg acccagagc    60
agggcaggga gtccttcctc ccaccagcta gctacgata ctactatcca aagagaatat   120
ggagagattt ccctgagatt gcgcgaatca gtcactgcac gtacgtgtgg agctttttctg  180
ttttctcata aacggcaaat gcagcagcag gaggctttgg gtatttttat tttctctcaa   240
cgattggtaa tcagtatctg ggaaagctgt ggatgtggta gaccgacgtg cgttgagtcg   300
gcatcgtccg gttcatccta tgtattccct ttcctgctat aaataccggc cgggccgagg   360
gtgtcgaagc cgcagatcaa tgcatggcCg cgcgccggcg ccggtaggga tggaggagga   420
ggaagaagag gcggccttgc atgagggcca gagctagcct gcctctggta gccaagatc    480
atggtctcgc tagttccggt tgttgcatgc atgccactat gccagtcctg              540
ctgggtttgt gggcggtctc cttggctagc ctgactggct cttgcctgtc atggaaggcc   600
tcttcttctc tgccacgtac tctcgcctag ctagtcgcct tatggtacgt accgtctgcc   660
tcagtggctc tggcctgtgc ttcgtttgggt ttgccaggta agtatggctg tcgttcattg   720
ctgattcatc agctggctca tatatatgta atgctgcatg caacgctaat atcgttttct   780
taattatttt gttattacct gtgcgtgctt gcagattgtt ctgaattctg aaatgtatgg   840
gttggacatt catcatcttg taccgttgtg ctgcat                             876
```

FIG. 6

```
gatccgattg tcctgcgtat ggctggcagc aggacggagg atctgaagat ctttgaatca   60
ccagtcggcc gatgctcgcg cgtgcctcga ttcttttctc gaggctagct agctacctac  120
aggtgacgca tgcatgcata tatagttgca tctgcgtgtg ttagatgagc acttgtaaaa  180
gagatcatgt gatgaggggg gggggggggg gggagagaga gagagagagg aggaagacgc  240
ggccggacta tttagctatc cgtgtgtgat gaagggcagt agcagtatat gtgctgcttt  300
gatgaattcc atggttggat ggcatggagg gagcgatatt ggcgaggttc aatcagatga  360
tgtatttttc ttatatataa atttgcatgc atgaaggtgt gaatccagtg tcttgattgac 420
ccgcgcaat atcacttcct tccaccataa gtttacacac agagaggatt gcagcgagcg  480
cgtctacttc caaaggttag accactcgtt atttcctcat ttccaaatta cacttgtcta  540
ttatactccc tctgtgtcca tatagtgttc gtttagctt ttctttgtcc atattaaaat  600
agatatcaat gaatatatat atatataata ttttttggagc actagactc taatgactac  660
acgaagccct gacccaacgg tgccatccgg ttcagccaca tcagattcgg ccggctataa  720
aaacactcac acgctaccag agattaggtt ttaacgacgg cgat                   764
```

FIG. 7

```
gacctcacat gacgcttgtc gaccgcggga agcagcatct ccgtggtggg ccctccgtgt    60
cccttcggc cgggatggc ccacgtgcac gtcgaaagcg tgagagcgag aggaggacgc   120
ctacctaagc gagcaatgca acagccatca tcgtcattca ccttgcctat ccatcatcct   180
cgtcttcttc tgtctatcca tggcgatttg gcgttataac caccccacc cccacccttc   240
tctggctacg tccctcgttt cccttcctcc cagctgcctg cccccccttc cctaccctag   300
ctacgcacgc taccagctgc cccccatcca tgccgtccag gaagctggtg gaggactcca   360
acagaacgc acgtcgatcat tctcacctgc cgcctgctgc atgcgatgcg agtcgacgac   420
aagatcagtg caatccctt ggaattttcc actcgcgcct tcacccccgc cgcacgtgcc   480
acacgcccct ccatcttcca tggattccat ctctcatcag gtatctctct ctctatctgc   540
tcttgcaagc tacttccatg gatttgattt ttgttaagtt cgcctacttg ctctccacgt   600
acgtactgc tacatcgttt ctgcgcacca cacacccacc aggccatgag gaatcaattt   660
gctcatggga gcatgatgat gcagacaagt acaaacatag tatataataa aaatagctgc   720
cgattcattc tttcctttcg ctcatcgttt tcgtagttaa ttcattcatt ggcatggtta   780
agtatgtgta aatacttaca tgtagatata tcagggtaaa ggtccagaca ggacccattt   840
aagaggattg aatatgcctg cagc                                          864
```

MICRORNA POLYMORPHISMS CONFERRING ENHANCED DROUGHT TOLERANCE IN A PLANT

CROSS REFERENCES TO RELATED APPLICATIONS

The presently disclosed subject matter claims the benefit of U.S. Provisional Patent Application Ser. No. 61/354,594, filed Jun. 14, 2010; and is a Divisional Application of U.S. Ser. No. 15/242,767 filed on Aug. 22, 2016; the disclosure of all which are herein incorporated by reference.

STATEMENT REGARDING ELECTRONIC FILING OF A SEQUENCE LISTING

A Sequence Listing in ASCII text format, submitted under 37 C.F.R. § 1.821, entitled 72693_ST25.txt, 73 kilobytes in size, generated on Mar. 1, 2016 and filed via EFS-Web, is provided in lieu of a paper copy. This Sequence Listing is hereby incorporated by reference into the specification for its disclosures.

FIELD OF THE INVENTION

The field of the invention relates generally to plants with desirable phenotypic characteristics. The invention relates to identifying plant single nucleotide polymorphisms (SNPs) within microRNA regions that confer desirable agronomic phenotypes. The invention also relates to introgressing desirable agronomic phenotypes into plants by selecting plants comprising for one or more SNPs and breeding with such plants to confer such desirable agronomic phenotypes to plant progeny.

BACKGROUND OF THE INVENTION

A goal of plant breeding is to combine, in a single plant, various desirable traits. For field crops such as corn, these traits can include greater yield and better agronomic quality. However, genetic loci that influence yield and agronomic quality are not always known, and even if known, their contributions to such traits are frequently unclear. Thus, new loci that can positively influence such desirable traits need to be identified and/or the abilities of known loci to do so need to be discovered.

Previous studies have focused primarily on the identification and manipulation of candidate genes that encode proteins, such as transcription factors. These genes could encode proteins that directly affect the physiology of the plant or transcription factors that regulate these effector genes.

miRNAs are post-transcriptional regulators that bind to complementary sequences of target messenger RNA transcripts, and there is evidence that they play an important role in regulating gene activity. These 20-22 nucleotide noncoding RNAs have the ability to hybridize via base pairing with specific target mRNAs and downregulate the expression of these transcripts by mediating either RNA cleavage or translational repression.

Numerous efforts are ongoing to discover miRNA genes that influence plant traits. These efforts rely on classic molecular biology cloning and expression techniques, as well as computational methods (see, e.g., U.S. Patent Application Publication No. 20070118918). miRNAs have already been shown to play important roles in plant development, signal transduction, protein degradation, response to environmental stress and pathogen invasion, and regulate their own biogenesis (Zhang et al. (2006) *Dev. Biol.* 289:3-16). Further, miRNAs have been shown to control a variety of plant developmental processes including flowering time, leaf morphology, organ polarity, floral morphology, and root development (reviewed by Mallory and Vaucheret (2006) *Nat. Genet.* 38:S31-36).

In general, plant miRNAs share a high degree of complementarity with their targets (reviewed by Bonnet et al. (2006) *New Phytol.* 171:451-468), and the predicted mRNA targets of plant miRNAs identified by computational methods encode a wide variety of proteins. Many of these proteins are transcription factors, which may have roles in development. Others are enzymes that have putative roles in mitochondrial metabolism, oxidative stress response, proteasome function, and lignification.

At least 30 miRNA families have been identified in *Arabidopsis* (reviewed by Meyers et al. (2006) *Curr. Opin. Biotech.* 17:1-8), and many of these miRNA sequences are associated with more than one locus, bringing the total number up to approximately 100. As the particular miRNAs identified by various investigators have not generally overlapped, it is assumed that the search for the entire set of miRNAs expressed by a given plant genome, the "miR-Nome," is not yet complete. One reason for this might be that many miRNAs are expressed only under very specific conditions, and thus may have been missed by standard cloning efforts. A study by Sunkar and Zhu (2004, *Plant Cell* 1(6):2001-2019) suggests that, indeed, miRNA discovery may be facilitated by choosing "non-standard" growth conditions for library construction. Sunkar and Zhu identified novel miRNAs in a library consisting of a variety of stress-induced tissues and they demonstrated induction of some of these miRNAs by drought, cold and other stresses, suggesting a role for miRNAs in stress responses. This conclusion is reinforced by the observation that miRNA targeting genes in the sulfur assimilation pathway were shown to be induced under conditions of sulfate starvation (Jones-Rhoades and Bartel (2004) *Mol. Cell.* 14:787-799).

However, what has gone completely unappreciated up to this point is that polymorphisms present in miRNA regions (i.e., a region of a chromosome coding for a mature miRNA, pre-miRNA and flanking sequences) have a measurable impact on plant phenotype. Accordingly, using this knowledge a skilled artisan can manipulate plants and plant materials using both and classic molecular biology techniques and traditional breeding techniques to introduce desirable traits into plant varieties. For example, desirable loci can be introgressed into commercially available plant varieties using marker-assisted selection (MAS) or marker-assisted breeding (MAB). MAS and MAB involves the use of one or more of the molecular markers for the identification and selection of those progeny plants that contain one or more loci that encode the desired traits. Such identification and selection may be based on selection of informative markers that are associated with desired traits. MAB can also be used to develop near-isogenic lines (NIL) harboring loci of interest, allowing a more detailed study of the effect each locus has on a desired trait, and is also an effective method for development of backcross inbred line (BIL) populations.

BRIEF SUMMARY OF THE INVENTION

The following Summary lists several embodiments of the invention subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the invention, whether listed in this Summary or not. To avoid excessive repetition, this Summary does not list or suggest all possible combinations of such features.

The present invention relates to methods of identifying a single nucleotide polymorphism associated with a plant trait. In some embodiments, the single nucleotide polymorphism is located in a flanking sequence portion of a microRNA region. In other embodiments, the single nucleotide polymorphism is located in a pre-miRNA portion of a microRNA region. In yet other embodiments, the single nucleotide polymorphism is located in a mature miRNA portion of a microRNA region. In still other embodiments, the single nucleotide polymorphism is associated with miRNA169g, miRNA171 and miRNA393. In another embodiment, nucleotide polymorphisms associated with miRNA169g, miRNA171 and miRNA393 confer enhanced drought tolerance in a plant.

In some embodiments, the plant is maize. In some embodiments the plant trait is one or more of improved drought tolerance, improved water use optimization, improved ear height, improved plant height, improved grain yield at harvest moisture percentage, improved grain yield at standard moisture percentage, improved anthesis-silk interval, improved grain moisture adjusted percentage, improved grain moisture at harvest, reduced number of days to 50% plants pollen shedding, reduced number of days to 50% plants silking, improved yield grain adjustment at standard moisture, improved yield grain adjustment at harvest moisture, improved ratio of yield grain adjustment at standard moisture to grain moisture adjusted percentage, and improved ratio of yield grain adjustment at standard moisture to grain moisture at harvest.

The present invention also relates to methods of identifying a plant having an improved trait, where the trait is correlated with at least one single nucleotide polymorphism in a microRNA region of a plant genome. In some embodiments, the single nucleotide polymorphism is located in a flanking sequence portion of a microRNA region. In other embodiments, the single nucleotide polymorphism is located in a pre-miRNA portion of a microRNA region. In yet other embodiments, the single nucleotide polymorphism is located in a mature miRNA portion of a microRNA region. In still other embodiments, the single nucleotide polymorphism is associated with miRNA169g, miRNA171 and miRNA393.

In some embodiments, the plant is maize. In some embodiments the plant trait is one or more of improved drought tolerance, improved ear height, improved water use optimization, improved plant height, improved grain yield at harvest moisture percentage, improved grain yield at standard moisture percentage, improved anthesis-silk interval, improved grain moisture adjusted percentage, improved grain moisture at harvest, reduced number of days to 50% plants pollen shedding, reduced number of days to 50% plants silking, improved yield grain adjustment at standard moisture, improved yield grain adjustment at harvest moisture, improved ratio of yield grain adjustment at standard moisture to grain moisture adjusted percentage, and improved ratio of yield grain adjustment at standard moisture to grain moisture at harvest.

In one aspect, compositions and methods for identifying, selecting and producing maize plants with enhanced drought tolerance are provided. A drought tolerant maize plant or germplasm is also provided.

In some embodiments, methods of identifying a drought tolerant maize plant or germplasm are provided. Such methods can comprise detecting, in the maize plant or germplasm, a marker associated with enhanced drought tolerance wherein the marker is associated with a miRNA region (inclusive of flanking region). In one aspect the miRNA region comprises all or a portion of miRNA169g, miRNA171 and miRNA393 microRNA regions. In one aspect, the plant markers for drought tolerance may be found in the flanking sequence of a microRNA region (e.g. miRNA169g, miRNA171 and miRNA393). As used herein, the phrase "marker associated with enhanced drought tolerance" refers to a genomic region and flanking sequence associated with the transcription of a miRNA that possesses certain characteristics (e.g. SNPs, QTLs) that can be associated with enhanced drought tolerance.

In some embodiments, methods of producing a drought tolerant maize plant are provided. Such methods can comprise detecting in a maize germplasm, the presence of a marker associated with enhanced drought tolerance and producing a progeny plant from said maize germplasm.

In some embodiments, the presence of a marker associated with enhanced drought tolerance is detected using a marker probe. In some such embodiments, the presence of a marker associated with enhanced drought tolerance is detected in an amplification product from a nucleic acid sample isolated from a maize plant or germplasm. In some embodiments, the marker comprises a haplotype, and a plurality of probes are used to detect the alleles that make up the haplotype. In some such embodiments, the alleles that make up the haplotype are detected in a plurality of amplification products from a nucleic acid sample isolated from a maize plant or germplasm.

In some embodiments, methods of selecting a drought tolerant maize plant or germplasm are provided. Such methods can comprise crossing a first maize plant or germplasm with a second maize plant or germplasm, wherein the first maize plant or germplasm comprises a marker associated with enhanced drought tolerance, and selecting a progeny plant or germplasm that possesses the marker.

In some embodiments, methods of introgressing an allele associated with enhanced drought tolerance into a maize plant or germplasm are provided. Such methods can comprise crossing a first maize plant or germplasm comprising an allele associated with enhanced drought tolerance with a second maize plant or germplasm that lacks said allele and repeatedly backcrossing progeny plants comprising said allele with the second maize plant or germplasm to produce a drought tolerant maize plant or germplasm comprising the allele associated with enhanced drought tolerance. Progeny comprising the allele associated with enhanced drought tolerance can be identified by detecting, in their genomes, the presence of a marker associated with said allele.

Maize plants and/or germplasms identified, produced or selected by any of the methods of the invention are also provided, as are any progeny or seeds derived from a maize plant or germplasm identified, produced or selected by these methods.

Non-naturally occurring maize plants and/or germplasms comprising one or more markers associated with enhanced drought tolerance are also provided.

Isolated and/or purified markers associated with enhanced drought tolerance are also provided. Such markers can comprise a nucleotide sequence at least 85%, 90%, 95%, or 99% identical to any of SEQ ID NOs: 43, 44, 67, 68, 82, 83 or the reverse complement thereof, or an informative or functional fragment thereof.

Compositions comprising a primer pair capable of amplifying a nucleic acid sample isolated from a maize plant or germplasm to generate a marker associated with enhanced drought tolerance are also provided. Such compositions can comprise, consist essentially of, or consist of one of the amplification primer pairs identified in either one of Tables 1 or 2.

The present invention also relates to isolated nucleic acids comprising a contiguous sequence of at least ten nucleotides selected from portions of the flanking sequence portion of miRNA169g, miRNA171 and miRNA393 microRNA regions that are associated with particular plant traits (i.e. drought tolerance).

The present invention also relates to methods of producing a transgenic plant having an improved trait (e.g. improved abiotic stress tolerance) and plants and plant parts produced thereby.

BRIEF DESCRIPTION OF THE DRAWINGS

These and other features, aspects, and advantages of the present invention are better understood when the following Detailed Description is read with reference to the accompanying figures.

FIGS. 1A-1P. Alignment of miRNA 169g sequence to identify SNPs. The 169g mature miRNA and pre-miRNA are indicated by the identifiers mature_miRNA./123 (SEQ ID NO:43) and pre_miRNA./1141 (SEQ ID NO:44), respectively. The wild type B73 sequence is indicated by the identifier, PUGHP42.R (SEQ ID NO:45). The miR169g locus has been mapped to the survey sequence, PUGHP42.R. The other corn lines aligned are: ID7002./1775 (SEQ ID NO:46); AA3941./1769 (SEQ ID NO:47); AF4031./1743 (SEQ ID NO:48); AX5707./1782 (SEQ ID NO:49); BB3004./1775 (SEQ ID NO:50); CC8032./1763 (SEQ ID NO:51); CE8415./1747 (SEQ ID NO:52); FSNU505./1735 (SEQ ID NO:53); HT7049HL./1754 (SEQ ID NO:54); ID2618./1738 (SEQ ID NO:55); ID5829./1759 (SEQ ID NO:56); IJ6208./1719 (SEQ ID NO:57); IQ1332./1775 (SEQ ID NO:58); WR0588./1759 (SEQ ID NO:59); XF7110./1788 (SEQ ID NO:60); XO5744./1759 (SEQ ID NO:61); XPFF003./1771 (SEQ ID NO:62); XPCC003./1731 (SEQ ID NO:63); PJ7065./1732 (SEQ ID NO:64); FF6096./1784 (SEQ ID NO:65); and CC7752./1770 (SEQ ID NO:66).

FIGS. 2A-2L. Alignment of miRNA 171a sequences to identify SNPs. The 171a mature miRNA and pre-miRNA are indicated by the identifiers mature_miR171a (SEQ ID NO:67) and zma-MIR171a (SEQ ID NO:68), respectively. The wild type B73 sequence is indicated by the identifier, chr4_240118217 ... 240118861 (SEQ ID NO:69). The other corn lines aligned are: IJ6208./1643 (SEQ ID NO:70); AO1008./1626 (SEQ ID NO:71); BB3004./1644 (SEQ ID NO:72); CE8415./1573 (SEQ ID NO:73); DC4015./1587 (SEQ ID NO:74); FF6096./2619 (SEQ ID NO:75); PJ7065./1595 (SEQ ID NO:76); WR0588./1570 (SEQ ID NO:77); XF7110./1464 (SEQ ID NO:78); XO5744./1604 (SEQ ID NO:79); XPCC003./1613 (SEQ ID NO:80); and XPFF003./1622 (SEQ ID NO:81).

FIGS. 3A-3N. Alignment of miRNA 393a sequences to identify SNPs. The mature miRNA and pre-miRNA are indicated by the identifiers mature_miRNA./123 (SEQ ID NO:82) and pre_miRNA./1127 (SEQ ID NO:83), respectively. The wild type B73 sequence is indicated by the identifier, chr2_736214 ... 736992 (SEQ ID NO:84). The other corn lines aligned are: AO1008./1792 (SEQ ID NO:85); XF7110./1766 (SEQ ID NO:86); FF6096./1757 (SEQ ID NO:87); XO5744./1755 (SEQ ID NO:88); ID5829./1612 (SEQ ID NO:89); FSNU505./1739 (SEQ ID NO:90); HT7049HL./1566 (SEQ ID NO:91); AX5707./1763 (SEQ ID NO:92); CC7752./1698 (SEQ ID NO:93); AF4031./1757 (SEQ ID NO:94); PJ7065./1782 (SEQ ID NO:95); HH5982./1566 (SEQ ID NO:96); CE8415./1733 (SEQ ID NO:97); IQ1332./1762 (SEQ ID NO:98); ID2618./1625 (SEQ ID NO:99); XPFF003./1746 (SEQ ID NO:100); AA3941./1745 (SEQ ID NO:101); WR0588./1758 (SEQ ID NO:102); IJ6208./1765 (SEQ ID NO:103); ID7002./1758 (SEQ ID NO:104); XPCC003./1670 (SEQ ID NO:105); CC8032./1708 (SEQ ID NO:106); DC4015./1698 (SEQ ID NO:107); and BB3004./1415 (SEQ ID NO:108).

FIG. 5 shows the 169g amplicon (SEQ ID NO:109). The SNPs are denoted with boxes. The pre-miRNA sequence is underlined, and the mature miRNA sequence is underlined and shaded.

FIG. 6 shows the 171 amplicon (SEQ ID NO:110). The SNPs are denoted with boxes. The pre-miRNA sequence is underlined, and the mature miRNA sequence is underlined and shaded.

FIG. 7 shows the 373 amplicon (SEQ ID NO:111). The SNPs are denoted with boxes. The pre-miRNA sequence is underlined, and the mature miRNA sequence is underlined and shaded.

DETAILED DESCRIPTION OF THE INVENTION

Figure 4:
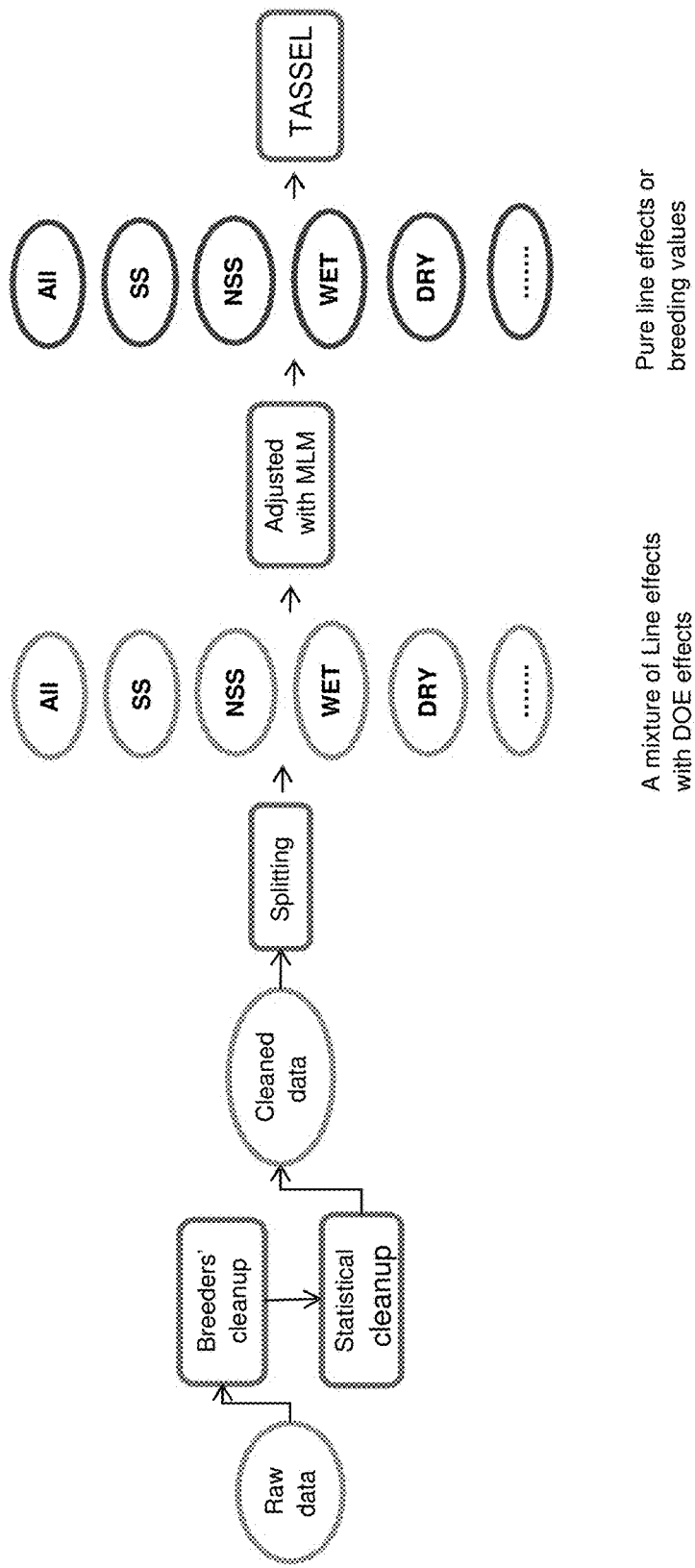
FIG. 4. Procedure for phenotypic data analysis for the hybrid panel. There were two purposes for phenotypic data analysis: data quality control and phenotypic adjustment for fitting association statistical models. Note that prior to phenotypic adjustment, there was also a data splitting process to subset the data according to various experimental conditions (e.g. locations, LD panels, and water treatments). The analysis for the inbred panel was similar but much simpler, because there were fewer data splits.

Maize drought is one of the major limitations to maize production worldwide. When drought stress occurs just before or during the flowering period, an increase in the length of the anthesis-silking interval and a decrease in grain yield can result. Approximately 15% of the world's maize crop, or in excess of 19 million tons, is lost every year to drought. Identifying candidate genes that can enhance drought-stress tolerance in maize could lead to more efficient crop production in affected areas.

What are needed, then, are new methods and compositions for genetically analyzing *Zea mays* varieties with respect to drought tolerance and for employing the information obtained for producing new *Zea mays* plants that have improved water optimization traits.

Increased crop yield is a trait of considerable economic interest throughout the world. Yield is normally defined as the measurable produce of economic value from a crop. This may be defined in terms of quantity and/or quality. Yield is directly dependent on several factors, for example, the number and size of the organs, plant architecture (for example, the number of branches), seed production, leaf senescence and more. Root development, nutrient uptake, stress tolerance and early vigor may also be important factors in determining yield. In addition, it is greatly desirable in agriculture to develop crops that may show increased yield in optimal growth conditions as well as in non-optimal growth conditions (e.g. drought, under abiotic stress conditions). Optimizing the abovementioned factors may therefore contribute to increasing crop yield. In one aspect of the invention, maize plant comprising the nucleotide sequence as described herein may confer increased yield under optimal as well as in non-optimal conditions (e.g. drought or decreased water availability) as compared to a control plant.

Plants engineered for improved yield under various biotic and abiotic stresses is of special interest in the field of agriculture. For example, abiotic stress is a primary cause of crop loss worldwide, reducing average yields for most major crop plants by more than 50% (Wang et al., Planta (2003) 218: 1-14). Abiotic stresses may be caused by drought, floods, salinity, extremes of temperature, chemical toxicity and oxidative stress. The ability to improve plant tolerance to abiotic stress would be of great economic advantage to farmers worldwide and would allow for the cultivation of crops during adverse conditions and in territories where cultivation of crops may not otherwise be possible.

The presently disclosed subject matter provides compositions and methods for identifying, selecting, and/or producing maize plants with enhanced drought tolerance (also referred to herein as water optimization), as well as maize plants identified, selected and/or produced by a method of this invention. In addition, the presently disclosed subject matter provides maize plants and/or germplasms having within their genomes one or more markers associated with enhanced drought tolerance. Maize plants produced using the methods described herein may confer any one of the following increased water use optimization, enhanced drought tolerance, increased tolerance to abiotic stress, increased yield under optimal or non-optimal growing conditions, increased yield under limited irrigation or increased vigor.

To assess the value of alleles and/or haplotypes under drought stress, diverse germplasm may be screened in controlled field-experiments comprising a full irrigation control treatment and a limited irrigation treatment. A goal of the full irrigation treatment is to ensure that water did not limit the productivity of the crop. In contrast, a goal of the limited irrigation treatment is to ensure that water is the major limiting constraint to grain yield. Main effects (e.g., treatment and genotype) and interactions (e.g., genotype× treatment) may be determined when the two treatments are applied adjacent to one another in the field. Moreover, drought related phenotypes could be quantified for each genotype in the panel thereby allowing for marker trait associations to be conducted.

In practice, the method for the limited irrigation treatment can vary widely depending upon the germplasm being screened, the soil type, climatic conditions at the site, pre-season water supply, and in-season water supply, to name just a few. Initially, a site is identified where in-season precipitation is low (to minimize the chance of unintended water application) and is suitable for cropping. In addition, determining the timing of the stress can be important, such that a target is defined to ensure that year-to-year, or location-to-location, screening consistency is in place. An understanding of the treatment intensity, or in some cases the yield loss desired from the limited irrigation treatment, can also be considered. Selection of a treatment intensity that is too light can fail to reveal genotypic variation. Selection of a treatment intensity that is too heavy can create large experimental error. Once the timing of stress is identified and treatment intensity is described, irrigation can be managed in a manner that is consistent with these targets.

For the purposes of this specification, unless otherwise indicated, all numbers expressing quantities, conditions, and so forth used in the specification are to be understood as being modified in all instances by the term "about." Accordingly, unless indicated to the contrary, the numerical parameters set forth in the following specification are approximations that can vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a stated range of "1 to 10" should be considered to include any and all subranges between, and inclusive of, the minimum value of 1 and the maximum value of 10; that is, all subranges beginning with a minimum value of 1 or more, e.g. 1 to 6.1, and ending with a maximum value of 10 or less, e.g., 5.5 to 10.

Units, prefixes, and symbols may be denoted in their SI accepted form. Unless otherwise indicated, nucleic acids are written left to right in 5' to 3' orientation; amino acid sequences are written left to right in amino to carboxyl orientation, respectively. Numeric ranges recited within the specification are inclusive of the numbers defining the range and include each integer within the defined range. Amino acids may be referred to herein by either commonly known three letter symbols or by the one-letter symbols recommended by the IUPAC-IUB Biochemical Nomenclature Commission. Nucleotides, likewise, may be referred to by their commonly accepted single-letter codes. The terms described below are more fully explained by reference to the specification as a whole.

It is further noted that, as used in this specification, the singular forms "a," "an," and "the" include plural referents unless expressly and unequivocally limited to one referent.

"Plant" includes reference to whole plants, plant organs, plant tissues, seeds and plant cells and progeny of same. Plant cells include, without limitation, cells from seeds, suspension cultures, embryos, meristematic regions, callus tissue, leaves, roots, shoots, gametophytes, sporophytes, pollen, and microspores.

As used herein, the term plant is also used in its broadest sense, including, but is not limited to, any species of woody, ornamental or decorative, crop or cereal, fruit or vegetable plant, and algae (e.g., *Chlamydomonas reinhardtii*). Non-limiting examples of plants include plants from the genus *Arabidopsis* or the genus *Oryza*. Other examples include plants from the genuses *Acorus, Aegilops, Allium, Amborella, Antirrhinum, Apium, Arachis, Beta, Betula, Brassica, Capsicum, Ceratopteris, Citrus, Cryptomeria, Cycas, Descurainia, Eschscholzia, Eucalyptus, Glycine, Gossypium, Hedyotis, Helianthus, Hordeum, Ipomoea, Lactuca, Linum, Liriodendron, Lotus, Lupinus, Lycopersicon, Medicago, Mesembryanthemum, Nicotiana, Nuphar, Pennisetum, Persea, Phaseolus, Physcomitrella, Picea, Pinus, Poncirus, Populus, Prunus, Robinia, Rosa, Saccharum, Schedonorus, Secale, Sesamum, Solanum, Sorghum, Stevia, Thellungiella,*

*Theobroma, Triphysaria, Triticum, Vitis, Zea,* or *Zinnia*. Still other examples of plants include, but are not limited to, wheat, cauliflower, tomato, tobacco, corn, *petunia*, trees, etc. As used herein, the term "cereal crop" is used in its broadest sense. The term includes, but is not limited to, any species of grass, or grain plant (e.g., barley, corn, oats, rice, wild rice, rye, wheat, millet, sorghum, triticale, etc.), non-grass plants (e.g., buckwheat flax, legumes or soybeans, etc.). As used herein, the term "crop" or "crop plant" is used in its broadest sense. The term includes, but is not limited to, any species of plant or algae edible by humans or used as a feed for animals or used, or consumed by humans, or any plant or algae used in industry or commerce.

The term "plant part" includes differentiated and undifferentiated tissues including, but not limited to the following: roots, stems, shoots, leaves, pollen, seeds, tumor tissue and various forms of cells and culture (e.g., single cells, protoplasts, embryos and callus tissue). The plant tissue may be in plant or in a plant organ, tissue or cell culture. The aforementioned term also includes plant products, such as grain, fruits, and nuts.

The term "plant organ" refers to plant tissue or group of tissues that constitute a morphologically and functionally distinct part of a plant.

The term "genome" refers to the following: (1) the entire complement of genetic material (genes and non-coding sequences) present in each cell of an organism, or virus or organelle; (2) a complete set of chromosomes inherited as a (haploid) unit from one parent.

As used herein "Plant sample" refers to either intact or non-intact (e.g. milled seed or plant tissue, chopped plant tissue, lyophilized tissue) plant tissue.

"Progeny" comprises any subsequent generation of a plant. Progeny will inherit, and stably segregate, genes and transgenes from its parent plant(s).

As used herein, the term "allele" refers to a variant or an alternative sequence form at a genetic locus. In diploids, a single allele is inherited by a progeny individual separately from each parent at each locus. The two alleles of a given locus present in a diploid organism occupy corresponding places on a pair of homologous chromosomes, although one of ordinary skill in the art understands that the alleles in any particular individual do not necessarily represent all of the alleles that are present in the species.

As used herein, the term "anthesis silk interval" (ASI) refers to the difference between when a plant starts shedding pollen (anthesis) and when it begins producing silk (female). Data are collected on a per plot basis. In some embodiments, this interval is expressed in days.

As used herein, the phrase "associated with" refers to a recognizable and/or assayable relationship between two entities. For example, the phrase "associated with a water optimization trait" refers to a trait, locus, gene, allele, marker, phenotype, etc., or the expression thereof, the presence or absence of which can influence an extent, degree, and/or rate at which a plant or a part of interest thereof that has the water optimization trait grows. As such, a marker is "associated with" a trait when it is linked to it and when the presence of the marker is an indicator of whether and/or to what extent the desired trait or trait form will occur in a plant/germplasm comprising the marker. Similarly, a marker is "associated with" an allele when it is linked to it and when the presence of the marker is an indicator of whether the allele is present in a plant/germplasm comprising the marker. For example, "a marker associated with enhanced drought tolerance" refers to a marker whose presence or absence can be used to predict whether and/or to what extent a plant will display a drought tolerant phenotype.

As used herein, the terms "backcross" and "backcrossing" refer to the process whereby a progeny plant is repeatedly crossed back to one of its parents. In a backcrossing scheme, the "donor" parent refers to the parental plant with the desired gene or locus to be introgressed. The "recipient" parent (used one or more times) or "recurrent" parent (used two or more times) refers to the parental plant into which the gene or locus is being introgressed. For example, see Ragot, M. et al. *Marker-assisted Backcrossing: A Practical Example*, in Techniques et Utilisations des Marqueurs Moleculaires Les Colloques, Vol. 72, pp. 45-56 (1995); and Openshaw et al., *Marker-assisted Selection in Backcross Breeding*, in Proceedings of the Symposium "Analysis of Molecular Marker Data," pp. 41-43 (1994). The initial cross gives rise to the F1 generation. The term "BC1" refers to the second use of the recurrent parent, "BC2" refers to the third use of the recurrent parent, and so on. In some embodiments, a backcross is performed repeatedly, with a progeny individual of each successive backcross generation being itself backcrossed to the same parental genotype.

A centimorgan ("cM") is a unit of measure of recombination frequency. One cM is equal to a 1% chance that a marker at one genetic locus will be separated from a marker at a second locus due to crossing over in a single generation.

As used herein, the term "chromosome" is used in its art-recognized meaning of the self-replicating genetic structure in the cellular nucleus containing the cellular DNA and bearing in its nucleotide sequence the linear array of genes. The *Zea mays* chromosome numbers disclosed herein refer to those as set forth in Perin et al., 2002, which relates to a reference nomenclature system adopted by L'institut National da la Recherché Agronomique (INRA; Paris, France).

As used herein, the phrase "consensus sequence" refers to a sequence of DNA built to identify nucleotide differences (e.g., SNP and Indel polymorphisms) in alleles at a locus. A consensus sequence can be either strand of DNA at the locus and states the nucleotide(s) at one or more positions (e.g., at one or more SNPs and/or at one or more Indels) in the locus. In some embodiments, a consensus sequence is used to design oligonucleotides and probes for detecting polymorphisms in the locus.

The term "comprising", which is synonymous with "including" "containing", or "characterized by", is inclusive or open-ended and does not exclude additional, unrecited elements and/or method steps. "Comprising" is a term of art that means that the named elements and/or steps are present, but that other elements and/or steps can be added and still fall within the scope of the relevant subject matter.

As used herein, the phrase "consisting of" excludes any element, step, or ingredient not specifically recited. For example, when the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of the related disclosure or claim to the specified materials and/or steps, plus those that do not materially affect the basic and novel characteristic(s) of the disclosed and/or claimed subject matter. For example, the presently disclosed subject matter relates in some embodiments to introgressing favorable alleles and/or haplotypes into maize plants. One locus that comprises certain favorable alleles and/or haplotypes is represented by SEQ ID NO: 7, which includes nine (9) different polymorphisms as set forth herein, with nine different favorable alelles. For any given introgression effort with respect to the genetic locus corresponding to SEQ ID NO: 7, the method can "consist essentially of" introgressing a particular favorable allele selected from among these nine polymorphic locations, which means that the recited favorable allele is the only favorable allele introgressed into a progeny genome. It is noted, however, that additional polymorphic loci will also be introgressed into the genome, although the effects thereof might be unknown or not of interest.

With respect to the terms "comprising", "consisting essentially of", and "consisting of", where one of these three terms is used herein, the presently disclosed and claimed subject matter can include the use of either of the other two terms. For example, the presently disclosed subject matter relates in some embodiments to oligonucleotide primers comprise any of SEQ ID NOs: 118-399 and 402-413. It is understood that the presently disclosed subject matter thus also encompasses oligonucleotide primers that in some embodiments consist essentially of any of SEQ ID NOs: 118-399 and 402-113, as well as oligonucleotide primers that in some embodiments consist of any of SEQ ID NOs: 118-399 and 402-113. Similarly, it is also understood that in some embodiments the methods of the presently disclosed subject matter comprise the steps that are disclosed herein, in some embodiments the methods of the presently disclosed subject matter consist essentially of the steps that are disclosed, and in some embodiments the methods of the presently disclosed subject matter consist of the steps that are disclosed herein.

As used herein, the terms "cross" or "crossed" refer to the fusion of gametes via pollination to produce progeny (e.g., cells, seeds or plants). The term encompasses both sexual crosses (the pollination of one plant by another) and selfing (self-pollination, e.g., when the pollen and ovule are from the same plant). The term "crossing" refers to the act of fusing gametes via pollination to produce progeny.

As used herein, the terms "cultivar" and "variety" refer to a group of similar plants that by structural or genetic features and/or performance can be distinguished from other varieties within the same species.

As used herein, the terms "desired allele" and "allele of interest" are used interchangeably to refer to an allele associated with a desired trait. In some embodiments, a "desired allele" and/or "allele of interest" can be associated with either an increase or a decrease of or in a given trait, depending on the nature of the desired phenotype. In some embodiments, a "desired allele" and/or "allele of interest" can be associated with a change in morphology, color, etc.

As used herein, the terms "drought tolerance" and "drought tolerant" refer to a plant's ability to endure and/or thrive under drought stress conditions. When used in reference to germplasm, the terms refer to the ability of a plant that arises from that germplasm to endure and/or thrive under drought conditions. In general, a plant or germplasm is labeled as "drought tolerant" if it displays "enhanced drought tolerance."

As used herein, the term "enhanced drought tolerance" refers to an improvement, enhancement, or increase in one or more water optimization phenotypes as compared to one or more control plants (e.g., one or both of the parents, or a plant lacking a marker associated with enhanced drought tolerance). Exemplary water optimization phenotypes include, but are not limited to, grain yield at standard moisture percentage (YGSMN), grain moisture at harvest (GMSTP), grain weight per plot (GWTPN), percent yield recovery (PYREC), yield reduction (YRED), anthesis silk interval (ASI) and percent barren (PB). Thus, a plant that demonstrates higher YGSMN than one or both of its parents when each is grown under drought stress conditions displays enhanced drought tolerance and can be labeled as "drought tolerant."

The phrase "abiotic stress" as used herein refers to any adverse effect on metabolism, growth, reproduction and/or viability of a plant by abiotic factors (i.e. water availability, heat, cold, and etc). Accordingly, abiotic stress can be induced by suboptimal environmental growth conditions such as, for example, salinity, water deprivation, water deficit, drought, flooding, freezing, low or high temperature (e.g., chilling or excessive heat), toxic chemical pollution, heavy metal toxicity, anaerobiosis, nutrient deficiency, nutrient excess, atmospheric pollution or UV irradiation.

The phrase "abiotic stress tolerance" as used herein refers to the ability of a plant to endure an abiotic stress without suffering a substantial alteration in metabolism, growth, productivity and/or viability. Plants produced using the methods herein confer an increased abiotic stress tolerance as compared to a control plant.

Water Use Efficiency (WUE) is a parameter frequently used to estimate the tradeoff between water consumption and CO2 uptake/growth (Kramer, 1983, Water Relations of Plants, Academic Press p. 405). WUE has been defined and measured in multiple ways. One approach is to calculate the ratio of whole plant dry weight, to the weight of water consumed by the plant throughout its life (Chu et al., 1992, Oecologia 89:580). Another variation is to use a shorter time interval when biomass accumulation and water use are measured (Mian et al., 1998, Crop Sci. 38:390). Another approach is to utilize measurements from restricted parts of the plant, for example, measuring only aerial growth and water use (Nienhuis et al 1994 Amer J Bot 81:943). WUE also has been defined as the ratio of CO2 uptake to water vapor loss from a leaf or portion of a leaf, often measured over a very short time period (e.g. seconds/minutes) (Kramer, 1983, p. 406). The ratio of 13C/12C fixed in plant tissue, and measured with an isotope ratio mass-spectrometer, also has been used to estimate WUE in plants using C-3 photosynthesis (Martin et al., 1999, Crop Sci. 1775). As used herein, the term "water use efficiency" refers to the amount of organic matter produced by a plant divided by the amount of water used by the plant in producing it, i.e. the dry weight of a plant in relation to the plant's water use. As used herein, the term "dry weight" refers to everything in the plant other than water, and includes, for example, carbohydrates, proteins, oils, and mineral nutrients. It is contemplated that the plants produced by the methods described herein will confer an increase in water use efficiency.

A "control plant" or "control" as used herein may be a plant of the same line or variety as the plant being tested, lacking the specific trait conferring a specific phenotype (i.e. enhanced drought tolerance). Such a progenitor plant that lacks that specific trait conferring can be a natural, wild-type plant, an elite, non-transgenic plant, or a transgenic plant without the specific trait.

As used herein "water deficit" means a period when water available to a plant is not replenished at the rate at which it is consumed by the plant. A long period of water deficit is colloquially called drought. Lack of rain or irrigation may not produce immediate water stress if there is an available reservoir of ground water to support the growth rate of plants. Plants grown in soil with ample groundwater can survive days without rain or irrigation without adverse affects on yield. Plants grown in dry soil are likely to suffer adverse affects with minimal periods of water deficit. Severe water deficit stress can cause wilt and plant death; moderate drought can reduce yield, stunt growth or retard development. Plants can recover from some periods of water deficit stress without significantly affecting yield. However, water deficit at the time of pollination can lower or reduce yield. Thus, a useful period in the life cycle of corn, for example, for observing response or tolerance to water deficit is the late vegetative stage of growth before tassel emergence or the transition to reproductive development. Tolerance to water deficit is determined by comparison to control plants. For instance, plants of this invention can produce a higher yield than control plants when exposed to water deficit. In the laboratory and in field trials drought can be simulated by giving plants of this invention and control plants less water than is given to sufficiently-watered control plants and measuring differences in traits. One aspect of the invention provides plants produced by the methods disclosed herein which confers a higher tolerance to a water deficit.

As used herein, the terms "elite" and "elite line" refer to any line that is substantially homozygous and has resulted from breeding and selection for desirable agronomic performance.

As used herein, the term "gene" refers to a hereditary unit including a sequence of DNA that occupies a specific location on a chromosome and that contains the genetic instruction for a particular characteristic or trait in an organism.

A "genetic map" is a description of genetic linkage relationships among loci on one or more chromosomes within a given species, generally depicted in a diagrammatic or tabular form. For each genetic map, distances between loci are measured by the recombination frequencies between them. Recombinations between loci can be detected using a variety of markers. A genetic map is a product of the mapping population, types of markers used, and the polymorphic potential of each marker between different populations. The order and genetic distances between loci can differ from one genetic map to another.

As used herein, the phrase "genetic marker" refers to a nucleic acid sequence (e.g., a polymorphic nucleic acid sequence) that has been identified as associated with a locus or allele of interest and that is indicative of the presence or absence of the locus or allele of interest in a cell or organism. Examples of genetic markers include, but are not limited to genes, DNA or RNA-derived sequences, promoters, any untranslated regions of a gene, microRNAs, siRNAs, QTLs, transgenes, mRNAs, ds RNAs, transcriptional profiles, and methylation patterns.

As used herein, the term "genotype" refers to the genetic constitution of an individual (or group of individuals) at one or more genetic loci, as contrasted with the observable and/or detectable and/or manifested trait (the phenotype). Genotype is defined by the allele(s) and/or haplotype(s) of one or more known loci that the individual has inherited from its parents. The term genotype can be used to refer to an individual's genetic constitution at a single locus, at multiple loci, or more generally, the term genotype can be used to refer to an individual's genetic make-up for all the genes in its genome. Genotypes can be indirectly characterized, e.g., using markers and/or directly characterized by nucleic acid sequencing.

As used herein, the term "germplasm" refers to genetic material of or from an individual (e.g., a plant), a group of individuals (e.g., a plant line, variety or family), or a clone derived from a line, variety, species, or culture. The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm includes cells, seed or tissues from which new plants can be grown, as well as plant parts, such as leafs, stems, pollen, or cells that can be cultured into a whole plant.

A "haplotype" is the genotype of an individual at a plurality of genetic loci, i.e., a combination of alleles. Typically, the genetic loci that define a haplotype are physically and genetically linked, i.e., on the same chromosome segment. The term "haplotype" can refer to polymorphisms at a particular locus, such as a single marker locus, or polymorphisms at multiple loci along a chromosomal segment.

A "heterotic group" comprises a set of genotypes that perform well when crossed with genotypes from a different heterotic group. Hallauer et al., Corn breeding, in CORN AND CORN IMPROVEMENT p. 463-564 (1998). Inbred lines are classified into heterotic groups, and are further subdivided into families within a heterotic group, based on several criteria such as pedigree, molecular marker-based associations, and performance in hybrid combinations. Smith et al., Theor. Appl. Gen. 80:833 (1990).

As used herein, the term "heterozygous" refers to a genetic status wherein different alleles reside at corresponding loci on homologous chromosomes. As used herein, the term "homozygous" refers to a genetic status wherein identical alleles reside at corresponding loci on homologous chromosomes. It is noted that both of these terms can refer to single nucleotide positions, multiple nucleotide positions, whether contiguous or not, or entire loci on homologous chromosomes.

As used herein, the term "hybrid" refers to a seed and/or plant produced when at least two genetically dissimilar parents are crossed.

As used herein, the term "hybrid" when used in the context of nucleic acids, refers to a double-stranded nucleic acid molecule, or duplex, formed by hydrogen bonding between complementary nucleotide bases. The terms "hybridize" and "anneal" refer to the process by which single strands of nucleic acid sequences form double-helical segments through hydrogen bonding between complementary bases.

As used herein, the phrase "ILLUMINA® GOLDENGATE® Assay" refers to a high throughput genotyping assay sold by Illumina Inc. of San Diego, Calif., United States of America that can generate SNP-specific PCR products. This assay is described in detail at the website of Illumina Inc. and in Fan et al., 2006.

As used herein, the phrase "immediately adjacent", when used to describe a nucleic acid molecule that hybridizes to DNA containing a polymorphism, refers to a nucleic acid that hybridizes to a DNA sequence that directly abuts the polymorphic nucleotide base position. For example, a nucleic acid molecule that can be used in a single base extension assay is "immediately adjacent" to the polymorphism.

As used herein, the term "improved", and grammatical variants thereof, refers to a plant or a part, progeny, or tissue culture thereof, that as a consequence of having (or lacking) a particular water optimization associated allele (such as, but not limited to those water optimization associated alleles disclosed herein) is characterized by a higher or lower content of a water optimization associated trait, depending on whether the higher or lower content is desired for a particular purpose.

As used herein, the term "inbred" refers to a substantially homozygous plant or variety. The term can refer to a plant or variety that is substantially homozygous throughout the entire genome or that is substantially homozygous with respect to a portion of the genome that is of particular interest.

As used herein, the term "INDEL" (also spelled "indel") refers to an insertion or deletion in a pair of nucleotide sequences, wherein a first sequence can be referred to as having an insertion relative to a second sequence or the second sequence can be referred to as having a deletion relative to the first sequence.

As used herein, the term "informative fragment" refers to a nucleotide sequence comprising a fragment of a larger nucleotide sequence, wherein the fragment allows for the identification of one or more alleles within the larger nucleotide sequence.

As used herein, the terms "introgression," "introgressing" and "introgressed" refer to both the natural and artificial transmission of a desired allele or combination of desired alleles of a genetic locus or genetic loci from one genetic background to another. For example, a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele can be a selected allele of a marker, a QTL, a transgene, or the like. Offspring comprising the desired allele can be repeatedly backcrossed to a line having a desired genetic background and selected for the desired allele, with the result being that the desired allele becomes fixed in the desired genetic background. For example, a marker associated with enhanced drought tolerance can be introgressed from a donor into a recurrent parent that is not drought tolerant or only partially drought tolerant. The resulting offspring could then be repeatedly backcrossed and selected until the progeny possess the drought tolerance allele in the recurrent parent background.

As such, "linkage" typically implies and can also refer to physical proximity on a chromosome. Thus, two loci are linked if they are within in some embodiments 20 centiMorgans (cM), in some embodiments 15 cM, in some embodiments 12 cM, in some embodiments 10 cM, in some embodiments 9 cM, in some embodiments 8 cM, in some embodiments 7 cM, in some embodiments 6 cM, in some embodiments 5 cM, in some embodiments 4 cM, in some embodiments 3 cM, in some embodiments 2 cM, and in some embodiments 1 cM of each other. Similarly, a yield locus of the presently disclosed subject matter is linked to a marker (e.g., a genetic marker) if it is in some embodiments within 20, 15, 12, 10, 9, 8, 7, 6, 5, 4, 3, 2, or 1 cM of the marker.

Thus, the term "linkage" refers to the degree with which one marker locus is associated with another marker locus or some other locus (for example, a drought tolerance locus). The linkage relationship between a molecular marker and a phenotype can be given as a "probability" or "adjusted probability." Linkage can be expressed as a desired limit or range. For example, in some embodiments, any marker is linked (genetically and physically) to any other marker when the markers are separated by less than about 50, 40, 30, 25, 20, or 15 map units (or cM).

In some embodiments of the presently disclosed subject matter, it is advantageous to define a bracketed range of linkage, for example, from about 10 cM and about 20 cM, from about 10 cM and about 30 cM, or from about 10 cM and about 40 cM. The more closely a marker is linked to a second locus, the better an indicator for the second locus that marker becomes. Thus, "closely linked loci" such as a marker locus and a second locus display an inter-locus recombination frequency of about 10%, 9%, 8%, 7%, 6%, 5%, 4%, 3%, or 2% or less. In some embodiments, the relevant loci display a recombination frequency of about 1% or less, e.g., about 0.75%, 0.5%, 0.25% or less. Two loci that are localized to the same chromosome, and at such a distance that recombination between the two loci occurs at a frequency of less than about 10% (e.g., about 9%, 8%, 7%, 6%, 5%, 4%, 3%, 2%, 1%, 0.75%, 0.5%, or 0.25%, or less) can also be said to be "proximal to" each other. Since one cM is the distance between two markers that show a 1% recombination frequency, any marker is closely linked (genetically and physically) to any other marker that is in close proximity, e.g., at or less than about 10 cM distant. Two closely linked markers on the same chromosome can be positioned about 9, 8, 7, 6, 5, 4, 3, 2, 1, 0.75, 0.5 or 0.25 cM or less from each other.

As used herein, the term "linkage disequilibrium" refers to a non-random segregation of genetic loci or traits (or both). In either case, linkage disequilibrium implies that the relevant loci are within sufficient physical proximity along a length of a chromosome so that they segregate together with greater than random (i.e., non-random) frequency (in the case of co-segregating traits, the loci that underlie the traits are in sufficient proximity to each other). Markers that show linkage disequilibrium are considered linked. Linked loci co-segregate more than 50% of the time, e.g., from about 51% to about 100% of the time. In other words, two markers that co-segregate have a recombination frequency of less than 50% (and, by definition, are separated by less than 50 cM on the same chromosome). As used herein, linkage can be between two markers, or alternatively between a marker and a phenotype. A marker locus can be "associated with" (linked to) a trait, e.g., drought tolerance. The degree of linkage of a molecular marker to a phenotypic trait is measured, e.g., as a statistical probability of co-segregation of that molecular marker with the phenotype.

Linkage disequilibrium is most commonly assessed using the measure $r^2$, which is calculated using the formula described by Hill and Robertson, *Theor. Appl. Genet.* 38:226 (1968). When $r^2=1$, complete linkage disequilibrium exists between the two marker loci, meaning that the markers have not been separated by recombination and have the same allele frequency. Values for $r^2$ above ⅓ indicate sufficiently strong linkage disequilibrium to be useful for mapping. Ardlie et al., *Nature Reviews Genetics* 3:299 (2002). Hence, alleles are in linkage disequilibrium when $r^2$ values between pairwise marker loci are greater than or equal to about 0.33, 0.4, 0.5, 0.6, 0.7, 0.8, 0.9, or 1.0.

As used herein, the term "linkage equilibrium" describes a situation where two markers independently segregate, i.e., sort among progeny randomly. Markers that show linkage equilibrium are considered unlinked (whether or not they lie on the same chromosome). As such, the phrase "linkage disequilibrium" is defined as change from the expected relative frequency of gamete types in a population of many individuals in a single generation such that two or more loci act as genetically linked loci. If the frequency in a population of allele S is x, s is x', B is y, and b is y', then the expected frequency of genotype SB is xy, that of Sb is xy', that of sB is x'y, and that of sb is x'y', and any deviation from these frequencies is an example of disequilibrium.

As used herein, the phrase "linkage group" refers to all of the genes or genetic traits that are located on the same chromosome. Within the linkage group, those loci that are close enough together can exhibit linkage in genetic crosses. Since the probability of crossover increases with the physical distance between loci on a chromosome, loci for which the locations are far removed from each other within a linkage group might not exhibit any detectable linkage in direct genetic tests. The term "linkage group" is mostly used to refer to genetic loci that exhibit linked behavior in genetic systems where chromosomal assignments have not yet been made. Thus, in the present context, the term "linkage group" is synonymous with the physical entity of a chromosome, although one of ordinary skill in the art will understand that a linkage group can also be defined as corresponding to a region of (i.e., less than the entirety) of a given chromosome.

A "locus" is a position on a chromosome where a gene or marker or allele is located. In some embodiments, a locus can encompass one or more nucleotides.

As used herein, the term "maize" refers to a plant of the Zea mays L. ssp. mays and is also known as "corn."

As used herein, the term "maize plant" includes whole maize plants, maize plant cells, maize plant protoplast, maize plant cell or maize tissue cultures from which maize plants can be regenerated, maize plant calli, and maize plant cells that are intact in maize plants or parts of maize plants, such as maize seeds, maize cobs, maize flowers, maize cotyledons, maize leaves, maize stems, maize buds, maize roots, maize root tips, and the like.

As used herein, the terms "marker", "genetic marker", and 'molecular marker" are used interchangeably to refer to an identifiable position on a chromosome the inheritance of which can be monitored and/or a reagent that is used in methods for visualizing differences in nucleic acid sequences present at such identifiable positions on chromosomes. Thus, in some embodiments a marker comprises a known or detectable nucleic acid sequence. Examples of markers include, but are not limited to genetic markers, protein composition, peptide levels, protein levels, oil composition, oil levels, carbohydrate composition, carbohydrate levels, fatty acid composition, fatty acid levels, amino acid composition, amino acid levels, biopolymers, starch composition, starch levels, fermentable starch, fermentation yield, fermentation efficiency (e.g., captured as digestibility at 24, 48, and/or 72 hours), energy yield, secondary compounds, metabolites, morphological characteristics, and agronomic characteristics. As such, a marker can comprise a nucleotide sequence that has been associated with an allele or alleles of interest and that is indicative of the presence or absence of the allele or alleles of interest in a cell or organism and/or to a reagent that is used to visualize differences in the nucleotide sequence at such an identifiable position or positions. A marker can be, but is not limited to, an allele, a gene, a haplotype, a restriction fragment length polymorphism (RFLP), a simple sequence repeat (SSR), random amplified polymorphic DNA (RAPD), cleaved amplified polymorphic sequences (CAPS) (Rafalski and Tingey, *Trends in Genetics* 9:275 (1993)), an amplified fragment length polymorphism (AFLP) (Vos et al., *Nucleic Acids Res.* 23:4407 (1995)), a single nucleotide polymorphism (SNP) (Brookes, *Gene* 234:177 (1993)), a sequence-characterized amplified region (SCAR) (Paran and Michelmore, *Theor. Appl. Genet.* 85:985 (1993)), a sequence-tagged site (STS) (Onozaki et al., *Euphytica* 138:255 (2004)), a single-stranded conformation polymorphism (SSCP) (Orita et al., *Proc. Natl. Acad. Sci. USA* 86:2766 (1989)), an inter-simple sequence repeat (ISSR) (Blair et al., *Theor. Appl. Genet.* 98:780 (1999)), an inter-retrotransposon amplified polymorphism (IRAP), a retrotransposon-microsatellite amplified polymorphism (REMAP) (Kalendar et al., *Theor. Appl. Genet.* 98:704 (1999)) or an RNA cleavage product (such as a Lynx tag). A marker can be present in genomic or expressed nucleic acids (e.g., ESTs). The term marker can also refer to nucleic acids used as probes or primers (e.g., primer pairs) for use in amplifying, hybridizing to and/or detecting nucleic acid molecules according to methods well known in the art. A large number of maize molecular markers are known in the art, and are published or available from various sources, such as the Maize GDB internet resource and the Arizona Genomics Institute internet resource run by the University of Arizona.

In some embodiments, a marker corresponds to an amplification product generated by amplifying a *Zea mays* nucleic acid with one or more oligonucleotides, for example, by the polymerase chain reaction (PCR). As used herein, the phrase "corresponds to an amplification product" in the context of a marker refers to a marker that has a nucleotide sequence that is the same (allowing for mutations introduced by the amplification reaction itself and/or naturally occurring and/or artificial alleleic differences) as an amplification product that is generated by amplifying *Zea mays* genomic DNA with a particular set of oligonucleotides. In some embodiments, the amplifying is by PCR, and the oligonucleotides are PCR primers that are designed to hybridize to opposite strands of the *Zea mays* genomic DNA in order to amplify a *Zea mays* genomic DNA sequence present between the sequences to which the PCR primers hybridize in the *Zea mays* genomic DNA. The amplified fragment that results from one or more rounds of amplification using such an arrangement of primers is a double stranded nucleic acid, one strand of which has a nucleotide sequence that comprises, in 5' to 3' order, the sequence of one of the primers, the sequence of the *Zea mays* genomic DNA located between the primers, and the reverse-complement of the second primer. Typically, the "forward" primer is assigned to be the primer that has the same sequence as a subsequence of the (arbitrarily assigned) "top" strand of a double-stranded nucleic acid to be amplified, such that the "top" strand of the amplified fragment includes a nucleotide sequence that is, in 5' to 3' direction, equal to the sequence of the forward primer—the sequence located between the forward and reverse primers of the top strand of the genomic fragment—the reverse-complement of the reverse primer. Accordingly, a marker that "corresponds to" an amplified fragment is a marker that has the same sequence of one of the strands of the amplified fragment.

Markers corresponding to genetic polymorphisms between members of a population can be detected by methods well-established in the art. These include, e.g., nucleic acid sequencing, hybridization methods, amplification methods (e.g., PCR-based sequence specific amplification methods), detection of restriction fragment length polymorphisms (RFLP), detection of isozyme markers, detection of polynucleotide polymorphisms by allele specific hybridization (ASH), detection of amplified variable sequences of the plant genome, detection of self-sustained sequence replication, detection of simple sequence repeats (SSRs), detection of single nucleotide polymorphisms (SNPs), and/or detection of amplified fragment length polymorphisms (AFLPs). Well established methods are also known for the detection of expressed sequence tags (ESTs) and SSR markers derived from EST sequences and randomly amplified polymorphic DNA (RAPD).

A "marker allele," also described as an "allele of a marker locus," can refer to one of a plurality of polymorphic nucleotide sequences found at a marker locus in a population that is polymorphic for the marker locus.

As used herein, the phrase "marker assay" refers to a method for detecting a polymorphism at a particular locus using a particular method such as but not limited to measurement of at least one phenotype (such as seed color, oil content, or a visually detectable trait); nucleic acid-based assays including, but not limited to restriction fragment length polymorphism (RFLP), single base extension, electrophoresis, sequence alignment, allelic specific oligonucleotide hybridization (ASO), random amplified polymorphic DNA (RAPD), microarray-based technologies, TAQMAN® Assays, ILLUMINA® GOLDENGATE® Assay analysis, nucleic acid sequencing technologies; peptide and/or polypeptide analyses; or any other technique that can be employed to detect a polymorphism in an organism at a locus of interest.

"Marker-assisted selection" (MAS) is a process by which phenotypes are selected based on marker genotypes.

"Marker-assisted counter-selection" is a process by which marker genotypes are used to identify plants that will not be selected, allowing them to be removed from a breeding program or planting.

As used herein, the terms "marker locus" and "marker loci" refer to a specific chromosome location or locations in the genome of an organism where a specific marker or markers can be found. A marker locus can be used to track the presence of a second linked locus, e.g., a linked locus that encodes or contributes to expression of a phenotypic trait. For example, a marker locus can be used to monitor segregation of alleles at a locus, such as a QTL or single gene, that are genetically or physically linked to the marker locus.

As used herein, the terms "marker probe" and "probe" refer to a nucleotide sequence or nucleic acid molecule that can be used to detect the presence of one or more particular alleles within a marker locus (e.g., a nucleic acid probe that is complementary to all of or a portion of the marker or marker locus, through nucleic acid hybridization). Marker probes comprising about 8, 10, 15, 20, 30, 40, 50, 60, 70, 80, 90, 100 or more contiguous nucleotides can be used for nucleic acid hybridization. Alternatively, in some aspects, a marker probe refers to a probe of any type that is able to distinguish (i.e., genotype) the particular allele that is present at a marker locus.

As used herein, the term "molecular marker" can be used to refer to a genetic marker, as defined above, or an encoded product thereof (e.g., a protein) used as a point of reference when identifying a linked locus. A molecular marker can be derived from genomic nucleotide sequences or from expressed nucleotide sequences (e.g., from a spliced RNA, a cDNA, etc.). The term also refers to nucleotide sequences complementary to or flanking the marker sequences, such as nucleotide sequences used as probes and/or primers capable of amplifying the marker sequence. Nucleotide sequences are "complementary" when they specifically hybridize in solution, e.g., according to Watson-Crick base pairing rules. Some of the markers described herein are also referred to as hybridization markers when located on an indel region. This is because the insertion region is, by definition, a polymorphism vis-à-vis a plant without the insertion. Thus, the marker need only indicate whether the indel region is present or absent. Any suitable marker detection technology can be used to identify such a hybridization marker, e.g., SNP technology is used in the examples provided herein.

A "non-naturally occurring variety of maize" is any variety of maize that does not naturally exist in nature. A "non-naturally occurring variety of maize" can be produced by any method known in the art, including, but not limited to, transforming a maize plant or germplasm, transfecting a maize plant or germplasm and crossing a naturally occurring variety of maize with a non-naturally occurring variety of maize. In some embodiments, a "non-naturally occurring variety of maize" can comprise one of more heterologous nucleotide sequences. In some embodiments, a "non-naturally occurring variety of maize" can comprise one or more non-naturally occurring copies of a naturally occurring nucleotide sequence (i.e., extraneous copies of a gene that naturally occurs in maize).

The "non-Stiff Stalk" heterotic group represents a major heterotic group in the northern U.S. and Canadian corn growing regions. It can also be referred to as the "Lancaster" or "Lancaster Sure Crop" heterotic group.

The "Stiff Stalk" heterotic group represents a major heterotic group in the northern U.S. and Canadian corn growing regions. It can also be referred to as the "Iowa Stiff Stalk Synthetic" or "BSSS" heterotic group.

As used herein, the term "percent barren" (PB) refers to the percentage of plants in a given area (e.g., plot) with no grain. It is typically expressed in terms of the percentage of plants per plot and can be calculated as:

$$\frac{\text{number of plants in the plot with no grain}}{\text{total number of plants in the plot}} \times 100$$

As used herein, the term "percent yield recovery" (PYREC) refers to the effect an allele and/or combination of alleles has on the yield of a plant grown under drought stress conditions as compared to that of a plant that is genetically identical except insofar as it lacks the allele and/or combination of alleles. PYREC is calculated as:

$$1 - \frac{\text{yield under full irrigation}(w/\text{allele}(s) \text{ of interest}) - \text{yield under drought conditions } (w/\text{allele}(s) \text{ of interest})}{\text{yield under full irrigation}(w/\text{out allele}(s) \text{ of interest}) - \text{yield under drought conditions } (w/\text{out allele}(s) \text{ of interest})} \times 100$$

By way of example and not limitation, if a control plant yields 200 bushels under full irrigation conditions, but yields only 100 bushels under drought stress conditions, then its percentage yield loss would be calculated at 50%. If an otherwise genetically identical hybrid that contains the allele(s) of interest yields 125 bushels under drought stress conditions and 200 bushels under full irrigation conditions, then the percentage yield loss would be calculated as 37.5% and the PYREC would be calculated as 25% [1.00−(200−125)/(200−100)×100)].

As used herein, the phrase "Grain Yield-Well Watered" refers to yield from an area that obtained enough irrigation to prevent plants from being water stressed during their growth cycle. In some embodiments, this trait is expressed in bushels per acre.

As used herein, the phrase "Yield Reduction-Hybrid" refers to a calculated trait obtained from a hybrid yield trial grown under stress and non-stress conditions. For a given hybrid, it equals:

$$\frac{\text{non-stress yield} - \text{yield under stress}}{\text{non-stressed yield}} \times 100.$$

In some embodiments, this trait is expressed as percent bushels per acre.

As used herein, the phrase "Yield Reduction-Inbred" refers to a calculated trait obtained from an inbred yield trial grown under stress and non-stress conditions. For a given inbred, it equals:

$$\frac{\text{non-stress yield} - \text{yield under stress}}{\text{non-stressed yield}} \times 100.$$

In some embodiments, this trait is expressed as percent bushels per acre.

As used herein, the phrase "Anthesis Silk Interval" (ASI) refers to the difference (in some embodiments, expressed in days) between when a plant starts shedding pollen (anthesis) and it starts producing silk (female). Data are collected on a per plot basis for anthesis and silking and the difference is calculated.

As used herein, the phrase "Percent Barren" refers to a percentage of plants in a given area (plot) with no grain. It is typically expressed in terms of % plants per plot and can be calculated as:

$$\frac{\text{Number of plant with no grain in a plot}}{\text{Total number of plants in the plot}} \times 100.$$

As used herein, the terms "phenotype," "phenotypic trait" or "trait" refer to one or more traits of an organism. The phenotype can be observable to the naked eye, or by any other means of evaluation known in the art, e.g., microscopy, biochemical analysis, or an electromechanical assay. In some cases, a phenotype is directly controlled by a single gene or genetic locus, i.e., a "single gene trait." In other cases, a phenotype is the result of several genes. It is noted that, as used herein, the term "water optimization phenotype" takes into account environmental conditions that might affect water optimization such that the water optimization effect is real and reproducible.

As used herein, the phrase "TAQMAN® Assay" refers to real-time sequence detection using PCR based on the TAQMAN® Assay sold by Applied Biosystems, Inc. of Foster City, Calif., United States of America. For an identified marker, a TAQMAN® Assay can be developed for application in a breeding program.

As used herein, the term "tester" refers to a line used in a testcross with one or more other lines wherein the tester and the line(s) tested are genetically dissimilar. A tester can be an isogenic line to the crossed line.

As used herein, the term "trait" refers to a phenotype of interest, a gene that contributes to a phenotype of interest, as well as a nucleic acid sequence associated with a gene that contributes to a phenotype of interest. For example, a "water optimization trait" refers to a water optimization phenotype as well as a gene that contributes to a water optimization phenotype and a nucleic acid sequence (e.g., an SNP or other marker) that is associated with a water optimization phenotype.

As used herein, the term "water optimization" refers to any measure of a plant, its parts, or its structure that can be measured and/or quantitated in order to assess an extent of or a rate of plant growth and development under conditions of sufficient water availability as compared to conditions of suboptimal water availability (e.g., drought). As such, a "water optimization trait" is any trait that can be shown to influence yield in a plant under different sets of growth conditions related to water availability.

Similarly, "water optimization" can be considered a "phenotype", which as used herein refers to a detectable, observable, and/or measurable characteristic of a cell or organism. In some embodiments, a phenotype is based at least in part on the genetic makeup of the cell or the organism (referred to herein as the cell or the organism's "genotype"). Exemplary water optimization phenotypes are grain yield at standard moisture percentage (YGSMN), grain moisture at harvest (GMSTP), grain weight per plot (GVVTPN), and percent yield recovery (PYREC). It is noted that as used herein, the term "phenotype" takes into account how the environment (e.g., environmental conditions) might affect water optimization such that the water optimization effect is real and reproducible. As used herein, the term "yield reduction" (YD) refers to the degree to which yield is reduced in plants grown under stress conditions. YD is calculated as:

$$\frac{\text{yield under non-stress conditions} - \text{yield under stress conditions}}{\text{yield under non-stress conditions}} \times 100$$

The terms "recombinant construct", "expression construct", "chimeric construct", "construct", and "recombinant DNA construct" are used interchangeably herein. A recombinant construct comprises an artificial combination of nucleic acid fragments, e.g., regulatory and coding sequences that are not found together in nature. For example, a chimeric construct may comprise regulatory sequences and coding sequences that are derived from different sources, or regulatory sequences and coding sequences derived from the same source, but arranged in a manner different than that found in nature. Such a construct may be used by itself or may be used in conjunction with a vector. If a vector is used, then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the invention. The skilled artisan will also recognize that different independent transformation events will result in different levels and patterns of expression (Jones et al. (1985) *EMBO J.* 4:2411-2418; De Almeida et al. (1989) *Mol. Gen. Genetics* 218:78-86), and thus that multiple events must be screened in order to obtain lines displaying the desired expression level and pattern. Such screening may be accomplished by Southern analysis of DNA, Northern analysis of mRNA expression, immunoblotting analysis of protein expression, or phenotypic analysis, among others.

This construct may comprise any combination of deoxyribonucleotides, ribonucleotides, and/or modified nucleotides. The construct may be transcribed to form an RNA, wherein the RNA may be capable of forming a double stranded RNA and/or hairpin structure. This construct may be expressed in the cell, isolated, or synthetically produced. The construct may further comprise a promoter, or other sequences that facilitate manipulation or expression of the construct.

As used herein, the terms "suppression", "silencing" or "inhibition" are used interchangeably to denote the down-regulation of the expression of a product of a target sequence relative to its normal expression level in a wild type organism. Suppression includes expression that is decreased by about 10%, 15%, 20%, 25%, 30%, 35%, 40%, 45%, 50%, 55%, 60%, 65%, 70%, 75%, 80%, 85%, 90%, 95%, or 100% relative to the wild type expression level.

As used herein, "encodes" or "encoding" refers to a DNA sequence that can be processed to generate an RNA and/or polypeptide.

As used herein, "expression" or "expressing" refers to production of a functional product, such as, the generation of an RNA transcript from an introduced construct, an endogenous DNA sequence, or a stably incorporated heterologous DNA sequence. The term may also refer to a polypeptide produced from an mRNA generated from any of the above DNA precursors. Thus, expression of a nucleic acid fragment may refer to transcription of the nucleic acid fragment (e.g., transcription resulting in mRNA or other functional RNA) and/or translation of RNA into a precursor or mature protein (polypeptide).

As used herein, "heterologous" with respect to a sequence means a sequence that originates from a foreign species, or, if from the same species, is substantially modified from its native form in composition and/or genomic locus by deliberate human intervention. For example, with respect to a nucleic acid, it can be a nucleic acid that originates from a foreign species, or is synthetically designed, or, if from the same species, is modified from its native form in composition and/or genomic locus by deliberate human intervention. In particular, the term heterologous, as used herein, includes single nucleotide polymorphisms that may be introduced into a host organism.

The term "host cell" refers to a cell that contains or into which is introduced a nucleic acid construct and supports the replication and/or expression of the construct. Host cells may be prokaryotic cells such as E. coli, or eukaryotic cells such as fungi, yeast, insect, amphibian, nematode, or mammalian cells. Alternatively, the host cells are monocotyledonous or dicotyledonous plant cells. An example of a monocotyledonous host cell is a maize host cell.

The term "introduced" means providing a nucleic acid (e.g., expression construct) or protein into a cell. Introduced includes reference to the incorporation of a nucleic acid into a eukaryotic or prokaryotic cell where the nucleic acid may be incorporated into the genome of the cell, and includes reference to the transient provision of a nucleic acid or protein to the cell. Introduced includes reference to stable or transient transformation methods, as well as sexually crossing. Thus, "introduced" in the context of inserting a nucleic acid fragment (e.g., a recombinant DNA construct/expression construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

The term "genome" as it applies to a plant cells encompasses not only chromosomal DNA found within the nucleus, but organelle DNA found within subcellular components (e.g., mitochondrial, plastid) of the cell.

The term "isolated" refers to material, such as a nucleic acid or a protein, which is: (1) substantially or essentially free from components which normally accompany or interact with the material as found in its naturally occurring environment or (2) if the material is in its natural environment, the material has been altered by deliberate human intervention to a composition and/or placed at a locus in the cell other than the locus native to the material.

As used herein, "microRNA" or "miRNA" refers to an oligoribonucleic acid, which base pairs to a polynucleotide comprising the target sequence causing post-transcriptional regulation by transcript degradation or translational suppression. A "mature miRNA" refers to the miRNA generated from the processing of a "precursor miRNA" or "pre-miRNA", which is the transcription product from a miRNA template. A "miRNA template" is an oligonucleotide region, or regions, in a nucleic acid construct that encodes the miRNA. The miRNA template may form a double-stranded polynucleotide, including a hairpin structure.

As used herein, "domain" or "functional domain" refers to nucleic acid sequence(s) that are capable of eliciting a biological response in plants. The present invention concerns miRNAs comprised of at least 21 nucleotide sequences acting individually or in concert with other miRNA sequences; therefore a domain could refer to either individual miRNAs or groups of miRNAs. miRNA sequences associated with their backbone sequences could be considered domains useful for processing the miRNA into its active form. As used herein, "subdomains" or "functional subdomains" refer to subsequences of domains that are capable of eliciting a biological response in plants. A miRNA could be considered a subdomain of a backbone sequence. "Contiguous" sequences or domains refer to sequences that are sequentially linked without added nucleotides intervening between the domains.

As used herein, the phrases "target sequence" and "sequence of interest" are used interchangeably. Target sequence is used to mean the nucleic acid sequence that is selected for alteration (e.g., suppression) of expression, and is not limited to polynucleotides encoding polypeptides. The target sequence comprises a sequence that is substantially or fully complementary to the miRNA. The target sequence includes, but is not limited to, RNA, DNA, or a polynucleotide comprising the target sequence. As discussed in Bartel and Bartel ((2003) Plant Phys. 132:709-719), most microRNA sequences are 20 to 22 nucleotides with anywhere from 0 to 3 mismatches when compared to their target sequences.

It is understood that microRNA sequences, such as the 21 nucleotide sequences of the present invention, may still be functional as shorter (20 nucleotide) or longer (22 nucleotide) sequences. In addition, some nucleotide substitutions, particularly at the last two nucleotides of the 3' end of the microRNA sequence, may be useful in retaining at least some microRNA function.

The terms "miRNA 169g," "miRNA 171a," and "miRNA 393" (or "miR169g," "miR171a," and "miR393") refer to the respective microRNAs from Zea mays and also encompass homologous and orthologous microRNAs in other plants. Homologous microRNAs include those with 70% or greater sequence homology to the above-noted miRNAs in Zea mays, for example, at least about 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%. Homologous and orthologous microRNAs will also share a similar chromosomal location.

As used herein, the term "polymorphism" refers to a variation in the nucleotide sequence at a locus, where said variation is too common to be due merely to a spontaneous mutation. A polymorphism must have a frequency of at least about 1% in a population. A polymorphism can be a single nucleotide polymorphism (SNP), or an insertion/deletion polymorphism, also referred to herein as an "indel." Additionally, the variation can be in a transcriptional profile or a methylation pattern. The polymorphic site or sites of a nucleotide sequence can be determined by comparing the nucleotide sequences at one or more loci in two or more germplasm entries. As used herein, the phrase "single nucleotide polymorphism", or "SNP", refers to a polymorphism that constitutes a single base pair difference between two nucleotide sequences. As used herein, the term "SNP" also refers to differences between two nucleotide sequences that result from simple alterations of one sequence in view of the other that occurs at a single site in the sequence. For example, the term "SNP" is intended to refer not just to sequences that differ in a single nucleotide as a result of a nucleic acid substitution in one versus the other, but is also intended to refer to sequences that differ in 1, 2, 3, or more nucleotides as a result of a deletion of 1, 2, 3, or more nucleotides at a single site in one of the sequences versus the other. It would be understood that in the case of two sequences that differ from each other only by virtue of a deletion of 1, 2, 3, or more nucleotides at a single site in one of the sequences versus the other, this same scenario can be considered an addition of 1, 2, 3, or more nucleotides at a single site in one of the sequences versus the other, depending on which of the two sequences is considered the reference sequence. Single site insertions and/or deletions are thus also considered to be encompassed by the term "SNP".

As used herein, the phrases "selected allele", "desired allele", and "allele of interest" are used interchangeably to refer to a nucleic acid sequence that includes a polymorphic allele associated with a desired trait. It is noted that a "selected allele", "desired allele", and/or "allele of interest" can be associated with either an increase in a desired trait or a decrease in a desired trait, depending on the nature of the phenotype sought to be generated in an introgressed plant.

As used herein, the term "primer" refers to an oligonucleotide which is capable of annealing to a nucleic acid target (in some embodiments, annealing specifically to a nucleic acid target) allowing a DNA polymerase to attach, thereby serving as a point of initiation of DNA synthesis when placed under conditions in which synthesis of a primer extension product is induced (e.g., in the presence of nucleotides and an agent for polymerization such as DNA polymerase and at a suitable temperature and pH). In some embodiments, a plurality of primers are employed to amplify Zea mays nucleic acids (e.g., using the polymerase chain reaction; PCR).

As used herein, the term "probe" refers to a nucleic acid (e.g., a single stranded nucleic acid or a strand of a double stranded or higher order nucleic acid, or a subsequence thereof) that can form a hydrogen-bonded duplex with a complementary sequence in a target nucleic acid sequence. Typically, a probe is of sufficient length to form a stable and sequence-specific duplex molecule with its complement, and as such can be employed in some embodiments to detect a sequence of interest present in a plurality of nucleic acids.

As used herein, the terms "progeny" and "progeny plant" refer to a plant generated from a vegetative or sexual reproduction from one or more parent plants. A progeny plant can be obtained by cloning or selfing a single parent plant, or by crossing two parental plants. Thus, the phrase "progeny plant" refers to any plant resulting as progeny from a vegetative or sexual reproduction from one or more parent plants or descendants thereof. For instance, a progeny plant can be obtained by cloning or selfing of a parent plant or by crossing two parental plants and include selfings as well as the F1 or F2 or still further generations. An F1 is a first-generation progeny produced from parents at least one of which is used for the first time as donor of a trait, while progeny of second generation (F2) or subsequent generations (F3, F4, and the like) are specimens produced from selfings, intercrosses, backcrosses, or other crosses of F1s, F2s, and the like. An F1 can thus be (and in some embodiments is) a hybrid resulting from a cross between two true breeding parents (i.e., parents that are true-breeding are each homozygous for a trait of interest or an allele thereof), while an F2 can be (and in some embodiments is) a progeny resulting from self-pollination of the F1 hybrids.

A "miRNA region" refers to sequences upstream, downstream, or within a miRNA template that contribute to folding or processing of the miRNA transcript or regulating transcription of the miRNA, i.e., features of the levels, spatial distribution, and/or temporal profile of the miRNA expression. Such miRNA regions can be identified, for example, based upon the presence of at least one single nucleotide polymorphism (SNP) or mutation that enhances or decreases transcript level of a mature miRNA.

As used herein, "nucleic acid" means a polynucleotide and includes single or double-stranded polymer of deoxyribonucleotide or ribonucleotide bases. Nucleic acids may also include fragments and modified nucleotides. Thus, the terms "polynucleotide", "nucleic acid sequence", "nucleotide sequence" or "nucleic acid fragment" are used interchangeably and refer to a polymer of RNA or DNA that is single- or double-stranded, optionally containing synthetic, non-natural or altered nucleotide bases. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

The term "nucleic acid library" is used to refer to a collection of isolated DNA or RNA molecules that comprise and substantially represent the entire transcribed fraction of a genome of a specified organism or of a tissue from that organism. Construction of exemplary nucleic acid libraries, such as genomic and cDNA libraries, is taught in standard molecular biology references (see, e.g., Berger and Kimmel, *Guide to Molecular Cloning Techniques, Methods in Enzymology*, Vol. 152, Academic Press, Inc., San Diego, Calif. (Berger); Sambrook et al., *Molecular Cloning–A Laboratory Manual*, 2nd ed., Vol. 1-3 (1989); and *Current Protocols in Molecular Biology*, F. M. Ausubel et al., Eds., Current Protocols, a joint venture between Greene Publishing Associates, Inc. and John Wiley & Sons, Inc. (1994).

As used herein "operably linked" includes reference to a functional linkage of at least two sequences. Operably linked includes linkage between a promoter and a second sequence, wherein the promoter sequence initiates and mediates transcription of the DNA sequence corresponding to the second sequence.

As used herein, "polypeptide" means proteins, protein fragments, modified proteins, amino acid sequences and synthetic amino acid sequences. The polypeptide can be glycosylated or not.

As used herein, "promoter" refers to a nucleic acid fragment, e.g., a region of DNA, that is involved in recognition and binding of an RNA polymerase and other proteins to initiate transcription. In other words, this nucleic acid fragment is capable of controlling transcription of another nucleic acid fragment.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, or 90% sequence identity, up to and including 100% sequence identity (i.e., fully complementary) with each other.

The term "stringent conditions" or "stringent hybridization conditions" includes reference to conditions under which a probe will selectively hybridize to its target sequence. Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length. Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA-DNA hybrids, the $T_m$ can be approximated from the equation of Meinkoth and Wahl, Anal. Biochem., 138:267-284 (1984): $T_m = 81.5°$ C. $+16.6$ (log M)$+0.41$ (% GC)$-0.61$ (% form)$-500/L$; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$ hybridization and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$ those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology-Hybridization with Nucleic Acid Probes*, Part I, Chapter 2 "Overview of principles of hybridization and the strategy of nucleic acid probe assays", Elsevier, New York (1993); and *Current Protocols in Molecular Biology*, Chapter 2, Ausubel et al., Eds., Greene Publishing and Wiley-Interscience, New York (1995). Hybridization and/or wash conditions can be applied for at least 10, 30, 60, 90, 120, or 240 minutes.

The terms "reliable detection" and "reliably detected" are defined herein to mean the reproducible detection of measurable, sequence-specific signal intensity above background noise.

As used herein, "transgenic" refers to a plant or a cell that comprises within its genome a heterologous polynucleotide. Preferably, the heterologous polynucleotide is stably integrated within the genome such that the polynucleotide is passed on, or heritable, to successive generations. The heterologous polynucleotide may be integrated into the genome alone or as part of an expression construct. Transgenic is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extrachromosomal) by conventional plant breeding methods or by naturally occurring events such as random cross-fertilization, non-recombinant viral infection, non-recombinant bacterial transformation, non-recombinant transposition, or spontaneous mutation.

As used herein, "vector" refers to a small nucleic acid molecule (plasmid, virus, bacteriophage, artificial or cut DNA molecule) that can be used to deliver a polynucleotide of the invention into a host cell. Vectors are capable of being replicated and contain cloning sites for introduction of a foreign polynucleotide. Thus, expression vectors permit transcription of a nucleic acid inserted therein.

Polynucleotide sequences may have substantial identity, substantial homology, or substantial complementarity to the selected region of the target gene. As used herein "substantial identity" and "substantial homology" indicate sequences that have sequence identity or homology to each other. Generally, sequences that are substantially identical or substantially homologous will have about 75%, 80%, 85%, 90%, 95%, or 100% sequence identity wherein the percent sequence identity is based on the entire sequence and is determined by GAP alignment using default parameters (GCG, GAP version 10, Accelrys, San Diego, Calif.). GAP uses the algorithm of Needleman and Wunsch (*Mol. Biol.* 48:443-453, 1970) to find the alignment of two complete sequences that maximizes the number of matches and minimizes the number of sequence gaps. Sequences which have 100% identity are identical. "Substantial complementarity" refers to sequences that are complementary to each other, and are able to base pair with each other. In describing complementary sequences, if all the nucleotides in the first sequence will base pair to the second sequence, these sequences are fully or completely complementary.

RNA interference refers to the process of sequence specific post-transcriptional gene silencing in animals mediated by short interfering RNAs (siRNAs) (Fire et al., *Nature* 391:806 1998). The corresponding process in plants is commonly referred to as post-transcriptional gene silencing (PTGS) or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla (Fire et al., *Trends Genet.* 15:358 1999). Such protection from foreign gene expression may have evolved in response to the production of double-stranded RNAs (dsRNAs) derived from viral infection or from the random integration of transposon elements into a host genome via a cellular response that specifically destroys homologous single-stranded RNA of viral genomic RNA. The presence of dsRNA in cells triggers the RNAi response through a mechanism that has yet to be fully characterized.

The presence of long dsRNAs in cells stimulates the activity of a ribonuclease III enzyme referred to as "dicer." Dicer is involved in the processing of the dsRNA into short pieces of dsRNA known as short interfering RNAs (siRNAs) (Berstein et al., *Nature* 409:363 2001) and/or pre miRNAs into miRNAs. Short interfering RNAs derived from dicer activity are typically about 21 to about 23 nucleotides in length and comprise about 19 base pair duplexes (Elbashir et al., *Genes Dev.* 15:188 2001). Dicer has also been implicated in the excision of 21- and 22-nucleotide small temporal RNAs (stRNAs) from precursor RNA of conserved structure that are implicated in translational control (Hutvagner et al., 2001, *Science* 293:834). The RNAi response also features an endonuclease complex, commonly referred to as an RNA-induced silencing complex (RISC), which mediates cleavage of single-stranded RNA having sequence complementarity to the antisense strand of the siRNA duplex. Cleavage of the target RNA takes place in the middle of the region complementary to the antisense strand of the siRNA duplex (Elbashir et al., *Genes Dev.* 15:188 2001). In addition, RNA interference can also involve small RNA (e.g., microRNA, or miRNA) mediated gene silencing, presumably through cellular mechanisms that regulate chromatin structure and thereby prevent transcription of target gene sequences (see, e.g., Allshire, *Science* 297:1818-1819 2002; Volpe et al., *Science* 297:1833-1837 2002; Jenuwein, *Science* 297:2215-2218 2002; and Hall et al., *Science* 297:2232-2237 2002). As such, miRNA molecules of the invention can be used to mediate gene silencing via interaction with RNA transcripts or alternately by interaction with particular gene sequences, wherein such interaction results in gene silencing either at the transcriptional or post-transcriptional level.

Small RNAs play an important role in controlling gene expression. Regulation of many developmental processes, including flowering, is controlled by small RNAs. It is now possible to engineer changes in gene expression of plant genes by using transgenic constructs that produce small RNAs in the plant.

Small RNAs function, at least in part, by base-pairing to complementary RNA or DNA target sequences. When bound to RNA, small RNAs trigger either RNA cleavage or translational inhibition of the target sequence. When bound to DNA target sequences, it is thought that small RNAs can mediate DNA methylation of the target sequence. The consequence of these events, regardless of the specific mechanism, is that gene expression is inhibited.

MicroRNAs (miRNAs) are noncoding RNAs of about 19 to about 24 nucleotides (nt) in length that have been identified in both animals and plants (Lagos-Quintana et al., *Science* 294:853-858 2001, Lagos-Quintana et al (2002) *Curr. Biol.* 12:735-739; Lau et al., (2001) *Science* 294:858-862; Lee and Ambros (2001) *Science* 294:862-864; Llave et al., *Plant Cell* 14:1605-1619 2002; Mourelatos et al., *Genes. Dev.* 16:720-728 2002; Park et al., (2002) *Curr. Biol.* 12:1484-1495; Reinhart et al (2002) *Genes. Dev.* 16:1616-1626). They are processed from longer precursor transcripts that range in size from approximately 70 to 200 nucleotides, and these precursor transcripts have the ability to form stable hairpin structures. Plants have an enzyme, DCL1, and evidence indicates that it is involved in processing the hairpin precursors to generate mature miRNAs (Park et al (2002) *Curr. Biol.* 12:1484-1495; Reinhart et al (2002) *Genes. Dev.* 16:1616-1626). Furthermore, at least some miRNA hairpin precursors originate as longer polyadenylated transcripts, and several different miRNAs and associated hairpins can be present in a single transcript (Lagos-Quintana et al (2001) *Science* 294:853-858; Lee et al., (2002) *EMBO J.* 21:4663-4670).

MicroRNAs regulate target genes, at least in part, by binding to complementary sequences located in the transcripts produced by these genes. In the case of lin-4 and let-7, the target sites are located in the 3' UTRs of the target mRNAs (Lee et al (1993) *Cell* 75:843-854; Wightman et al (1993) *Cell* 75:855-862; Reinhart et al (2000) *Nature* 403:901-906; Slack et al., *Mol. Cell.* 5:659-669 2000), and there are several mismatches between the lin-4 and let-7 miRNAs and their target sites. Some studies indicate that binding of the lin-4 or let-7 miRNA may downregulate steady-state levels of the protein encoded by the target mRNA without affecting the transcript itself (Olsen and Ambros, *Dev. Biol.* 216:671-680 1999). However, in some studies, miRNAs appear to cause specific RNA cleavage of the target transcript within the target site, and that this cleavage step requires 100% complementarity between the miRNA and the target transcript (Hutvagner and Zamore, (2002) *Science* 297:2056-2060; Llave et al., *Plant Cell* 14:1605-1619 2002). miRNAs may contribute to at least two pathways of target gene regulation: Protein downregulation when target complementarity is <100%, and RNA cleavage when target complementarity is 100%. MicroRNAs entering the RNA cleavage pathway are analogous to the 21-25 nucleotide short interfering RNAs (siRNAs) generated during RNA interference (RNAi) in animals and posttranscriptional gene silencing (PTGS) in plants (Hamilton and Baulcombe 1999; Hammond et al., 2000; Zamore et al., 2000; Elbashir et al., 2001), and are incorporated into an RNA-induced silencing complex (RISC) that is similar or identical to that seen for RNAi.

An aspect of the present invention is a method for identifying single nucleotide polymorphisms in miRNA regions using association mapping. Association mapping, including genome-wide association mapping and candidate-gene association mapping, has emerged as a tool to resolve complex trait variation down to the sequence level. Genome-wide association mapping is conducted to find signals of association for various complex traits by surveying genetic variation in the whole genome. Candidate-gene association mapping relates polymorphisms in selected candidate genes that could control phenotypic variation for specific traits. Association mapping relies on chromosomal recombination opportunities over a large number of generations, in the history of a species, which allows the removal of association between a QTL and any marker not tightly linked to it, thus improving the rate of discovery of true association (Jannink and Walsh, *Quantitative Genetics, Genomics and Plant Breeding*, Kang, Ed. CAB International, (2002) pp. 59-68).

An approach used to link phenotypic variation with genetic loci is marker-trait association (MTA) mapping, also known as linkage disequilibrium (LD) mapping. LD mapping emerged as an important gene mapping tool in early 1990's with the advent of high-throughput genotyping technology, and has been widely used in human genetics to identify genes affecting human diseases. This approach was introduced and began to be adopted in plant gene mapping studies in early 2000's (Flint-Garcia et al. (2003) *Annu Rev Plant Biol* 54: 357-374). In recent years, success in applying LD mapping has been seen in maize and other crops (Thornsberry et al. (2001) *Nat Genet* 28: 286-289).

LD mapping relies on linkage disequilibrium, which is defined as the non-random association of alleles from two different loci (genes or markers) in a natural population. LD mapping assumes that the main cause for LD is linkage that binds loci on the same chromosome together in transmission to next generation. However, due to recombination events accumulated over many generations in a natural population, each chromosome has been shuffled deeply, so that the chromosome has been broken into many tiny regions where loci remain transmitted together, but loci from different regions tend to transmit independently as if they were from different chromosomes. Chromosomal regions where loci are bound together in transmission are commonly known as LD blocks (Reich et al. (2001) *Nature* 411:199-204). LD mapping identifies genes of interest through genetic markers on the LD blocks where the genes are located. This is done by detecting significant associations between the markers and the traits that the genes affect with a sample of unrelated individuals or a sample of unrelated pedigrees that are genotyped on a selected set of markers covering candidate gene regions or the whole genome, and phenotyped on a set of traits of interest.

Compared with traditional linkage mapping methods that are typically based on artificial biparental segregating populations (e.g., F2, BC, DH, RIL, etc.), LD mapping generally produces better mapping resolution, because of the smaller sizes of LD blocks. In addition, LD mapping is useful in identifying more than two functional alleles at associated markers in a germplasm. Further, LD mapping is efficient for evaluating natural populations.

Linkage disequilibrium may be caused by factors other than linkage, such as mutation, migration, inbreeding, and genetic drift, inter alia. Consequently, LD mapping can be prone to false positives or spurious MTAs. Spurious MTAs are marker-trait associations between unlinked or distantly linked loci. Another consideration is the sample population structure. Population structure has been has been studied extensively, and effective statistical approaches have been developed to significantly reduce false positives in human genetics and in plants as well (Yu et al. (2006) *Nat. Genet.* 38:203-208). In addition, LD mapping requires high-density marker coverage on the genome in order to capture as many tiny LD blocks as possible. This issue has been largely overcome by high-throughput genotyping technology. However, other considerations in experimental design include precision and accuracy of phenotype acquisition in addition to throughput (Myles et al. (2009) *Plant Cell* 21:2194-2202).

Markers selected for association mapping are often chosen randomly with the goal of having the greatest number of markers spaced evenly across the genome. Another strategy, known as candidate gene strategy, is to make markers to score the alleles of genes that are suspected to influence the phenotype that one will evaluate. The present application discloses a third strategy (i.e., using markers to distinguish alleles of miRNAs that are associated with trait of interest). This third strategy has the advantage that miRNAs regulate many genes, and the genes they regulate often regulate many other genes. The advantages of this strategy are evident based on the findings provided herein: In an association study of 3072 random loci, 101 candidate gene loci and 3 microRNA loci, random loci showed 260 associations (8%), the candidate gene loci showed 41 associations (41%) and the miRNA loci had 3 associations (100%).

Another aspect of the invention is methods for suppressing a target sequence. The methods employ any constructs in which a miRNA is designed to identify a region of the target sequence, and inserted into the construct. One can selectively regulate the target sequence by encoding a miRNA having substantial complementarity to a region of the target sequence. The miRNA is provided in a nucleic acid construct which, when transcribed into RNA, is predicted to form a hairpin structure which is processed by the cell to generate the miRNA, which then suppresses expression of the target sequence. Upon introduction into a cell, the miRNA produced suppresses expression of the targeted sequence. The target sequence can be an endogenous plant sequence, or a heterologous transgene in the plant. In particular, the invention includes constructs comprising one or more of SEQ ID NOs: 1, 2, 3, 4, 5, 6, 7, 8, 9, or 10.

The methods provided can be practiced in any organism in which a method of transformation is available, and for which there is at least some sequence information for the target sequence, or for a region flanking the target sequence of interest. It is also understood that two or more sequences could be targeted by sequential transformation, co-transformation with more than one targeting vector, or the construction of a DNA construct comprising more than one miRNA sequence. The methods of the invention may also be implemented by a combinatorial nucleic acid library construction in order to generate a library of miRNAs directed to random target sequences. The library of miRNAs could be used for high-throughput screening for gene function validation.

General categories of sequences of interest include, for example, those genes involved in regulation or information, such as zinc fingers, transcription factors, homeotic genes, or cell cycle and cell death modulators, those involved in communication, such as kinases, and those involved in housekeeping, such as heat shock proteins. Other categories of target sequences include genes affecting agronomic traits, insect resistance, disease resistance, herbicide resistance, sterility, grain characteristics, and commercial products. Genes of interest also included those involved in oil, starch, carbohydrate, or nutrient metabolism as well as those affecting, for example, kernel size, sucrose loading, and the like. The quality of grain is reflected in traits such as levels and types of oils, saturated and unsaturated, quality, and quantity of essential amino acids, and levels of cellulose.

For example, genes of the phytic acid biosynthetic pathway could be suppressed to generate a high available phosphorous phenotype. See, for example, phytic acid biosynthetic enzymes including inositol polyphosphate kinase-2 polynucleotides, disclosed in PCT International Publication No. WO 02/059324, inositol 1,3,4-trisphosphate 5/6-kinase polynucleotides, disclosed in PCT International Publication No. WO 03/027243, and myo-inositol 1-phosphate synthase and other phytate biosynthetic polynucleotides, disclosed in PCT International Publication No. WO 99/05298. Genes in the lignification pathway could be suppressed to enhance digestibility or energy availability. Genes affecting cell cycle or cell death could be suppressed to affect growth or stress response. Genes affecting DNA repair and/or recombination could be suppressed to increase genetic variability. Genes affecting flowering time could be suppressed, as well as genes affecting fertility. Any target sequence could be suppressed in order to evaluate or confirm its role in a particular trait or phenotype, or to dissect a molecular, regulatory, biochemical, or proteomic pathway or network.

Target sequences further include coding regions and non-coding regions such as promoters, enhancers, terminators, introns and the like, which may be modified in order to alter the expression of a gene of interest. For example, an intron sequence can be added to the 5' region to increase the amount of mature message that accumulates (see, e.g., Buchman and Berg, (1988) *Mol. Cell. Biol.* 8:4395-4405; and Callis et al (1987) *Genes Dev.* 1:1183-1200).

The target sequence may be an endogenous sequence, or may be an introduced heterologous sequence, or transgene. For example, the methods may be used to alter the regulation or expression of a transgene, or to remove a transgene or other introduced sequence such as an introduced site-specific recombination site. The target sequence may also be a sequence from a pathogen, for example, the target sequence may be from a plant pathogen such as a virus, a mold or fungus, an insect, or a nematode. A miRNA could be expressed in a plant that, upon infection or infestation, would target the pathogen and confer some degree of resistance to the plant.

A number of promoters can be used, these promoters can be selected based on the desired outcome. It is recognized that different applications will be enhanced by the use of different promoters in plant expression cassettes to modulate the timing, location and/or level of expression of the miRNA. Such plant expression cassettes may also contain, if desired, a promoter regulatory region (e.g., one conferring inducible, constitutive, environmentally- or developmentally-regulated, or cell- or tissue-specific/selective expression), a transcription initiation start site, a ribosome binding site, an RNA processing signal, a transcription termination site, and/or a polyadenylation signal.

Constitutive, tissue-preferred or inducible promoters can be employed. Examples of constitutive promoters include the cauliflower mosaic virus (CaMV) 35S transcription initiation region, the 1'- or 2'-promoter derived from T-DNA of *Agrobacterium tumefaciens*, the ubiquitin 1 promoter, the Smas promoter, the cinnamyl alcohol dehydrogenase promoter (U.S. Pat. No. 5,683,439), the Nos promoter, the pEmu promoter, the rubisco promoter, the GRP1-8 promoter and other transcription initiation regions from various plant genes known to those of skill. If low level expression is desired, weak promoter(s) may be used. Weak constitutive promoters include, for example, the core promoter of the Rsyn7 promoter (PCT International Publication No. WO 99/43838 and U.S. Pat. No. 6,072,050), the core 35S CaMV promoter, and the like. Other constitutive promoters include, for example, U.S. Pat. Nos. 5,608,149; 5,608,144; 5,604,121; 5,569,597; 5,466,785; 5,399,680; 5,268,463; and 5,608,142. See also, U.S. Pat. No. 6,177,611.

Examples of inducible promoters are the Adhl promoter which is inducible by hypoxia or cold stress, the Hsp70 promoter which is inducible by heat stress, the PPDK promoter and the pepcarboxylase promoter which are both inducible by light. Also useful are promoters which are chemically inducible, such as the In2-2 promoter which is safener induced (U.S. Pat. No. 5,364,780), the ERE promoter which is estrogen induced, and the Axig1 promoter which is auxin induced and tapetum specific but also active in callus (PCT US01/22169).

Examples of promoters under developmental control include promoters that initiate transcription preferentially in certain tissues, such as leaves, roots, fruit, seeds, or flowers. An exemplary promoter is the anther specific promoter 5126 (U.S. Pat. Nos. 5,689,049 and 5,689,051). Examples of seed preferred promoters include, but are not limited to, 27 kD gamma zein promoter and waxy promoter, Boronat, A. et al. (1986) *Plant Sci.* 47:95-102; Reina, M. et al. *Nucl. Acids Res.* 18(21):6426; and Kloesgen, R. B. et al. (1986) *Mol. Gen. Genet.* 203:237-244. Promoters that express in the embryo, pericarp, and endosperm are disclosed in U.S. Pat. No. 6,225,529 and PCT International Publication No. WO 00/12733.

In some aspects it will be beneficial to express the gene from an inducible promoter, particularly from a pathogen-inducible promoter. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89:245-254; Uknes et al. (1992) *Plant Cell* 4:645-656; and Van Loon (1985) *Plant Mol. Virol.* 4:111-116. See also PCT International Publication No. WO 99/43819.

Of interest are promoters that are expressed locally at or near the site of pathogen infection. See, for example, Marineau et al. (1987) *Plant Mol. Biol.* 9:335-342; Matton et al. (1989) *Molecular Plant-Microbe Interactions* 2:325-331; Somsisch et al. (1986) *Proc. Natl. Acad. Sci. USA* 83:2427-2430; Somsisch et al. (1988) *Mol. Gen. Genet.* 2:93-98; and Yang (1996) *Proc. Natl. Acad. Sci. USA* 93:14972-14977. See also, Chen et al. (1996) *Plant J.* 10:955-966; Zhang et al. (1994) *Proc. Natl. Acad. Sci. USA* 91:2507-2511; Warner et al. (1993) *Plant J.* 3:191-201; Siebertz et al. (1989) *Plant Cell* 1:961-968; U.S. Pat. No. 5,750,386 (nematode-inducible); and the references cited therein. Of particular interest is the inducible promoter for the maize PRms gene, whose expression is induced by the pathogen *Fusarium moniliforme* (see, for example, Cordero et al. (1992) *Physiol. Mol. Plant. Path.* 41:189-200).

Additionally, as pathogens find entry into plants through wounds or insect damage, a wound-inducible promoter may be used in the constructions of the polynucleotides. Such wound-inducible promoters include potato proteinase inhibitor (pin II) gene (Ryan (1990) *Ann. Rev. Phytopath.* 28:425-449; Duan et al. (1996) *Nature Biotech.* 14:494-498); wun1 and wun2, U.S. Pat. No. 5,428,148; win1 and wing (Stanford et al. (1989) *Mol. Gen. Genet.* 215:200-208); systemin (McGurl et al. (1992) *Science* 225:1570-1573); WIP1 (Rohmeier et al. (1993) *Plant Mol. Biol.* 22:783-792; Eckelkamp et al. (1993) *FEBS Lett.* 323:73-76); MPI gene (Corderok et al. (1994) *Plant J.* 6(2):141-150.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1 a promoter, which is activated by salicylic acid. Other chemical-regulated promoters of interest include steroid steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156.

Tissue-preferred promoters can be utilized to target enhanced expression of a sequence of interest within a particular plant tissue. Tissue-preferred promoters include Yamamoto et al. (1997) *Plant J.* 12(2):255-265; Kawamata et al. (1997) *Plant Cell Physiol.* 38(7):792-803; Hansen et al. (1997) *Mol. Gen. Genet.* 254(3):337-343; Russell et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol. Biol.* 23(6):1129-1138; Matsuoka et al. (1993) *Proc Natl. Acad. Sci. USA* 90(20):9586-9590; and Guevara-Garcia et al. (1993) *Plant J.* 4(3):495-505. Such promoters can be modified, if necessary, for weak expression.

Leaf-preferred promoters are known in the art. See, e.g., Yamamoto et al. (1997) *Plant J.* 12(2):255-265; Kwon et al. (1994) *Plant Physiol.* 105:357-67; Yamamoto et al. (1994) *Plant Cell Physiol.* 35(5):773-778; Gotor et al. (1993) *Plant J.* 3:509-18; Orozco et al. (1993) *Plant Mol. Biol.* 23(6):1129-1138; and Matsuoka et al. (1993) *Proc. Natl. Acad. Sci. USA* 90(20):9586-9590. In addition, the promoters of cab and rubisco can also be used. See, e.g., Simpson et al. (1958) *EMBO J.* 4:2723-2729 and Timko et al. (1988) *Nature* 318:57-58.

Root-preferred promoters are known and can be selected from the many available from the literature or isolated de novo from various compatible species. See, for example, Hire et al. (1992) *Plant Mol. Biol.* 20(2):207-218 (soybean root-specific glutamine synthetase gene); Keller and Baumgartner (1991) *Plant Cell* 3(10):1051-1061 (root specific control element in the GRP 1.8 gene of French bean); Sanger et al. (1990) *Plant Mol. Biol.* 14(3):433-443 (root specific promoter of the mannopine synthase (MAS) gene of *Agrobacterium tumefaciens*); and Miao et al. (1991) *Plant Cell* 3(1):11-22 (full-length cDNA clone encoding cytosolic glutamine synthetase (GS), which is expressed in roots and root nodules of soybean). See also Bogusz et al. (1990) *Plant Cell* 2(7):633-641, where two root-specific promoters isolated from hemoglobin genes from the nitrogen-fixing non legume *Parasponia andersonii* and the related non-nitrogen fixing non legume *Trema tomentosa* are described. The promoters of these genes were linked to a 13-glucuronidase reporter gene and introduced into both the non legume *Nicotiana tabacum* and the legume *Lotus comiculatus*, and in both instances root-specific promoter activity was preserved. Leach and Aoyagi (1991) describe their analysis of the promoters of the highly expressed rolC and rolD root-inducing genes of *Agrobacterium rhizogenes* (see Plant Science (Limerick) 79(1):69-76). They concluded that enhancer and tissue-preferred DNA determinants are dissociated in those promoters. Teen et al. (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see *EMBO J.* 8(2): 343-350). The TR1' gene, fused to nptll (neomycin phosphotransferase II) showed similar characteristics. Additional root-preferred promoters include the VfENOD-GRP3 gene promoter (Kuster et al. (1995) *Plant Mol. Biol.* 29(4):759-772); and rolB promoter (Capana et al. (1994) *Plant Mol. Biol.* 25(4):681-691. See also U.S. Pat. Nos. 5,837,876; 5,750,386; 5,633,363; 5,459, 252; 5,401,836; 5,110,732; and 5,023,179. The phaseolin gene (Murai et al. (1983) *Science* 23:476-482 and Sengopta-Gopalen et al. (1988) *PNAS* 82:3320-3324.

Transformation protocols as well as protocols for introducing nucleotide sequences into plants may vary depending on the type of plant or plant cell, i.e., monocot or dicot, targeted for transformation. Suitable methods of introducing the DNA construct include microinjection (Crossway et al. (1986) *Biotechniques* 4:320-334; and U.S. Pat. No. 6,300, 543), sexual crossing, electroporation (Riggs et al. (1986) *Proc. Natl. Acad. Sci. USA* 83:5602-5606), Agrobacterium-mediated transformation (Townsend et al., U.S. Pat. Nos. 5,563,055; and 5,981,840), direct gene transfer (Paszkowski et al. (1984) *EMBO J.* 3:2717-2722), and ballistic particle acceleration (see, for example, Sanford et al., U.S. Pat. No. 4,945,050; Tomes et al., U.S. Pat. No. 5,879,918; Tomes et al., U.S. Pat. No. 5,886,244; Bidney et al., U.S. Pat. No. 5,932,782; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); and McCabe et al. (1988) *Biotechnology* 6:923-926). See also Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); Tomes, U.S. Pat. No. 5,240,855; Buising et al., U.S. Pat. Nos. 5,322,783 and 5,324,646; Klein et al. (1988) *Plant Physiol.* 91:440-444 (maize); Fromm et al. (1990) *Biotechnology* 8:833-839 (maize); Hooykaas-Van Slogteren et al. (1984) *Nature* (London) 311:763-764; Bowen et al., U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, N.Y.), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnol-* ogy 14:745-750 (maize via *Agrobacterium tumefaciens*); and U.S. Pat. No. 5,736,369 (meristem transformation).

The nucleotide constructs may be introduced into plants by contacting plants with a virus or viral nucleic acids. Generally, such methods involve incorporating a nucleotide construct of the invention within a viral DNA or RNA molecule. Further, it is recognized that useful promoters encompass promoters utilized for transcription by viral RNA polymerases. Methods for introducing nucleotide constructs into plants and expressing a protein encoded therein, involving viral DNA or RNA molecules, are known in the art. See, e.g., U.S. Pat. Nos. 5,889,191, 5,889,190, 5,866,785, 5,589,367 and 5,316,931.

DNA constructs containing miRNA genes and their corresponding upstream and downstream regulatory regions may be integrated of the into the host cell chromosome according to conventional methods, e.g., by homologous recombination or other methods of integration, including targeted integration at a particular host chromosomal site.

In some aspects, transient expression may be desired. In those cases, standard transient transformation techniques may be used. Such methods include, but are not limited to viral transformation methods, and microinjection of DNA or RNA, as well other methods well known in the art.

The cells from the plants that have stably incorporated the nucleotide sequence may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic imparted by the nucleotide sequence of interest and/or the genetic markers contained within the target site or transfer cassette. Two or more generations may be grown to ensure that expression of the desired phenotypic characteristic is stably maintained and inherited and then seeds harvested to ensure expression of the desired phenotypic characteristic has been achieved.

Initial identification and selection of cells and/or plants comprising the DNA constructs may be facilitated by the use of marker genes. Gene targeting can be performed without selection if there is a sensitive method for identifying recombinants, for example if the targeted gene modification can be easily detected by PCR analysis, or if it results in a certain phenotype. However, in most cases, identification of gene targeting events will be facilitated by the use of markers. Useful markers include positive and negative selectable markers as well as markers that facilitate screening, such as visual markers. Selectable markers include genes carrying resistance to an antibiotic such as spectinomycin (e.g. the aada gene, Svab et al. 1990 *Plant Mol. Biol.* 14:197), streptomycin (e.g., aada, or SPT, Svab et al. 1990 *Plant Mol. Biol.* 14:197; Jones et al. 1987 *Mol. Gen. Genet.* 210:86), kanamycin (e.g., nptII, Fraley et al. 1983 *PNAS* 80:4803), hygromycin (e.g., HPT, Vanden Elzen et al. 1985 *Plant Mol. Biol.* 5:299), gentamycin (Hayford et al. 1988 *Plant Physiol.* 86:1216), phleomycin, zeocin, or bleomycin (Hille et al. (1986) *Plant Mol. Biol.* 7:171), or resistance to a herbicide such as phosphinothricin (bar gene), or sulfonylurea (acetolactate synthase (ALS)) (Charest et al. (1990) *Plant Cell Rep.* 8:643), genes that fulfill a growth requirement on an incomplete media such as HIS3, LEU2, URA3, LYS2, and TRP1 genes in yeast, and other such genes known in the art. Negative selectable markers include cytosine deaminase (codA) (Stougaard (1993) *Plant J.* 3:755-761), tms2 (DePicker et al. (1988) *Plant Cell Rep.* 7:63-66), nitrate reductase (Nussame et al. (1991) *Plant J.* 1:267-274), SU1 (O'Keefe et al. (1994) *Plant Physiol.* 105:473-482), aux-2 from the Ti plasmid of *Agrobacterium*, and thymidine kinase. Screenable markers include fluorescent proteins such as green fluorescent protein (GFP) (Chalfie et al. (1994) *Science* 263:802; U.S. Pat. Nos. 6,146,826; 5,491,084; and PCT International Publication No. WO 97/41228), reporter enzymes such as 13-glucuronidase (GUS) (Jefferson R. A. (1987) *Plant Mol. Biol. Rep.* 5:387; U.S. Pat. Nos. 5,599,670; and 5,432,081), 13-galactosidase (lacZ), alkaline phosphatase (AP), glutathione S-transferase (GST) and luciferase (U.S. Pat. No. 5,674,713; and Ow et al. (1986) *Science* 234(4778):856-859), visual markers like anthocyanins such as CRC (Ludwig et al. (1990) *Science* 247(4841):449-450) R gene family (e.g., Lc, P, S), A, C, R-nj, body and/or eye color genes in *Drosophila*, coat color genes in mammalian systems, and others known in the art.

One or more markers may be used in order to select and screen for gene targeting events. One common strategy for gene disruption involves using a target modifying polynucleotide in which the target is disrupted by a promoterless selectable marker. Since the selectable marker lacks a promoter, random integration events generally do not lead to transcription of the gene. Gene targeting events will put the selectable marker under control of the promoter for the target gene. Gene targeting events are identified by selection for expression of the selectable marker. Another common strategy utilizes a positive-negative selection scheme. This scheme utilizes two selectable markers, one that confers resistance (R+) coupled with one that confers sensitivity (S+), each with a promoter. When this polynucleotide is randomly inserted, the resulting phenotype is R+/S+. When a gene targeting event is generated, the two markers are uncoupled and the resulting phenotype is R+/S−. Examples of using positive-negative selection are found in Thykjer et al. (1997) *Plant Mol. Biol.* 35:523-530; and PCT International Publication No. WO 01/66717.

Another aspect of the invention concerns a plant, cell, and seed comprising the construct and/or the miRNA. Typically, the cell will be a cell from a plant, but other prokaryotic or eukaryotic cells are also contemplated, including but not limited to viral, bacterial, yeast, insect, nematode, or animal cells. Plant cells include cells from monocots and dicots. The invention also provides plants and seeds comprising the construct and/or the miRNA.

EXAMPLES

The invention is now described with reference to the following Examples. These Examples are provided for the purpose of illustration only, and the invention is not limited to these Examples, but rather encompasses all variations that are evident as a result of the teachings provided herein.

Example 1

Identification and Analysis of SNP Diversity in miRNA Regulatory Regions of Three miRNAs from Inbred Maize Lines Genomic DNA amplicons containing the miR169g, miR171a, and miR393 regions and the upstream and downstream flanking sequences were amplified using the primers shown in Table 1 from a Maize genomic DNA library derived from a diverse panel of inbred lines. SNPs were identified by aligning the sequences from the Maize lines using SeqScape Software Version 2.5 from Applied Biosystems (FIGS. 1A-1P, 2A-2L, and 3A-3N).

TABLE 1

PCR Primers for B73 Maize miRNA Amplificaition

| Primer Name | F/R | SEQ ID | Sequence |
|---|---|---|---|
| 169gF1 | F | SEQ ID NO: 1 | 5'-ATGCAGCACAACGGTACAAG-3' |
| 169gR1 | R | SEQ ID NO: 2 | 5'-GCTGACTCCTCGGAGAAGAA-3' |
| 169gF2 | F | SEQ ID NO: 3 | 5'-AAAATCAGAGATGCAGCAGAA-3' |
| 169gR2 | R | SEQ ID NO: 4 | 5'-CTTTAAATAGTGGCGCGTGA-3' |
| 171F1 | F | SEQ ID NO: 5 | 5'-ATCGCCGTCGTTAAAACCTA-3' |
| 171R1 | R | SEQ ID NO: 6 | 5'-GATCCGATTGTCCTGCGTAT-3' |
| 393F1 | F | SEQ ID NO: 7 | 5'-GCTGCAGGCATATTCAATCC-3' |
| 393R1 | R | SEQ ID NO: 8 | 5'-CAGCCATCATCGTCATTCAC-3' |
| 393F2 | F | SEQ ID NO: 9 | 5'-ACGATGAGCGAAAGGAAAGA-3' |
| 393R2 | R | SEQ ID NO: 10 | 5'-GACCTCACATGACGCTTGTC-3' |

Example 2

Genotyping LD Mapping Panels

Using the putative SNPs identified in Example 1 as a guide, a TAQMAN® genotyping assay (Applied Biosystems) was developed to evaluate the prevalence of SNPs in the three miRNAs, miR171 and miR393 regions on approximately 700 base pair amplicons (Livak et al. (1995) *Nat. Genetics* 9:341-342). In allelic discrimination assays, a PCR assay includes a forward and reverse primer and a specific, fluorescent, dye-labeled probe for each of two alleles. The probes contain different fluorescent reporter dyes (VICO and FAM, or TET and FAM) to differentiate the amplification of each allele. FAM is 6-carboxyfluoroscein, TET is 6-carboxy-4,7,2',7'-tetrachlorofluorescein, and VICO is a proprietary dye (Applied Biosystems). A nonfluorescent quencher on each probe suppresses the fluorescence until amplification by PCR. During PCR, each probe anneals specifically to complementary sequences between the forward and reverse primer sites. Taq DNA polymerase then cleaves the probes that are hybridized to each allele. Cleavage separates the reporter dye from the quencher, which results in increased fluorescence by the reporter dye. Thus, the fluorescent signals generated by PCR amplification indicate that one or both alleles are present in the sample. In addition to the nonfluorescent quencher, the probe also contains a minor groove binder at the 3' end, which results in an increased melting temperature ($T_m$), thereby allowing high specificity with the use of shorter oligos. These probes therefore exhibit greater $T_m$ differences when hybridized to matched and mismatched templates, which provides more accurate allelic discrimination. Probes of this type can be manufactured at either ABI (MGB™ quencher) or Biosearch Technologies (BHQPLUS™ quencher). At the end of PCR thermal cycling, fluorescence of the two reporter dyes is measured on an ABI 7900 Sequence Detection System. An increase in fluorescence for one dye indicates homozygosity for the corresponding allele. Increase in both fluorescent signals indicates heterozygosity.

TABLE 2

TAQMAN ® Primers and Probes

| Primer Name | F/R | Start Pos. | SEQ ID | Primer or Prob Sequence (all are 5'→3') | Probe Fluorophore, Quencher, Groove Binder* |
|---|---|---|---|---|---|
| 169F2_169gR2-miRNA169g_127(1) | | | | | |
| SM1480DQF1 | F | 83 | SEQ ID NO: 11 | GAGATTGCGCGAATCAGTCA | — |
| SM1480DQR1 | R | 160 | SEQ ID NO: 12 | CTGCTGCATTTGCCGTTTATGAG | — |
| SM1480DQA1FM | F | 116 | SEQ ID NO: 13 | ACGTGTGGAGCCTTT | FAM, BHQ, BGB |
| SM1480DQA2TT | F | 116 | SEQ ID NO: 14 | ACGTGTGGAGCTTTTC | TET, BHQ, BGB |
| 169F2_169gR2-miRNA169g_213(1) | | | | | |
| SM1480BQF1 | F | 138 | SEQ ID NO: 15 | CTCATAAACGGCAAATGCAGCAG | — |
| SM1480BQR1 | R | 247 | SEQ ID NO: 16 | ACGCACGTCGGTCTACCACAT | — |

TABLE 2-continued

TAQMAN ® Primers and Probes

| Primer Name | F/R | Start Pos. | SEQ ID | Primer or Prob Sequence (all are 5'→3') | Probe Fluorophore, Quencher, Groove Binder* |
|---|---|---|---|---|---|
| SM1480BQA2TT | F | 198 | SEQ ID NO: 17 | TTGGTAATCAGTATCTGG | TET, BHQ, BGB |
| SM1480BQA1FM | F | 202 | SEQ ID NO: 18 | TAATCAGTATCCGGGAA | FAM, BHQ, BGB |
| 169F2_169gR2-miRNA169g_670(1) | | | | | |
| SM1480AQR1 | R | 712 | SEQ ID NO: 19 | ATGAGCCAGCTGATGA | — |
| SM1480AQF1 | F | 551 | SEQ ID NO: 20 | GAAGGCCTCTTCTTCTC | — |
| SM1480AQA1FM | R | 680 | SEQ ID NO: 21 | ACAGCCATACATACCT | FAM, BHQ, BGB |
| SM1480AQA2TT | R | 680 | SEQ ID NO: 22 | ACAGCCATACTTACCT | TET, BHQ, BGB |
| 171f1_171r1-miRNA171a_446(1) | | | | | |
| SM1479BQF1 | F | 382 | SEQ ID NO: 23 | TCCACCATAAGTTTACACACAGAG | — |
| SM1479BQR1 | R | 499 | SEQ ID NO: 24 | GGCACAGAGGGAGTATAATAGACA | — |
| SM1479BQA1FM | F | 435 | SEQ ID NO: 25 | AGGTTAGACCACTCGTT | FAM, BHQ, BGB |
| SM1479BQA2TT | F | 434 | SEQ ID NO: 26 | AAGGTTAGACCAGTCGTT | TET, BHQ, BGB |
| 393f2_393r2-miRNA393_152(1) | | | | | |
| SM1481AQF1 | F | 111 | SEQ ID NO: 27 | GCAACAGCCATCATCGTCATTC | — |
| SM1481AQR1 | R | 256 | SEQ ID NO: 28 | CAGCTGGGAGGAAGGGAAA | — |
| SM1481AQA1FM | F | 144 | SEQ ID NO: 29 | CCATCATCCTCGTCT | FAM, BHQ, BGB |
| SM1481AQA2TT | F | 144 | SEQ ID NO: 30 | CCATCATCGTCGTCT | TET, BHQ, BGB |
| 393f2_393r2-miRNA393_213(1) | | | | | |
| SM1481BQF1 | F | 0 | SEQ ID NO: 31 | CTGGGAGGAAGGGAAA | — |
| sM1481BQR1 | R | 0 | SEQ ID NO: 32 | ACAGCCATCATCGTCATTC | — |
| SM1481BQA2TT | F | 0 | SEQ ID NO: 33 | CGAGGTCGTAGCCA | TET, BHQ, BGB |
| SM1481BQA1FM | F | 0 | SEQ ID NO: 34 | CGAGGACGTAGCCA | FAM, BHQ, BGB |
| 393f2_393r2-miRNA393_629(1) | | | | | |
| SM1481CQF1 | F | 601 | SEQ ID NO: 35 | TCGCCTACTTGCTCTC | — |
| SM1481CQR1 | R | 724 | SEQ ID NO: 36 | GCTCCCATGAGCAAATTG | — |
| SM1481CQA2TT | F | 622 | SEQ ID NO: 37 | ACGTACTGGCTACATC | TET, BHQ, BGB |
| SM1481CQA1FM | F | 617 | SEQ ID NO: 38 | CACGTACGTACTAGCT | FAM, BHQ, BGB |
| 393f2_393r2-miRNA393_782(1) | | | | | |
| SM1481DQF1 | F | 0 | SEQ ID NO: 39 | GCAGACAAGTACAAACATAG | — |
| SM1481DQR1 | R | 0 | SEQ ID NO: 40 | ACGATGAGCGAAAGGAAA | — |
| SM1481DQA2TT | F | 0 | SEQ ID NO: 41 | AAATAGCTGCCGATTCAT | TET, BHQ, BGB |
| SM1481DQA1FM | F | 0 | SEQ ID NO: 42 | TAGCTGCCGATTAATTC | FAM, BHQ, BGB |

*FAM is 6-carboxyfluoroscein; TET is 6-carboxy-4,7,2',7'-tetrachlorofluoroscein; BHQ is Black Hole Plus QUENCHER ®; BGB is BioSource Groove Binder To validate TAQMAN® allelic discrimination assays for association with drought tolerance, plants were selected based on their known phenotypic status and compared to the genotype at the specific SNP location. DNA was extracted from leaf tissue of seedlings 7-10 days after planting. DNA can be extracted from plant tissue in a variety of ways, including the CTAB method, sodium hydroxide, and the Dellaporta method. DNA is diluted in TE buffer (10 mM Tris. HCl, pH 7.5, 1 mM EDTA) and stored at 4° C. until used in PCR reactions. PCR reactions were set up in 5 μL final volumes according to Table 3.

TABLE 3

TAQMAN ® PCR Conditions

| Reagent | Stock concentration | For each 5 μL reaction (μL) | For 96 samples (μL) | Final concentration |
|---|---|---|---|---|
| 2x Master Mix* | 2x | 2.5 | 296.88 | 1x |
| Primer/probe mixture (80x) | 40x | 0.0625 | 6.0 | 0.5x |
| PCR-quality H$_2$O | — | 2.44 | 234.24 | — |
| DNA (dried in 384 plate) | 4.5 ng/μL | 4.0 | — | 3.6 ng/μL (18 ng) |
| Final Volume (μL) | — | 5.00 | 357.44 | — |

*The Master Mix is JUMPSTART ™ Taq READYMIX ™, a premix of all the components (except primers and probes), including nucleotides and Taq DNA polymerase, necessary to perform a 5' nuclease assay. Before use 1375 mL of M$_g$Cl$_2$ (and 250 mL of sulforhodamine 101 were added to a 125 mL bottle of JUMPSTART ™.

PCR plates were placed in ABI 9700 Thermal cyclers and the following thermocycle programs were run.

TABLE 4

TAQMAN ® Thermocycle Programs

| Task | SNP1 |
|---|---|
| Initial denaturation | 50° C. for 2 min. |
| — | 95° C. for 10 min. |
| Cycles | 95° C. for 15 sec. |
| — | 60° C. for 1 min. |
| Number of cycles | 40 |
| Final elongation | 72° C. for 5 min. |
| Hold at 4° C. | Indefinite |

The ABI 7900 Sequence Detection System, or "TAQMAN®" was used to visualize the results of an allelic discrimination SNP assay. Using the Sequence Detection System (SDS, Applied Biosystems) software, allele calls were determined based on the fluorescence for the two dyes measured in each sample. Table 5 shows the SNP positions and allele types for amplicons 169g, 393, and 171a.

TABLE 5

| Marker | Amplicon | SNP position on amplicon | Allele Types |
|---|---|---|---|
| SM1480DQ | 169 g | 174 | C:T |
| SM1480BQ | 169 g | 259 | C:T |
| SM1480AQ | 169 g | 701 | A:T |
| SM1481AQ | 393 | 179 | C:G |
| SM1481BQ | 393 | 251 | A:T |
| SM1481CQ | 393 | 608 | A:G |
| SM1481DQ | 393 | 726 | A:G |
| SM1479AQ | 171a | 505 | C:T |
| SM1479BQ | 171a | 561 | C:G |

TABLE 6 is the summary of haplotypes observed in plants and the number of occurrences.

| Locus | Num | Code | SNPs Alleles | SNPs Order | Haploty pe Freq (#) |
|---|---|---|---|---|---|
| miRNA171 | | | | | |
| SM1479 | 1 | A | T:C | SM1479AQ:SM1479BQ | 698 |
| SM1479 | 2 | B | T:G | SM1479AQ:SM1479BQ | 267 |
| SM1479 | 3 | C | C:C | SM1479AQ:SM1479BQ | 51 |
| SM1479 | 4 | D | C:G | SM1479AQ:SM1479BQ | 79 |
| | | | | Total | 1095 |
| miRNA393 | | | | | |
| SM1481 | 1 | A | C:A:A:A | SM1481AQ:SM1481BQ:SM1481CQ:SM1481DQ | 189 |
| SM1481 | 2 | B | C:A:A:G | SM1481AQ:SM1481BQ:SM1481CQ:SM1481DQ | 136 |
| SM1481 | 3 | C | C:A:G:G | SM1481AQ:SM1481BQ:SM1481CQ:SM1481DQ | 440 |
| SM1481 | 4 | D | C:T:A:A | SM1481AQ:SM1481BQ:SM1481CQ:SM1481DQ | 12 |
| SM1481 | 5 | E | C:T:G:G | SM1481AQ:SM1481BQ:SM1481CQ:SM1481DQ | 2 |
| SM1481 | 6 | F | G:T:A:A | SM1481AQ:SM1481BQ:SM1481CQ:SM1481DQ | 1 |
| SM1481 | 7 | G | G:T:A:G | SM1481AQ:SM1481BQ:SM1481CQ:SM1481DQ | 149 |
| | | | | Total | 929 |
| miRNA169 | | | | | |
| SM1480 | 1 | A | A:C:C | SM1480AQ:SM1480BQ:SM1480DQ | 3 |
| SM1480 | 2 | B | A:C:T | SM1480AQ:SM1480BQ:SM1480DQ | 654 |
| SM1480 | 3 | C | T:C:T | SM1480AQ:SM1480BQ:SM1480DQ | 79 |
| SM1480 | 4 | D | T:T:T | SM1480AQ:SM1480BQ:SM1480DQ | 328 |
| | | | | Total | 1064 |

Example 3

Marker-Trait Association Analysis of miRNAs from Inbred and Hybrid Maize

An association mapping study begins with development of a population sample, continues with genotyping and phenotyping all individuals in the sample, and ends with data analysis and result summary. The population sample is a set of unrelated individuals (with no known pedigree relationships), which is called the linkage disequilibrium (LD) panel, or a set of unrelated pedigrees (Cardon and Bell (2001) *Nat. Rev. Genet.* 2:91-99). An association study needs to make many strategic decisions around the population sample, genetic markers, genotyping platform, experimental design (e.g. treatments, locations and repetitions) for phenotyping with field trials, and the choice of appropriate statistical procedure and methods. The reliability and applicability of MTA results from the study depend heavily on the size and composition of the population sample, genomic coverage of genetic markers (candidate-genes based or genome-wide), precision of genotyping and phenotyping, and appropriate use of statistical procedure and methods.

The population samples used in this study were from two commercially establish LD panels of diverse inbred lines, an inbred maize panel and a hybrid maize panel. The hybrid panel further consisted of two subpanels: the non-stiff stalk (NSS) panel and the stiff stalk (SS) panel, while the inbred panel is a mixture of both SS and NSS inbreds. NSS and SS are the two main targeted heterotic groups in maize. The inbred panel and both hybrid subpanels each consisted of approximately 600 inbred lines selected from a platform of 2,075 inbreds that represent the wide genetic diversity and maturity groups (early, intermediate, and late) in the maize germplasm.

The inbred panel was genotyped and phenotyped directly using the inbred panel lines. The hybrid panel was genotyped on the inbred panel as well, and phenotyping was conducted on the hybrids of the inbred panel with a commercially important inbred as the tester. The combination of phenotypic data on both inbreds and hybrids was intended to study the effects of genetic backgrounds (homozygous and heterozygous) on MTAs.

The two LD panels were each phenotyped in one year at multiple locations. Two water treatments were assessed; normal irrigation (WET) and flowering-time drought stress (DRY) were conducted with both panels. These experiments assessed the effects of MTAs on yield and drought tolerance under different irrigation conditions.

After phenotyping, WET and DRY treatments were applied to the inbred maize panel. The first location had 5 repetitions for DRY treatment and 2 repetitions for WET treatment, while the second location had 6 DRY repetitions and 3 WET repetitions. The arrangement of the repetitions in the field was based on maturity groups (early, intermediate, and late) to control for field differences.

After phenotyping, each subpanel of the hybrid maize panel (SS or NSS) was grown at 5 locations with WET treatment, and 3 locations with DRY treatment. Three repetitions were applied for WET treatment, and 6 repetitions for DRY treatment, at all locations where the treatment was applied.

The field trials were specially selected as managed stress environments to permit effective water treatments, in particular the DRY treatment. In these trials, the use of more DRY repetitions reduced the standard errors in phenotypic observations under drought conditions.

A total of ~30 yield and physiological/morphological traits were directly observed and/or calculated for the two LD panels. However, the trait sets used for each panel were very different. The inbred panel was typed using more traits, including yield and its components, several physiological/morphological traits, and drought response traits. By comparision, no yield component traits or drought response traits were typed with hybrid panel. The focus of the hybrid panel was on yield productivity, while the inbred panel was examined to identify novel genes acting on agronomic traits.

There were two purposes for phenotypic data analysis: data quality control (QC) and phenotypic adjustment for fitting association statistical models. The procedure for analyzing the phenotypic data on the hybrid panel is shown in the flowchart in FIG. 4. The phenotypic data were split, according to various experimental conditions, in order to detect MTAs that might be caused by various types of gene by environment interactions. 938 lines (434 NSS, 504 SS) were phenotyped for 13 trait in DRY and WET conditions. Data splitting was carried out prior to phenotypic adjustment for model fitting. It was intended to subset the cleaned data according to various experimental conditions including water treatments. Data for each split was then analyzed separately to detect MTAs under particular experimental conditions to capture effects from G×E and G×G interactions.

Six splits were created for the inbred panel data, three for each location, including two splits for DRY and WET and one split combining data from the two treatments. Data splitting for the hybrid panel was much more complicated, which split the data for water treatments, location groups, LD panels, and important combinations between water treatments and panels. In total, there were 83 splits for the hybrid panel. Note that location groups for the hybrid panel were determined based on similarity among locations in maize growing environments and trait responses using genotype main effect plus genotype by environment interaction (GGE) biplot analysis. In order to fit the statistical models for association analysis, split-specific phenotypic adjustment was done to remove all non-genetic effects (or design-of-experiment (DOE) effects), including effects from locations, repetitions, LD panels, water treatments, etc., depending on the data split in question. At the end of this process, a breeding value or overall genetic effect for each trait was calculated for each inbred in the split.

Example 4

Evaluation of Phenotypic Adjustment

Phenotypic data adjustment is a necessary step for fitting the GLM/MLM association models. However, phenotypic adjustment was conducted with MLM, which relies on a few statistical assumptions, including independency between fitted values and random residuals, and normal distribution for random residuals. Violation of these assumptions would affect the reliability and accuracy of the final MTA results (p values, etc.). Therefore, it was important to determine the quality (model fitness) of the adjusted phenotypic data, so that the MTA results from the adjusted data would not be over-interpreted.

After adjusting phenotypic data, two plots were also outputted from phenotypic adjustment for each data split. The first plot fitted values against model residuals, which shows the independency between fitted values and residuals. The second plot was a QQ plot, which indicates normality of the distribution. A 3-level scoring method was used to visually evaluate the quality of the adjusted data. For good-level data, there was a roughly rectangle distribution of data points, suggesting a good independency of residual distribution from fitted values. Furthermore, the data points were mostly on the diagonal line of the QQ plot, which is expected for normal residuals. For bad-level fitness, both plots showed large deviation from the expected values, and third level fitness was in between the good and bad levels.

With this scoring system, all of the eleven main data splits for the hybrid LD panel were assessed. Grain moisture traits (GMSAP and GMSTP) and grain yield traits (YGSMN, YGSAN, YGSMN/GMSTP, and YGSAN/GMSAP) all had per acre less than those with the "A" allele at harvest moisture percentage. This relationship between grain moisture percentage and grain yield at harvest moisture percentage is typical.

TABLE 7

| Trait | Marker | Allele Types | Allele Freqs | Eff_Alle | Alle_Eff |
|---|---|---|---|---|---|
| GMSAP | SM1480AQ | A:T | 0.5744:0.4256 | T | −0.44 |
| GMSTP | SM1480AQ | A:T | 0.5744:0.4256 | T | −0.51 |
| YGHMN | SM1479AQ | T:C | 0.8765:0.1235 | C | −4.02 |
| SLK5N | SM1480AQ | A:T | 0.5744:0.4256 | T | −0.01 |
| YGSAN | SM1479AQ | T:C | 0.8765:0.1235 | C | −2.11 |
| YGSAN/GMSAP | SM1480AQ | A:T | 0.5744:0.4256 | T | 0.147 |
| YGSMN | SM1479AQ | T:C | 0.8765:0.1235 | C | −2.94 |
| ERHTN | SM1479BQ | C:G | 0.7108:0.2892 | G | 1.445 |
| ERHTN | SM1480BQ | T:C | 0.3371:0.6629 | T | 1.589 |
| GMSAP | SM1481DQ | A:G | 0.1709:0.8291 | G | 0.239 |
| GMSTP | SM1481DQ | A:G | 0.1709:0.8291 | G | 0.281 |
| PLHTN | SM1481CQ | A:G | 0.5428:0.4572 | G | 1.615 |
| SLK5N | SM1480BQ | T:C | 0.3371:0.6629 | T | 0.041 |
| YGSAN/GMSAP | SM1479BQ | C:G | 0.7108:0.2892 | G | −0.11 |
| YGSAN/GMSAP | SM1480BQ | T:C | 0.3371:0.6629 | T | 0.111 |
| YGSMN/GMSTP | SM1479BQ | C:G | 0.7108:0.2892 | G | −0.13 |
| YGSMN/GMSTP | SM1480AQ | A:T | 0.5744:0.4256 | T | 0.15 |
| POL5N | SM1480AQ | A:T | 0.5744:0.4256 | T | 0.021 |
| POL5N | SM1480BQ | T:C | 0.3371:0.6629 | T | 0.056 |
| POL5N | SM1481DQ | A:G | 0.1709:0.8291 | G | 0.084 |
| SLK5N | SM1481DQ | A:G | 0.1709:0.8291 | G | 0.117 |
| YGHMN | SM1480AQ | A:T | 0.5744:0.4256 | T | −0.9 |
| YGHAN | SM1481DQ | A:G | 0.1709:0.8291 | G | 1.661 |
| YGHMn | SM1481DQ | A:G | 0.1709:0.8291 | G | 2.124 |

| Trait Code | Unit | Trait Name |
|---|---|---|
| ERHTN | centimeter | Ear Height in cm |
| PLHTN | centimeter | Plant Height |
| YGHMN | bushels per acre | Grain Yield at Harvest Moisture Percentage |
| YGSMN | bushels per acre | Grain Yield at Standard Moisture Percentage |
| ASIDN | day | Anthesis-Silk Interval in Days |
| GMSAP | percentage | Grain Moisture Adjusted Percentage |
| GMSTP | percentage | Grain Moisture at Harvest |
| POL5N | day | Days to 50% plants pollen |
| SLK5N | day | Days to 50% plants silk |
| YGSAN | bushels per acre | Yield Grain Adjusted at Standard Moisture |
| YGHAN | bushels per acre | Yield Grain Adjusted at Harvest Moisture |
| YGSAN/GMSAP | percent | ratio of YGSAN to GMSAP |
| YGSMN/GMSTP | percent | ratio of YGSMN to GMSTP | good model fitness in phenotypic adjustment. However, two yield traits unadjusted for standard moisture (YGHMN and YGHAN) did not have very good fitness in phenotypic adjustment. Morphological traits (ERHTN and PLHTN), and flowering time traits (SLK5N, ASIDN, and POL5N) had fair model fitness. In addition, four traits (BRRNN, STD_N, STKLN, and STKLP) had bad fitness in all the relevant data splits. These traits were not analyzed with GLM/MLM for associations. Table 7 shows the effect of a single allele on a particular plant trait for 24 MTAs that passed Bonferroni correction cutoff threshold in hybrid panel.

Looking at the first row of Table 7 and cross-referencing Table 5, one can see that the SNP at position 701 of the 169g amplicon (i.e., marker SM1480AQ) is associated with grain moisture adjusted percentage (GMSAP). Specifically, plants with the "T" allele have 0.44% less moisture at harvest. Plants possessing this allele are therefore more desirable than those with the "A" allele, as grain stores better at lower moisture percentage.

In a similar fashion, looking at the third row from the bottom of Table 7, one also sees that that the "T" allele is also associated with grain yield at harvest moisture percentage. Specifically, plants with the "T" allele yield 0.9 bushels Table 8 is similar to Table 7, but cross-references Table 6 and shows the effect of haplotype on a particular plant trait. For example, looking at row 23, one sees that marker SM1480 is associated with grain moisture adjusted percentage (GMSAP), consistent with the first row of Table 7 discussed above. As shown in Table 7, four combinations of alleles (out of eight possible) in the SM1480 marker are present in the 1064 plants examined. The most frequent haplotype resulting in this favorable phenotype is the "C" haplotype (i.e., a "T" at position 174 of the 169g amplicon, a "C" at position 259 of the 169g amplicon, and a "T" at position 701 of the 169g amplicon), while the most frequent haplotype resulting in an unfavorable phenotype is the "A" haplotype (i.e., a "A" at position 174 of the 169g amplicon, a "C" at position 259 of the 169g amplicon, and a "C" at position 701 of the 169g amplicon). The effect of the "C" haplotype on grain moisture adjusted percentage ranges from 0.84279 to 1.5428 and the mean is 1.18, meaning that plants having these variant alleles have 1.18% less moisture at harvest (which is desirable for the reasons described above).

TABLE 8

| No. | miRNA | Trait | Marker | Most Freq Fav Combo | Most Freq Unfav Combo | Allele Effect Range (GLM) | Mean Allele Effect (GLM) |
|---|---|---|---|---|---|---|---|
| 1 | miRNA | ASIDN | SM1481 | A | B | 0.41 | 0.41 |
| 2 | 393 | DERNR | SM1481 | B | F | 1.5527 | 1.55 |
| 3 | | DSFLR2 | SM1481 | D | F | 0.8656 | 0.87 |
| 4 | | EARPN | SM1481 | F | G | 0.9183 | 0.92 |
| 5 | | ERHTN | SM1481 | E | F | 10.64-15.93 | 13.28 |
| 6 | | GMSAP | SM1481 | A | D | 1.79-2.03 | 1.91 |
| 7 | | GMSTP | SM1481 | A | D | 1.99-2.13 | 2.06 |
| 8 | | KEPEN | SM1481 | F | G | 172.8882 | 172.89 |
| 9 | | KEPPL | SM1481 | F | A | 240.549 | 240.55 |
| 10 | | KRRWN | SM1481 | F | A | 2.44-6.02 | 4.23 |
| 11 | | PLHTN | SM1481 | G | E | 17.63-20.16 | 18.89 |
| 12 | | POL5N | SM1481 | A | E | 0.35-2.48 | 1.86 |
| 13 | | SLK5N | SM1481 | A | E | 0.66-2.05 | 1.45 |
| 14 | | YGhMN | SM1481 | B | A | 10.26 | 10.26 |
| 15 | | YGSAN/ GMSAP | SM1481 | A | D | 0.79 | 0.79 |
| 16 | | YGSMN | SM1481 | F | C | 6.17 | 6.17 |
| 17 | | YGSMN/ GMSTP | SM1481 | A | D | 0.81 | 0.81 |
| 18 | miRNA | BRRNP | SM1480 | B | D | 0.057 | 0.06 |
| 19 | 169 | DSFLR2 | SM1480 | A | D | 0.6178 | 0.62 |
| 20 | | DSFLR3 | SM1480 | C | A | 0.5707 | 0.57 |
| 21 | | EARPN | SM1480 | D | A | 0.1712 | 0.17 |
| 22 | | ERHTN | SM1480 | D | A | 2.711-6.3184 | 4.39 |
| 23 | | GMSAP | SM1480 | C | A | 0.84279-1.5428 | 1.18 |
| 24 | | GMSTP | SM1480 | C | A | 0.96-2.1841 | 1.41 |
| 25 | | KRLNN | SM1480 | D | C | 0.6891 | 0.69 |
| 26 | | POL5N | SM1480 | A | D | 1.05 | 1.05 |
| 27 | | SLK5N | SM1480 | A | D | 1.42 | 1.42 |
| 28 | | YGHAN | SM1480 | B | C | 5.98 | 5.98 |
| 29 | | YGhMN | SM1480 | B | C | 9.09 | 9.09 |
| 30 | | YGSAN | SM1480 | B | C | 3.07 | 3.07 |
| 31 | | YGSAN/ GMSAP | SM1480 | C | A | 0.47-0.79 | 0.65 |
| 32 | | YGSMN | SM1480 | B | C | 5.38-18.74 | 12.06 |
| 33 | | YGSMN/ GMSTP | SM1480 | C | A | 0.71-0.86 | 0.79 |
| 34 | miRNA | ASIDN | SM1479 | C | B | 0.097-0.102 | 0.10 |
| 35 | 171 | ERHTN | SM1479 | B | C | 1.74-4.27 | 2.75 |
| 36 | | GMSAP | SM1479 | C | B | 0.84-1.26 | 0.97 |
| 37 | | GMSTP | SM1479 | C | B | 0.98-1.26 | 1.16 |
| 38 | | KRRWN | SM1479 | B | C | 0.1608-0.6392 | 0.40 |
| 39 | | PLHTN | SM1479 | D | B | 2.13-4.27 | 3.16 |
| 40 | | SLK5N | SM1479 | C | B | 0.40-0.51 | 0.46 |
| 41 | | YGHAN | SM1479 | B | C | 3.98-6.40 | 5.19 |
| 42 | | YGhMN | SM1479 | A | C | 4.99-5.68 | 5.26 |
| 43 | | YGSAN | SM1479 | A | D | 2.49-3.92 | 3.20 |
| 44 | | YGSAN/ GMSAP | SM1479 | C | D | 0.18-0.30 | 0.71 |
| 45 | | YGSMN | SM1479 | A | D | 3.51-4.72 | 4.11 |
| 46 | | YGSMN/ GMSTP | SM1479 | C | D | 0.21-0.32 | 0.27 |

The disclosure of every patent, patent application, and publication cited herein is hereby incorporated herein by reference in its entirety.

While this invention has been disclosed with reference to specific embodiments, it is apparent that other embodiments and variations of this invention can be devised by others skilled in the art without departing from the true spirit and scope of the invention. The appended claims include all such embodiments and equivalent variations.

What is claimed is:

1. A method of producing a maize plant using marker-assisted breeding, wherein said maize plant exhibits increased grain yield at standard moisture percentage, the method comprising the steps of:
    (a) crossing a first maize plant or a progeny thereof with a second maize plant, wherein said first maize plant or progeny thereof has been selected for said crossing based on the presence of
        (a1) at least one polymorphism within a marker locus of its genome, wherein said marker locus is associated with increased grain yield at standard moisture percentage and wherein said marker locus is SEQ ID NO: 84 and
        (a2) at least one single nucleotide polymorphism located at a nucleotide corresponding to a position selected from the group consisting of:
            (i) position 444 of SEQ ID NO: 69, wherein the nucleotide is a C, and
            (ii) position 500 of SEQ ID NO: 69, wherein the nucleotide is a C;
    (b) producing a progeny plant population from the cross of (a);
    (c) selecting a progeny plant from the progeny plant population of (b) based on genotyping the progeny plant's genomic DNA and selecting a progeny plant having the at least one polymorphism of (a1) and the at least one polymorphism of (a2) said marker locus; and
    (d) producing a maize plant using marker-assisted breeding wherein said maize plant exhibits increased grain yield at standard moisture percentage.

2. The method of claim 1, wherein the at least one single nucleotide polymorphism of (a1) is located in a pre-miRNA portion of the microRNA region.

3. The method of claim 2, wherein the pre-miRNA portion of the microRNA region comprises SEQ ID NO: 82.

4. The method of claim 2, wherein the pre-miRNA portion of the microRNA region comprises SEQ ID NO: 83.

5. The method of claim 1, wherein the at least one single nucleotide polymorphism of (a1) is located in a mature miRNA portion of the microRNA region.

6. The method of claim 5, wherein the mature miRNA portion of the microRNA region comprises SEQ ID NO: 82.

7. A method of selecting a maize plant having enhanced drought tolerance, the method comprising:
    (a) isolating a nucleic acid from a maize plant cell;
    (b) detecting in the nucleic acid of (a) the presence of
        (a1) at least one single nucleotide polymorphism in a microRNA region comprising SEQ ID NO: 84 and (a2) at least one single nucleotide polymorphism located at a nucleotide corresponding to a position selected from the group consisting of:
            (i) position 444 of SEQ ID NO: 69, wherein the nucleotide is a C, and
            (ii) position 500 of SEQ ID NO: 69, wherein the nucleotide is a C, thereby identifying a maize plant having enhanced drought tolerance;
    (c) crossing the maize plant of (b) with a maize plant not having the polymorphisms of (a1) and (a2); and
    (d) growing progeny from (c) to produce a plant having the polymorphisms.

8. The method of claim 7, wherein the at least one single nucleotide polymorphism of (a1) is located in a pre-miRNA portion of the microRNA region.

9. The method of claim 8, wherein pre-miRNA portion of the microRNA region comprises SEQ ID NO: 82.

10. The method of claim 8, wherein pre-miRNA portion of the microRNA region comprises SEQ ID NO: 83.

11. The method of claim 7, wherein the at least one single nucleotide polymorphism of (a1) is located in a mature miRNA portion of the microRNA region.

12. The method of claim 11, wherein the mature miRNA portion of the microRNA region comprises SEQ ID NO: 82.

* * * * *

SEQUENCE LISTING

<160> NUMBER OF SEQ ID NOS: 111

<210> SEQ ID NO 1
<211> LENGTH: 20
<212> TYPE: DNA
<213> ORGANISM: Artificial
<220> FEATURE:
<223> OTHER INFORMATION: PCR Primer

<400> SEQUENCE: 1

-continued atgcagcaca acggtacaag                                          20

<210> SEQ ID NO 2
<211> LENGTH: 20
<212> TYPE: DNA
<213> ORGANISM: Artificial
<220> FEATURE:
<223> OTHER INFORMATION: PCR Primer

<400> SEQUENCE: 2
gctgactcct cggagaagaa                                          20

<210> SEQ ID NO 3
<211> LENGTH: 21
<212> TYPE: DNA
<213> ORGANISM: Artificial
<220> FEATURE:
<223> OTHER INFORMATION: PCR Primer

<400> SEQUENCE: 3
aaaatcagag atgcagcaga a                                        21

<210> SEQ ID NO 4
<211> LENGTH: 20
<212> TYPE: DNA
<213> ORGANISM: Artificial
<220> FEATURE:
<223> OTHER INFORMATION: PCR Primer

<400> SEQUENCE: 4
ctttaaatag tggcgcgtga                                          20

<210> SEQ ID NO 5
<211> LENGTH: 20
<212> TYPE: DNA
<213> ORGANISM: Artificial
<220> FEATURE:
<223> OTHER INFORMATION: PCR Primer

<400> SEQUENCE: 5
atcgccgtcg ttaaaaccta                                          20

<210> SEQ ID NO 6
<211> LENGTH: 20
<212> TYPE: DNA
<213> ORGANISM: Artificial
<220> FEATURE:
<223> OTHER INFORMATION: PCR Primer

<400> SEQUENCE: 6
gatccgattg tcctgcgtat                                          20

<210> SEQ ID NO 7
<211> LENGTH: 20
<212> TYPE: DNA
<213> ORGANISM: Artificial
<220> FEATURE:
<223> OTHER INFORMATION: PCR Primer

<400> SEQUENCE: 7
gctgcaggca tattcaatcc                                          20

<210> SEQ ID NO 8
<211> LENGTH: 20
<212> TYPE: DNA

<213> ORGANISM: Artificial
<220> FEATURE:
<223> OTHER INFORMATION: PCR Primer

<400> SEQUENCE: 8
cagccatcat cgtcattcac                                              20

<210> SEQ ID NO 9
<211> LENGTH: 20
<212> TYPE: DNA
<213> ORGANISM: Artificial
<220> FEATURE:
<223> OTHER INFORMATION: PCR Primer

<400> SEQUENCE: 9
acgatgagcg aaaggaaaga                                              20

<210> SEQ ID NO 10
<211> LENGTH: 20
<212> TYPE: DNA
<213> ORGANISM: Artificial
<220> FEATURE:
<223> OTHER INFORMATION: PCR Primer

<400> SEQUENCE: 10
gacctcacat gacgcttgtc                                              20

<210> SEQ ID NO 11
<211> LENGTH: 20
<212> TYPE: DNA
<213> ORGANISM: Artificial
<220> FEATURE:
<223> OTHER INFORMATION: Taqman Primer

<400> SEQUENCE: 11
gagattgcgc gaatcagtca                                              20

<210> SEQ ID NO 12
<211> LENGTH: 23
<212> TYPE: DNA
<213> ORGANISM: Artificial
<220> FEATURE:
<223> OTHER INFORMATION: Taqman Primer

<400> SEQUENCE: 12
ctgctgcatt tgccgtttat gag                                          23

<210> SEQ ID NO 13
<211> LENGTH: 15
<212> TYPE: DNA
<213> ORGANISM: Artificial
<220> FEATURE:
<223> OTHER INFORMATION: Taqman Probe

<400> SEQUENCE: 13
acgtgtggag cctttt                                                  15

<210> SEQ ID NO 14
<211> LENGTH: 16
<212> TYPE: DNA
<213> ORGANISM: Artificial
<220> FEATURE:
<223> OTHER INFORMATION: Taqman Probe

<400> SEQUENCE: 14
acgtgtggag cttttc                                                  16

```
<210> SEQ ID NO 15
<211> LENGTH: 23
<212> TYPE: DNA
<213> ORGANISM: Artificial
<220> FEATURE:
<223> OTHER INFORMATION: Taqman Primer

<400> SEQUENCE: 15
ctcataaacg gcaaatgcag cag                                              23

<210> SEQ ID NO 16
<211> LENGTH: 21
<212> TYPE: DNA
<213> ORGANISM: Artificial
<220> FEATURE:
<223> OTHER INFORMATION: Taqman Primer

<400> SEQUENCE: 16
acgcacgtcg gtctaccaca t                                                21

<210> SEQ ID NO 17
<211> LENGTH: 18
<212> TYPE: DNA
<213> ORGANISM: Artificial
<220> FEATURE:
<223> OTHER INFORMATION: Taqman Probe

<400> SEQUENCE: 17
ttggtaatca gtatctgg                                                    18

<210> SEQ ID NO 18
<211> LENGTH: 17
<212> TYPE: DNA
<213> ORGANISM: Artificial
<220> FEATURE:
<223> OTHER INFORMATION: Taqman Probe

<400> SEQUENCE: 18
taatcagtat ccgggaa                                                     17

<210> SEQ ID NO 19
<211> LENGTH: 16
<212> TYPE: DNA
<213> ORGANISM: Artificial
<220> FEATURE:
<223> OTHER INFORMATION: Taqman Primer

<400> SEQUENCE: 19
atgagccagc tgatga                                                      16

<210> SEQ ID NO 20
<211> LENGTH: 17
<212> TYPE: DNA
<213> ORGANISM: Artificial
<220> FEATURE:
<223> OTHER INFORMATION: Taqman Primer

<400> SEQUENCE: 20
gaaggcctct tcttctc                                                     17

<210> SEQ ID NO 21
<211> LENGTH: 16
<212> TYPE: DNA
<213> ORGANISM: Artificial
<220> FEATURE:
```

```
<223> OTHER INFORMATION: Taqman Probe

<400> SEQUENCE: 21
acagccatac atacct                                                      16

<210> SEQ ID NO 22
<211> LENGTH: 16
<212> TYPE: DNA
<213> ORGANISM: Artificial
<220> FEATURE:
<223> OTHER INFORMATION: Taqman Probe

<400> SEQUENCE: 22
acagccatac ttacct                                                      16

<210> SEQ ID NO 23
<211> LENGTH: 24
<212> TYPE: DNA
<213> ORGANISM: Artificial
<220> FEATURE:
<223> OTHER INFORMATION: Taqman Primer

<400> SEQUENCE: 23
tccaccataa gtttacacac agag                                             24

<210> SEQ ID NO 24
<211> LENGTH: 24
<212> TYPE: DNA
<213> ORGANISM: Artificial
<220> FEATURE:
<223> OTHER INFORMATION: Taqman Primer

<400> SEQUENCE: 24
ggcacagagg gagtataata gaca                                             24

<210> SEQ ID NO 25
<211> LENGTH: 17
<212> TYPE: DNA
<213> ORGANISM: Artificial
<220> FEATURE:
<223> OTHER INFORMATION: Taqman Probe

<400> SEQUENCE: 25
aggttagacc actcgtt                                                     17

<210> SEQ ID NO 26
<211> LENGTH: 18
<212> TYPE: DNA
<213> ORGANISM: Artificial
<220> FEATURE:
<223> OTHER INFORMATION: Taqman Probe

<400> SEQUENCE: 26
aaggttagac cagtcgtt                                                    18

<210> SEQ ID NO 27
<211> LENGTH: 22
<212> TYPE: DNA
<213> ORGANISM: Artificial
<220> FEATURE:
<223> OTHER INFORMATION: Taqman Primer

<400> SEQUENCE: 27
gcaacagcca tcatcgtcat tc                                               22
```

```
<210> SEQ ID NO 28
<211> LENGTH: 19
<212> TYPE: DNA
<213> ORGANISM: Artificial
<220> FEATURE:
<223> OTHER INFORMATION: Taqman Primer

<400> SEQUENCE: 28
cagctgggag gaagggaaa                                                  19

<210> SEQ ID NO 29
<211> LENGTH: 15
<212> TYPE: DNA
<213> ORGANISM: Artificial
<220> FEATURE:
<223> OTHER INFORMATION: Taqman Probe

<400> SEQUENCE: 29
ccatcatcct cgtct                                                      15

<210> SEQ ID NO 30
<211> LENGTH: 15
<212> TYPE: DNA
<213> ORGANISM: Artificial
<220> FEATURE:
<223> OTHER INFORMATION: Taqman Probe

<400> SEQUENCE: 30
ccatcatcgt cgtct                                                      15

<210> SEQ ID NO 31
<211> LENGTH: 16
<212> TYPE: DNA
<213> ORGANISM: Artificial
<220> FEATURE:
<223> OTHER INFORMATION: Taqman Primer

<400> SEQUENCE: 31
ctgggaggaa gggaaa                                                     16

<210> SEQ ID NO 32
<211> LENGTH: 19
<212> TYPE: DNA
<213> ORGANISM: Artificial
<220> FEATURE:
<223> OTHER INFORMATION: Taqman Primer

<400> SEQUENCE: 32
acagccatca tcgtcattc                                                  19

<210> SEQ ID NO 33
<211> LENGTH: 14
<212> TYPE: DNA
<213> ORGANISM: Artificial
<220> FEATURE:
<223> OTHER INFORMATION: Taqman Probe

<400> SEQUENCE: 33
cgaggtcgta gcca                                                       14

<210> SEQ ID NO 34
<211> LENGTH: 14
<212> TYPE: DNA
<213> ORGANISM: Artificial
<220> FEATURE:
<223> OTHER INFORMATION: Taqman Probe
```

```
<400> SEQUENCE: 34
cgaggacgta gcca                                                    14

<210> SEQ ID NO 35
<211> LENGTH: 16
<212> TYPE: DNA
<213> ORGANISM: Artificial
<220> FEATURE:
<223> OTHER INFORMATION: Taqman Primer

<400> SEQUENCE: 35
tcgcctactt gctctc                                                  16

<210> SEQ ID NO 36
<211> LENGTH: 18
<212> TYPE: DNA
<213> ORGANISM: Artificial
<220> FEATURE:
<223> OTHER INFORMATION: Taqman Primer

<400> SEQUENCE: 36
gctcccatga gcaaattg                                                18

<210> SEQ ID NO 37
<211> LENGTH: 16
<212> TYPE: DNA
<213> ORGANISM: Artificial
<220> FEATURE:
<223> OTHER INFORMATION: Taqman Probe

<400> SEQUENCE: 37
acgtactggc tacatc                                                  16

<210> SEQ ID NO 38
<211> LENGTH: 16
<212> TYPE: DNA
<213> ORGANISM: Artificial
<220> FEATURE:
<223> OTHER INFORMATION: Taqman Probe

<400> SEQUENCE: 38
cacgtacgta ctagct                                                  16

<210> SEQ ID NO 39
<211> LENGTH: 20
<212> TYPE: DNA
<213> ORGANISM: Artificial
<220> FEATURE:
<223> OTHER INFORMATION: Taqman Primer

<400> SEQUENCE: 39
gcagacaagt acaaacatag                                              20

<210> SEQ ID NO 40
<211> LENGTH: 18
<212> TYPE: DNA
<213> ORGANISM: Artificial
<220> FEATURE:
<223> OTHER INFORMATION: Taqman Primer

<400> SEQUENCE: 40
acgatgagcg aaaggaaa                                                18

<210> SEQ ID NO 41
<211> LENGTH: 18
```

```
<212> TYPE: DNA
<213> ORGANISM: Artificial
<220> FEATURE:
<223> OTHER INFORMATION: Taqman Probe

<400> SEQUENCE: 41
aaatagctgc cgattcat                                                        18

<210> SEQ ID NO 42
<211> LENGTH: 17
<212> TYPE: DNA
<213> ORGANISM: Artificial
<220> FEATURE:
<223> OTHER INFORMATION: Taqman Probe

<400> SEQUENCE: 42
tagctgccga ttaattc                                                         17

<210> SEQ ID NO 43
<211> LENGTH: 22
<212> TYPE: DNA
<213> ORGANISM: Zea mays

<400> SEQUENCE: 43
tagccaagga tgacttgcct ac                                                   22

<210> SEQ ID NO 44
<211> LENGTH: 140
<212> TYPE: DNA
<213> ORGANISM: Zea mays

<400> SEQUENCE: 44
cagagctagc ctgcctctgg tagccaagga tgacttgcct acatggtctc gctagttccg          60
gttgttgcat gcatgccact atgccagtcc tgctgggttt gtgggcggtc tccttggcta         120
gcctgagtgg ctcttgcctg                                                    140

<210> SEQ ID NO 45
<211> LENGTH: 815
<212> TYPE: DNA
<213> ORGANISM: Zea mays

<400> SEQUENCE: 45
tatgcatgag gtcaaactca attttgaggg aacaaaaaac gactttaaat agtggcgcgt          60
gacgctgact cctcgcagaa gaatcgtcag cgaccccaga gcagggcagg gagtccttcc         120
tcccaccagc tagctagcga tactactatc caaagagaat atggagagat ttccctgaga         180
ttgcgcgaat cagtcactgc acgtacgtgt ggagcttttc tgttttctca taaacggcaa         240
atgcagcagc aggaggcttt gggtattttt attttctctc aacgattggt aatcagtatc         300
tgggaaagct gtggatgtgg tagaccgacg tgcgttgagt cggcatcgtc cggttcatcc         360
tatgtattcc ctttcctgct ataaataccg gccgggccga gggtgtcgaa gccgcagatc         420
aatgcatggc cgcgcgccgg cgccggtagg gatggaggag gaggaagaag aggcggcctt         480
gcatgagggc cagagctagc ctgcctctgg tagccaagga tgacttgcct acatggtctc         540
gctagttccg gttgttgcat gcatgccact atgccagtcc tgctgggttt gtgggcggtc         600
tccttggcta gcctgagtgg ctcttgcctg tcatggaagg cctcttcttc tctgccacgt         660
actctcgcct agctagtcgc cttatggtac gtaccgtctg cctcagtggc tctggcctgt         720
gcttcgttgg gtttgccagg taagtatggc tgtcgttcat tgctgattca tcagctggct         780
```
catatatatg taatgctgca tgcaacgcta atatc    815

<210> SEQ ID NO 46
<211> LENGTH: 775
<212> TYPE: DNA
<213> ORGANISM: Zea mays

<400> SEQUENCE: 46
acgaattcct tcctcccacc agctagctag cgatactact atccaaagag aatatggaga    60
gatttccctg agattgcgcg aatcagtcac tgcacgtacg tgtggagctt ttctgttttc    120
tcataaacgg caaatgcagc agcaggaggc tttgggtatt tttattttct ctcaacgatt    180
ggtaatcagt atccgggaaa gctgtggatg tggtagaccg acgtgcgttg agtcggcatc    240
gtccggttca tcctatgtat tccctttcct gctataaata ccggccgggc cgagggtgtc    300
gaagccgcag atcaatgcat ggccgccggc gccggtaggg atgaggagg aggaggaaga    360
agaggcggcc ttgcatgagg ccagagcta gcctgcctct ggtagccaag gatgacttgc    420
ctacatggtc tcgctagttc cggttgttgc atgcatgcca ctatgccagt cctgctgggt    480
ttgtgggcgg tctccttggc tagcctgagt ggctcttgcc tgtcatggaa ggcctcttct    540
tctctgccac gtactctcgc ctagctagtc gcctatggt acgtaccgtc tgcctcagtg    600
gctctggcct gtgcttcgtt gggtttgcca ggtaagtatg ctgtcgttc attgctgatt    660
catcagctgg ctcatatata tgtaatgctg catgcaacgc taatatcgtt ttcttaatta    720
ttttgttatt acctgtgcgt gcttgcagat tgttctgaat tctgaaatgt atggg    775

<210> SEQ ID NO 47
<211> LENGTH: 768
<212> TYPE: DNA
<213> ORGANISM: Zea mays

<400> SEQUENCE: 47
acgaattcct tcctcccacc agctagctag cgatactact atccaaagag aatatggaga    60
gatttccctg agattgcgcg aatcagtcac tgcactgcac gtacgtgtgg agcttttctg    120
ttttctcata aacggcaaat gcagcagcag gaggctttgg gtatttttat tttctctcaa    180
cgattggtaa tcagtatccg ggaaagctgt ggatgtggta gaccgacgtg cgttgagtcg    240
gcatcgtccg gttcatccta tgtattccct tcctgctat aaataccggc cgggccgagg    300
gtgtcgaagc cgcagatcaa tgcatggccg ccggcgccgg tagggatgga ggaggaggag    360
gaagaagagg cggccttgca tgagggccag agctagcctg cctctggtag ccaaggatga    420
cttgcctaca tggtctcgct agttccggtt gttgcatgca tgccactatg ccagtcctgc    480
tgggtttgtg ggcggtctcc ttggctagcc tgagtggctc ttgcctgtca tggaaggcct    540
cttcttctct gccacgtact ctcgcctagc tagtcgcctt atggtacgta ccgtctgcct    600
cagtggctct ggcctgtgct tcgttgggtt tgccaggtaa gtatgctgt cgttcattgc    660
tgattcatca gctggctcat atatgtaa tgctgcatgc aacgctaata tcgttttctt    720
aattatttg ttattacctg tgcgtgcttg cagattgttc tgaattct    768

<210> SEQ ID NO 48
<211> LENGTH: 742
<212> TYPE: DNA
<213> ORGANISM: Zea mays

<400> SEQUENCE: 48
caccagctag ctagcgatac tactatccaa agagaatatg gagagatttc cctgagattg    60

```
cgcgaatcag tcactgcact gcacgtacgt gtggagcttt tctgttttct cataaacggc    120
aaatgcagca gcaggaggct ttgggtattt ttatttttctc tcaacgattg gtaatcagta    180
tccgggaaag ctgtggatgt ggtagaccga cgtgcgttga gtcggcatcg tccggttcat    240
cctatgtatt ccctttcctg ctataaatac cggccgggcc gagggtgtcg aagccgcaga    300
tcaatgcatg gccgccggcg ccggtaggga tggaggagga ggaggaagaa gaggcggcct    360
tgcatgaggg ccagagctag cctgcctctg gtagccaagg atgacttgcc tacatggtct    420
cgctagttcc ggttgttgca tgcatgatgc atggccagtc ctgctgggtt tgtgggcggt    480
ctccttggct agcctgagtg gctcttgcct gtcatggaag gcctcttctt ctctgccacg    540
tacactcgcc tagctagtcg ccttatatgg tacgtaccgt cgtctgcctc tggcggcctg    600
tgcttcgttt ggtttgccag gtatgtatgg ctgttcaatt cattggtgat tcatcagctg    660
gctcatatat atgtaatgct gcatgcaacg ctaatattgt tttcttaatt attttgttat    720
tacctgtgcc ggcttgcaga tt                                             742

<210> SEQ ID NO 49
<211> LENGTH: 782
<212> TYPE: DNA
<213> ORGANISM: Zea mays

<400> SEQUENCE: 49
acgaattcct tcctcccacc agctagctag cgatactact atccaaagag aatatggaga    60
gatttccctg agattgcgcg aatcagtcac tgcactgcac gtacgtgtgg agcttttctg    120
ttttctcata aacggcaaat gcmgcagcag gaggctttgg gtatttttat tttctctcaa    180
cgattggtaa tcagtatccg ggaaagctgt ggatgtggta gaccgacgtg cgttgagtcg    240
gcatcgtccg gttcatccta tgtattccct ttcctgctat aaataccggc cgggccgagg    300
gtgtcgaagc gcagatcaa tgcatggccg ccggcgccgg tagggatgga ggaggaggag    360
gaagaagagg cggccttgca tgagggccag agctagcctg cctctggtag ccaaggatga    420
cttgcctaca tggtctcgct agttccggtt gttgcatgca tgatgcatgg ccagtcctgc    480
tgggtttgtg ggcggtctcc ttggctagcc tgagtggctc ttgcctgtca tggaaggcct    540
cttcttctct gccacgtaca ctcgcctagc tagtcgcctt atatggtacg taccgtcgtc    600
tgcctctggc ggcctgtgct tcgtttggtt tgccaggtat gtatggctgt tcaattcatt    660
ggtgattcat cagctggctc atatatatgt aatgctgcat gcaacgctaa tattgttttc    720
ttaattattt tgttattacc tgtgccggct tgcrgatwgt tctgaattct gaaatgtatg    780
gg                                                                   782

<210> SEQ ID NO 50
<211> LENGTH: 775
<212> TYPE: DNA
<213> ORGANISM: Zea mays

<400> SEQUENCE: 50
cagggcaggg agtccttcct cccaccagct agcgatacta ctatccaaag agaatatgga    60
gagatttccc tgagattgcg cgaatcagtc actgcacgta cgtgtggagc ttttctgttt    120
tctcataaac ggcaaatgca gcagcaggag ctttgggta tttttatttt ctctcaacga    180
ttggtaatca gtatccggga aagctgtgga tgtggtagac cgacgtgcgt tgagtcggca    240
tcgtccggtt catcctatgt attccctttc ctgctataaa taccggccgg ccgagggtg    300
```

| | |
|---|---|
| tcgaagccgc agatcaatgg ccgccggcgc cggtagggat ggaggaggag gaagaagagg | 360 |
| cggccttgca tgagggccag agctagcctg cctctggtag ccaaggatga cttgcctaca | 420 |
| tggtctcgct agttccggtt gttgcatgca tgatgcatgg ccagtcctgc tgggtttgtg | 480 |
| ggcggtctcc ttggctagcc tgagtggctc ttgcctgtca tggaaggcct cttcttctct | 540 |
| gccacgtaca ctcgcccgct agtcgcctta tatggtacga cgtacgtacc gtcgtctgcc | 600 |
| tctggcctgt gcttcgtttg gtttgccagg tatgtatggc tgttcaattc attggtgatt | 660 |
| catcagctgg ctcatatata tgtaatgctg catgcaacgc taatattgtt ttcttaatta | 720 |
| ttttgttatt acctgtgccg gcttgcagat tgttctgaat tctgaaatgt atggg | 775 |

<210> SEQ ID NO 51
<211> LENGTH: 762
<212> TYPE: DNA
<213> ORGANISM: Zea mays

<400> SEQUENCE: 51

| | |
|---|---|
| acgaattcct tcctcccmcc agctagctag cgatactact atccaaagag aatatggaga | 60 |
| gatttccctg agattgcscs aatcagtcac tgcactgcac gtacstgtgg agcttttctg | 120 |
| ttttctcata aacsgcaaat gcagcagcag gaggcttttg ggtatttta ttttctctca | 180 |
| acgattggta atcagtatcc gggaaagctg tggatgtggt agaccgacgt gcgttgagtc | 240 |
| ggcatcgtcc ggttcatcct atgtattccc tttcctgcta taaataccgg ccgggccgag | 300 |
| ggtgtcgaag ccgcagatca atgcatggcc gccggcgccg gtagggatgg aggaggagga | 360 |
| ggaagaagag gcggccttgc atgagggcca gagctagcct gcctctggta gccaaggatg | 420 |
| acttgcctac atggtctcgc tagttccggt tgttgcatgc atgatgcatg gccagtcctg | 480 |
| ctgggtttgt gggcggtctc cttgctagcc tgagtggcct cttgcctgtc atggaaggcc | 540 |
| tcttcttctc tgccacgtac actcgcctag ctagtcgcct tatatggtac gtaccgtcgt | 600 |
| ctgcctctgg cggcctgtgc ttcgtttggt ttgccaggta tgtatggctg ttcaattcat | 660 |
| tggtgattca tcagctggct catatatatg taatgckgca tgcaacgcta atattgtttt | 720 |
| cttaattatt tgttattac ctgtgccggc ttgcagattg tt | 762 |

<210> SEQ ID NO 52
<211> LENGTH: 746
<212> TYPE: DNA
<213> ORGANISM: Zea mays

<400> SEQUENCE: 52

| | |
|---|---|
| attccttcct cccaccagct agctagcgat actactatcc aaagagaata tggagagatt | 60 |
| tccctgagat tgcscgaatc agtcactgca ctgcacgtac gtgtggagct tttctgtttt | 120 |
| ctcataaacg gcaaatgcmg cagcaggagg cttttgggta ttttatttt ctctcaacga | 180 |
| ttggtaatca gtatccggga aagctgtgga tgtggtagac cgacgtgcgt tgagtcggca | 240 |
| tcgtccggtt catcctatgt attccctttc tgctataaa taccggccgg ccgagggtg | 300 |
| tcgaagccgc agatcaatgc atggccgccg cgccggtag ggatggagga ggaggaggaa | 360 |
| gaagaggcgg ccttgcatga gggccagagc tagcctgcct ctggtagcca aggatgactt | 420 |
| gcctacatgg tctcgctagt tccggttgtt gcatgcatga tgcatggcca gtcctgctgg | 480 |
| gtttgtgggc ggtctccttg ctagcctga gtggctcttg cctgtcatgg aaggcctctt | 540 |
| cttctctgcc acgtacactc gcctagctag tcgccttata tggtacgtac cgtcgtctgc | 600 |
| ctctggcggc ctgtgcttcg tttggtttgc caggtatgta tggctgttca attcattggt | 660 |

```
gattcatcag ctggctcata tatatgtaat gckgcatgca acgctaatat tgttttctta    720
attattttgt tattacctgt gccggc                                         746

<210> SEQ ID NO 53
<211> LENGTH: 734
<212> TYPE: DNA
<213> ORGANISM: Zea mays

<400> SEQUENCE: 53
gctagctagc gatactacta tccaaagaga atatggagag atttccctga gattgcgcga     60
atcagtcact gcacgtacgt gtggagcttt tctgttttct cataaacgrc aaatrcagca    120
gcaggaggct ttgggtattt ttattttctc tcaacgattg gtaatcagta tctgggaaag    180
ctgtggatgt ggtagaccga cgtgcgttga gtcggcatcg tccggttcat cctatgtatt    240
ccctttcytg ctataaatac cggccgggcc gagggtgtcg aagccgcaga tcaatgcatg    300
gccgcgcgcc ggcgccggta gggatggagg aggaggagga agaagaggcg gccttgcatg    360
agggccagag ctagcctgcc tctggtagcc aaggatgact tgcctacatg gtctcgctag    420
ttccggttgt tgcatgcatg ccactatgcc agtcctgctg gtttgtggg cggtctcctt     480 ggctagcctg agtggctctt gcctgtcatg gaaggcctct tcttctctgc cacgtactct    540
cgcctagcta gtcgccttat ggtacgtacc gtctgcctca gtggctctgg cctgtgcttc    600
gttgggtttg ccaggtaagt atggctgtcg ttcattgctg attcatcagc tggctcatat    660
atatgtaatg ctgcatgcaa cgctaatatc gttttcttaa ttattttgtt attacctgtg    720
cgtgcttgca gatt                                                      734

<210> SEQ ID NO 54
<211> LENGTH: 753
<212> TYPE: DNA
<213> ORGANISM: Zea mays

<400> SEQUENCE: 54
ccagagcagr gsagrgagtc cyttccyccc accagctagc tagcgatact actatccaaa     60
gagaatatgg agagatttcc ctgagattgc gcgaatcagt cactgcacgt acgtgtggag    120
cttttctgtt ttctcataaa cggcaaatgc agcagcagga ggctttgggt attttttattt    180 tctctcaacg attggtaatc agtatccggg aaagctgtgg atgtggtaga ccgacgtgcg    240
ttgagtcggc atcgtccggt tcatcctatg tattcccttt cctgctataa ataccggccg    300
ggccgagggt gtcgaagccg cagatcaatg catggccgcc ggcgccggta gggatggagg    360
aggaggagga agaagaggcg gccttgcatg agggccagag ctagcctgcc tctggtagcc    420
aaggatgact tgcctacatg gtctcgctag ttccggttgt tgcatgcatg atgcatggcc    480
agtcctgctg gtttgtggg cggtctcctt ggctagcctg agtggctctt gcctgtcatg    540
gaaggcctct tcttctctgc cacgtacact cgcctagcta gtcgccttat atggtacgta    600
ccgtcgtctg cctctggcgg cctgtgcttc gtttggtttg ccaggtatgt atggctgttc    660
aattcattgg tgattcatca gctggctcat atatatgtaa tgctgcatgc aacgctaata    720
tcgttttctt aattattttg ttatwacctg tgc                                 753

<210> SEQ ID NO 55
<211> LENGTH: 737
<212> TYPE: DNA
<213> ORGANISM: Zea mays
```

<400> SEQUENCE: 55

```
cccaccagct agctagcgat actactatcc aaagagaata tggagagatt tccctgagat    60
tgcgcgaatc agtcactgca ctgcacgtac gtgtggagct tttctgtttt ctcataaacg   120
gcaaatgcag cagcaggagg ctttgggtat ttttattttc tctcaacgat tggtaatcag   180
tatccgggaa agctgtggat gtggtagacc gacgtgcgtt gagtcggcat cgtccggttc   240
atcctatgta ttccctttcc tgctataaat accggccggg ccgagggtgt cgaagccgca   300
gatcaatgca tggccgccgg cgccggtagg gatggaggag gaggaggaag aagaggcggc   360
cttgcatgag ggccagagct agcctgcctc tggtagccaa ggatgacttg cctacatggt   420
ctcgctagtt ccggttgttg catgcatgat gcatggccag tcctgctggg tttgtgggcg   480
gtctccttgg ctagcctgag tggctcttgc ctgtcatgga aggcctcttc ttctctgcca   540
cgtacactcg cctagctagt cgccttatat ggtacgtacc gtcgtctgcc tctggcggcc   600
tgtgcttcgt ttggtttgcc aggtatgtat ggctgttcaa ttcattggtg attcatcagc   660
tggctcatat atatgtaatg ckgcatgcaa cgctaatatt gttttcttaa ttattttgtt   720
attacctgtg ccggctt                                                  737
```

<210> SEQ ID NO 56
<211> LENGTH: 758
<212> TYPE: DNA
<213> ORGANISM: Zea mays

<400> SEQUENCE: 56

```
cttcctccca ccagctagct agcgatacta ctatccaaag agaatatgga gagatttccc    60
tgagattgcg cgaatcagtc actgcacgta cgtgtggagc ttttctgttt tctcataaam   120
ggcaaatgca gcagcaggag ctttgggta ttttttatttt ctctcaacga ttggtaatca   180
gtatctggga aagctgtgga tgtggtagac cgacgtgcgt tgagtcggca tcgtccggtt   240
catcctatgt attccctttc tgctataaa taccggccgg ccgagggtg tcgaagccgc   300
agatcaatgc atggccgcgc gccggcgccg gtagggatgg aggaggagga ggaagaagag   360
gcggcccttgc atgagggcca gagctagcct gcctctggta gccaaggatg acttgcctac   420
atggtctcgc tagttccggt tgttgcatgc atgccactat gccagtcctg ctgggtttgt   480
gggcggtctc cttggctagc ctgagtggct cttgcctgtc atggaaggcc tcttcttctc   540
tgccacgtac tctcgcctag ctagtcgcct tatggtacgt accgtctgcc tcagtggctc   600
tggcctgtgc ttcgttgggt ttgccaggta agtatggctg tcgttcattg ctgattcatc   660
agctggctca tatatatgta atgctgcatg caacgctaat atcgttttct taattatttt   720
gttattacct gtgcgtgctt gcagattgtt ctgaattc                           758
```

<210> SEQ ID NO 57
<211> LENGTH: 718
<212> TYPE: DNA
<213> ORGANISM: Zea mays
<220> FEATURE:
<221> NAME/KEY: misc_feature
<222> LOCATION: (560)..(627)
<223> OTHER INFORMATION: n is a, c, g, or t

<400> SEQUENCE: 57

```
tagctagcga tactactatc caaagagaat atggagagat ttccctgaga ttgcgcgaaw    60
sagtcactgc mctgcacgta cgtgtggagc ttttctgttt tctcataaac ggcaaatgca   120
gcagcaggag ctttgggta ttttttatttt ctctcaacga ttggtaatca gtatccggga   180
```

```
aagctgtgga tgtggtagac cgacgtgcgt tgagtcggca tcgtccggtt catcctatgt      240
attccctttc ctgctataaa taccggccgg gccgagggtg tcgaagccgc agatcaatgc      300
atggccgccg gcgccggtag ggatggagga ggaggaggaa gaagaggcgg ccttgcatga      360
gggccagagc tagcctgcct ctggtagcca aggatgactt gcctacatgg tctcgctagt      420
tccggttgtt gcatgcatgm yrctakgcca gtcctgctgg gtttgtgggc ggtctccttg      480
gctagcctga gtggctcttg cctgtcatgg aaggcctctt cttctctgcc acgtacwctc      540
gcctagctag tcgccttatn nnnnnnnnnn nnnnnnnnnn nnnnnnnnnn nnnnnnnnnn      600
nnnnnnnnnn nnnnnnnnnn nnnnnnnmrt tcattgstga ttcatcagck ggctcatata      660
tatgtaatgc tgcatgcaac gctaatatyg ttttcttaat tattttgtta twacctst       718
```

<210> SEQ ID NO 58
<211> LENGTH: 775
<212> TYPE: DNA
<213> ORGANISM: Zea mays

<400> SEQUENCE: 58

```
agggcaggga gtccttcctt cctcccacca gctagcgata ctactatcca aagagaatat      60
ggagagattt ccctgagatt gcgcgaatca gtcactgcac gtacgtgtgg agcttttctg     120
ttttctcata aacggcaaat gcagcagcag gaggctttgg gtatttttat tttctctcag     180
cgattggtaa tcagtatccg ggaaagacgt ggatgtggta gaccgacgtg cgttgagtcg     240
gcatcgtccg gttcatccta tgtattccct ttcctgctat aaataccggc cgggccgagg     300
gtgtcgaaac cgcagatcaa tggccgccgg cgccggtagg gatggaggag gaagaagaag     360
aggcggcctt gcatgagggc cagagctagc ctgcctctgg tagccaagga tgacttgcct     420
acatggtctc gctagttccg gttgttgcat gcatgatgca tggccagtcc tgctgggttt     480
gtgggcggtc tccttggcta gcctgagtgg ctcttgccta tcatggaagg cctcttcttc     540
tctgccacgt acactcgcct aactagtcgc cttatggtac gtaccgtctg gctcagtggc     600
tctggcctgt gcttcgttgg gtttgccagg taagtatggc tgttcaattc attggtgatt     660
catcagctgg ctcatatata tgtaatgctg catgcaacgc taatattgtt ttcttaatta     720
ttttgttatt acctgtgcgt gcttgcagat tgttctgaat tctgaaatgt atggg          775
```

<210> SEQ ID NO 59
<211> LENGTH: 758
<212> TYPE: DNA
<213> ORGANISM: Zea mays

<400> SEQUENCE: 59

```
acgaattcct tcctcccacc agctagctag cgatactact atccaaagag aatatggaga      60
gatttccctg agattgcgcg aatcagtcac tgcactgcac gtacgtgtgg agcttttctg     120
ttttctcata aacggcaaat gcagcagccg gaggctttgg gtatttttat tttctctcaa     180
cgattggtaa tcagtatccg ggaaagctgt ggatgtggta gaccgacgtg cgttgagtcg     240
gcatcgtccg gttcatccta tgtattccct ttcctgctat aaataccggc cgggccgagg     300
gtgtcgaagc cgcagatcaa tgcatggccg ccggcgccgg tagggatgga ggaggggggag     360 gaagaagagg cggccttgca tgagggccag agctagcctg cctctggtag ccaaggatga     420
cttgcctaca tggtctcgct agttccggtt gttgcatgca tgatgcatgg ccagtcctgc     480
tgggtttgtg ggcggtctcc ttggctagcc tgagtggctc ttgcctgtca tggaaggcct     540
```

```
cttcttctct gccacgtaca ctcgcctagc tagtcgcctt atatggtacg taccgtcgtc    600
tgcctctggc ggcctgtgct tcgtttggtt tgccaggtat gtatggctgt tcaattcatt    660
ggtgattcat cagctggctc atatatatgt aatgctgcat gcaacgctaa tattgttttc    720
ttaattattt tgttattacc tgtgccggct tgcagatt                            758
```

<210> SEQ ID NO 60
<211> LENGTH: 787
<212> TYPE: DNA
<213> ORGANISM: Zea mays

<400> SEQUENCE: 60

```
gagcagggma gggagtcctt cctcccacca gctagctagc gatactacta tccaaagaga     60
atatggagag atttccctga gattgcgcga atcagtcact gcacgtacgt gtggagcttt    120
tctgttttct cataaacggc aaatgcagca gcaggaggct ttgggtattt ttattttctc    180
tcaacgattg gtaatcagta tctgggaaag ctgtggatgt ggtagaccga cgtgcgttga    240
gtcggcatcg tccggttcat cctatgtatt ccctttcctg ctataaatac cggccgggcc    300
gagggtgtcg aagccgcaga tcaatgcatg gccgcgcgcc ggcgccggta gggatggagg    360
aggaggagga agaagaggcg gccttgcatg agggccagag ctagcctgcc tctggtagcc    420
aaggatgact tgcctacatg gtctcgctag ttccggttgt tgcatgcatg ccactatgcc    480
agtcctgctg ggtttgtggg cggtctcctt ggctagcctg agtggctctt gcctgtcatg    540
gaaggcctct tcttctctgc cacgtactct cgcctagcta gtcgcctat ggtacgtacc     600 gtctgcctca gtggctctgg cctgtgcttc gtttgggttg ccaggtaagt atggctgtcg    660
ttcattgctg attcatcagc tggctcatat atatgtaatg ctgcatgcaa cgctaatatc    720
gttttcttaa ttattttgtt attacctgtg cgtgcttgca gattgttctg aattctgaaa    780
tgtatgg                                                              787
```

<210> SEQ ID NO 61
<211> LENGTH: 758
<212> TYPE: DNA
<213> ORGANISM: Zea mays

<400> SEQUENCE: 61

```
acgaattcct tcctcccacc agctagctag cgatactact atccaaagag aatatggaga     60
gatttccctg agattgcgcg aatcagtcac tgcactgcac gtacgtgtgg agcttttctg    120
ttttctcata aacggcaaat gcagcagcag gaggctttgg gtattttat tttctctcaa     180 cgattggtaa tcagtatccg ggaaagctgt ggatgtggta gaccgacgtg cgttgagtcg    240
gcatcgtccg gttcatccta tgtattccct ttcctgctat aaataccggc cgggccgagg    300
gtgtcgaagc cgcagatcaa tgcatggccg ccggcgccgg tagggatgga ggaggaggag    360
gaagaagagg cggccttgca tgagggccag agctagcctg cctctggtag ccaaggatga    420
cttgcctaca tggtctcgct agttccggtt gttgcatgca tgatgcatgg ccagtcctgc    480
tgggtttgtg ggcggtctcc ttggctagcc tgagtggctc ttgcctgtca tggaaggcct    540
cttcttctct gccacgtaca ctcgcctagc tagtcgcctt atatggtacg taccgtcgtc    600
tgcctctggc ggcctgtgct tcgtttggtt tgccaggtat gtatggctgt tcaattcatt    660
ggtgattcat cagctggctc atatatatgt aatgctgcat gcaacgctaa tatkgttttc    720
ttaattattt tgttattacc tgtgccggct tgcagatt                            758
```

```
<210> SEQ ID NO 62
<211> LENGTH: 770
<212> TYPE: DNA
<213> ORGANISM: Zea mays

<400> SEQUENCE: 62
agcagggcag ggagtccttc ctcccaccag ctagctagcg atactactat ccaaagagaa      60
tatggagaga tttccctgag attgcgcgaa tcagtcactg cacgtacgtg tggagctttt     120
ctgttttctc ataaacggca aatgcagcag caggaggctt gggtatttt tattttctct      180 caacgattgg taatcagtat ctgggaaagc tgtggatgtg gtagaccgac gtgcgttgag     240
tcggcatcgt ccggttcatc ctatgtattc cctttcctgc tataaatacc ggccgggccg     300
agggtgtcga agccgcagat caatgcatgg ccgcgcgccg gcgccggtag ggatggagga     360
ggaggaggaa gaagaggcgg ccttgcatga gggccagagc tagcctgcct ctggtagcca     420
aggatgactt gcctacatgg tctcgctagt tccggttgtt gcatgcatgc cactatgcca     480
gtcctgctgg gtttgtgggc ggtctccttg gctagcctga gtggctcttg cctgtcatgg     540
aaggcctctt cttctctgcc acgtactctc gcctagctag tcgccttatg gtacgtaccg     600
tctgcctcag tggctctggc ctgtgcttcg ttgggtttgc caggtaagta tggctgtcgt     660
tcattgctga ttcatcagct ggctcatata tatgtaatgc tgcatgcaac gctaatatcg     720
ttttcttaat tattttgtta ttacctgtgc gtgcttgcag attgttctga                770

<210> SEQ ID NO 63
<211> LENGTH: 730
<212> TYPE: DNA
<213> ORGANISM: Zea mays

<400> SEQUENCE: 63
accagctagc tagcgatact actatccaaa gagaatatgg agagatttcc ctgagattgc      60
gcgaatcagt cactgcacgt acgtgtggag cttttctgtt ttctcataaa cggcaaatgc     120
agcagcagga ggctttgggt attttttattt tctctcaacg attggtaatc agtatctggg     180
aaagctgtgg atgtggtaga ccgacgtgcg ttgagtcggc atcgtccggt tcatcctatg     240
tattcccttt cctgctataa ataccggccg ggccgagggt gtcgaagccg cagatcaatg     300
catggccgcg cgccggcgcc ggtagggatg gaggaggagg aggaagaaga ggcggccttg     360
catgagggcc agagctagcc tgcctctggt agccaaggat gacttgccta catggtctcg     420
ctagttccgg ttgttgcatg catgccacta tgccagtcct gctgggtttg tgggcggtct     480
ccttggctag cctgagtggc tcttgcctgt catggaaggc ctcttcttct ctgccacgta     540
ctctcgccta gctagtcgcc ttatggtacg taccgtctgc ctcagtggct ctggcctgtg     600
cttcgttggg tttgccaggt aagtatggct gtcgttcatt gctgattcat cagctggctc     660
atatatatgt aatgctgcat gcaacgctaa tatcgttttc ttaattattt tgttattacc     720
tgtgcgtgct                                                            730

<210> SEQ ID NO 64
<211> LENGTH: 731
<212> TYPE: DNA
<213> ORGANISM: Zea mays

<400> SEQUENCE: 64
ccagctagct agcgatacta ctatccaaag agaatatgga gagatttccc tgagattgcg      60
cgaatcagtc actgcacgta cgtgtggagc ttttctgttt tctcataaac ggcaaatgca     120
```

-continued

| | |
|---|---|
| gcagcaggag gctttgggta ttttatttt ctctcaacga ttggtaatca gtatctggga | 180 |
| aagctgtgga tgtggtagac cgacgtgcgt tgagtcggca tcgtccggtt catcctatgt | 240 |
| attcccttc ctgctataaa taccggccgg gccgagggtg tcgaagccgc agatcaatgc | 300 |
| atggccgcgc gccggcgccg gtagggatgg aggaggagga ggaagaagag gcggccttgc | 360 |
| atgagggcca gagctagcct gcctctggta gccaaggatg acttgcctac atggtctcgc | 420 |
| tagttccggt tgttgcatgc atgccactat gccagtcctg ctgggtttgt gggcggtctc | 480 |
| cttggctagc ctgagtggct cttgcctgtc atggaaggcc tcttcttctc tgccacgtac | 540 |
| tctcgcctag ctagtcgcct tatggtacgt accgtctgcc tcagtggctc tggcctgtgc | 600 |
| ttcgttgggt ttgccaggta agtatggctg tcgttcattg ctgattcatc agctggctca | 660 |
| tatatatgta atgctgcatg caacgctaat atcgttttct taattatttt gttattacct | 720 |
| gtgcgtgctt g | 731 |

<210> SEQ ID NO 65
<211> LENGTH: 783
<212> TYPE: DNA
<213> ORGANISM: Zea mays

<400> SEQUENCE: 65

| | |
|---|---|
| gagcagggca gggagtcctt cctcccacca gctagctagc gatactacta tccaaagaga | 60 |
| atatggagag atttccctga gattgcgcga atcagtcact gcacgtacgt gtggagcttt | 120 |
| tctgttttct cataaacggc aaatgcagca gcaggaggct ttgggtattt ttattttctc | 180 |
| tcaacgattg gtaatcagta tctgggaaag ctgtggatgt ggtagaccga cgtgcgttga | 240 |
| gtcggcatcg tccggttcat cctatgtatt ccctttcctg ctataaatac cggccgggcc | 300 |
| gagggtgtcg aagccgcaga tcaatgcatg gccgcgcgcc ggcgccggta gggatggagg | 360 |
| aggaggagga agaaggagcg ccttgcatg agggccagag ctagcctgcc tctggtagcc | 420 |
| aaggatgact tgcctacatg gtctcgctag ttccggttgt tgcatgcatg ccactatgcc | 480 |
| agtcctgctg ggtttgtggg cggtctcctt ggctagcctg agtggctctt gcctgtcatg | 540 |
| gaaggcctct tcttctctgc cacgtactct cgcctagcta gtcgccttat ggtacgtacc | 600 |
| gtctgcctca gtggctctgg cctgtgcttc gttgggtttg ccaggtaagt atggctgtcg | 660 |
| ttcattgctg attcatcagc tggctcatat atatgtaatg ctgcatgcaa cgctaatatc | 720 |
| gttttcttaa ttattttgtt attacctgtg cgtgcttgca gattgttctg aattctgaaa | 780 |
| tgt | 783 |

<210> SEQ ID NO 66
<211> LENGTH: 769
<212> TYPE: DNA
<213> ORGANISM: Zea mays

<400> SEQUENCE: 66

| | |
|---|---|
| agagcagggc agggagtcct tcctcccacc agctagctag cgatactact atccaaagag | 60 |
| aatatggaga gatttccctg agattgcgcg aatcagtcac tgcacgtacg tgtggagctt | 120 |
| ttctgttttc tcataaacgg caaatgcagc agcaggaggc tttgggtatt tttattttct | 180 |
| ctcaacgatt ggtaatcagt atctgggaaa gctgtggatg tggtagaccg acgtgcgttg | 240 |
| agtcggcatc gtccggttca tcctatgtat tccctttcct gctataaata ccggccgggc | 300 |
| cgagggtgtc gaagccgcag atcaatgcat ggccgcgcgc cggcgccggt agggatggag | 360 |
| gaggaggagg aagaagaggc ggccttgcat gagggccaga gctagcctgc ctctggtagc | 420 |

```
caaggatgac ttgcctacat ggtctcgcta gttccggttg ttgcatgcat gccactatgc    480
cagtcctgct gggtttgtgg gcggtctcct tggctagcct gagtggctct tgcctgtcat    540
ggaaggcctc ttcttctctg ccacgtactc tcgcctagct agtcgcctta tggtacgtac    600
cgtctgcctc agtggctctg gcctgtgctt cgttgggttt gccaggtaag tatggctgtc    660
gttcattgct gattcatcag ctggctcata tatatgtaat gctgcatgca acgctaatat    720
cgttttctta attattttgt tattacctgt gcgtgcttgc agattgttc                769
```

<210> SEQ ID NO 67
<211> LENGTH: 21
<212> TYPE: DNA
<213> ORGANISM: Zea mays

<400> SEQUENCE: 67

```
tgattgagcc gcgccaatat c                                              21
```

<210> SEQ ID NO 68
<211> LENGTH: 99
<212> TYPE: DNA
<213> ORGANISM: Zea mays

<400> SEQUENCE: 68

```
gatattggcg aggttcaatc agatgatgta ttttcttat atataaattt gcatgcatga     60
aggtgtgaat ccagtgtctg attgagccgc gccaatatc                           99
```

<210> SEQ ID NO 69
<211> LENGTH: 645
<212> TYPE: DNA
<213> ORGANISM: Zea mays

<400> SEQUENCE: 69

```
cagtcggccg atgctcgcgc gtgcctcgat tcttttctcg aggctagcta gctacctaca    60
ggtgacgcat gcatgcatat atagttgcat ctgcgtgtgt tagatgagca cttgtaaaag    120
agatcatgtg atgagggggg ggggggggg ggagagagag agagagagga ggaagacgcg     180
gccggactat ttagctatcc gtgtgtgatg aagggcagta gcagtatatg tgctgctttg    240
atgaattcca tggttggatg gcatggaggg agcgatattg gcgaggttca atcagatgat    300
gtatttttct tatatataaa tttgcatgca tgaaggtgtg aatccagtgt ctgattgagc    360
cgcgccaata tcacttcctt ccaccataag tttacacaca gagaggattg cagcgagcgc    420
gtctacttcc aaaggttaga ccactcgtta tttcctcatt tccaaattac acttgtctat    480
tatactccct ctgtgccatt atagtgttcg ttttagcttt tctttgtcca tattaaaata    540
gatatcaatg aatatatata tatataatat ttttggagca ctagacttct aatgactaca    600
cgaagccctg acccaacggt gccatccggt tcagccacat cagat                    645
```

<210> SEQ ID NO 70
<211> LENGTH: 643
<212> TYPE: DNA
<213> ORGANISM: Zea mays

<400> SEQUENCE: 70

```
agtcggccga tgctcgcgcg tgcctcgatt cttttctcga ggctagctag ctacctacag    60
gtgacgcatg catgcatata tagttgcatc tgcgtgtgtt agatgagcac ttgtaaaaga    120
gatcatgtga tgagggggg gggggggggg agagagagag agagaggagg aagacgcggc     180
```

```
cggactattt agctatccgt gtgtgatgaa gggcagtagc agtatatgtg ctgctttgat      240
gaattccatg gttggatggc atggaggag cgatattggc gaggttcaat cagatgatgt       300
atttttctta tatataaatt tgcatgcatg aaggtgtgaa tccagtgtct gattgagccg      360
cgccaatatc acttccttcc accataagtt tacacacaga gaggattgca gcgagcgcgt      420
ctacttccaa aggttagacc actcgttatt tcctcatttc caaattacac ttgtctatta      480
tactccctct gtgccattat agtgttcgtt ttagcttttc tttgtccata ttaaaataga      540
tatcaatgaa tatatatata tataatatatt ttggagcact agacttctaa tgactacacg    600
aagccctgac ccaacggtgc catccggttc agccacatca gat                        643
```

```
<210> SEQ ID NO 71
<211> LENGTH: 625
<212> TYPE: DNA
<213> ORGANISM: Zea mays

<400> SEQUENCE: 71
tcggccgatg ctcgcgcgtg cctcgattct tttctcgagg ctagctagct acctacaggt       60
gacgcatgca tgcatatata gttgcatctg cgtgtgttag atgagcactt gtaaaagaga     120
tcatgtgatg aggggggggg ggggggggag agagagagag agaggaggaa gacgcggccg     180
gactatttag ctatccgtgt gtgatgaagg gcagtagcag tatatgtgct gctttgatga     240
attccatggt tggatggcat ggaggagcg atattggcga ggttcaatca gatgatgtat     300
ttttcttata taaatttg catgcatgaa ggtgtgaatc cagtgtctga ttgagccgcg       360
ccaatatcac ttccttccac cataagttta cacacagaga ggattgcagc gagcgcgtct    420
acttccaaag gttagaccac tcgttatttc ctcatttcca aattacactt gtctattata    480
ctccctctgt gccattatag tgttcgtttt agcttttctt tgtccatatt aaaatagata    540
tcaatgaata tatatatata taatatttttt ggagcactag acttctaatg actacacgaa   600
gccctgaccc aacggtgcca tccgg                                           625
```

```
<210> SEQ ID NO 72
<211> LENGTH: 644
<212> TYPE: DNA
<213> ORGANISM: Zea mays
<220> FEATURE:
<221> NAME/KEY: misc_feature
<222> LOCATION: (153)..(164)
<223> OTHER INFORMATION: n is a, c, g, or t

<400> SEQUENCE: 72
cagtcggccg atgctcgcgc gtgcctcgat tcttttctcg aggctagcta gctacctaca      60
ggtgacgcat gcatgcatat atagttgcat ctgcgtgtgt tagatgasca cttgtaaaag    120
agatcatgtg atgaggggg ggggggggr rrnnnnnnnn nnnngaggag gaagacgcgg       180
ccggactatt tagctatccg tgtgtgatga agggcagtag cagtatatgt gctgctttga    240
tgaattccat ggttggatgg catggaggga gcgatattgg cgaggttcaa tcagatgatg    300
tattttcctt atatataaat ttgcatgcat gaaggtgtga atccagtgtc tgattgagcc    360
gcgccaatat cacttccttc caccataagt ttacacacag agaggattgc agcgagcgcg    420
tctacttcca aaggttagac cactcgttat ttcctcattt ccaaattaca cttgtctatt    480
atactccctc tgtgccattm tmgtgttcgt tttagctttt ctttgtccat attaaaatag    540
atatcaatga atatatatat ataatatatt tttggagcac tagacttcta atgactacac    600
gaagccctga cccaacggtg ccatccggtt cagccacatc agat                     644
```

<210> SEQ ID NO 73
<211> LENGTH: 572
<212> TYPE: DNA
<213> ORGANISM: Zea mays

<400> SEQUENCE: 73

| | | | | | |
|---|---|---|---|---|---|
| tytcgwggct | agctagctac | ctacaggtga | cgyatgcatg | catatatagt | tgcatctgcg | 60 |
| tgtgttagat | gagcacttgt | aaaagagatc | atgtgatgag | gggggggggg | ggggrgagag | 120 |
| agagagagag | aggaggaaga | cgcggccgga | ctatttagct | atccgtgtgt | gatgaagggc | 180 |
| agtagcagta | tatgtgctgc | tttgatgaat | tccatggttg | gatggcatgg | agggagcgat | 240 |
| attggcgagg | ttcaatcaga | tgatgtattt | ttcttatata | taaatttgca | tgcatgaagg | 300 |
| tgtgaatcca | gtgtctgatt | gagccgcgcc | aatatcactt | ccttccacca | taagtttaca | 360 |
| cacagagagg | attgcagcga | gcgcgtctac | ttccaaaggt | tagaccactc | gttatttcct | 420 |
| catttccaaa | ttacacttgt | ctattatact | ccctctgtgc | caytatwgtg | ttcgttttag | 480 |
| cttttctttg | tccatattaa | aatagatatc | aatgaatata | tatatatata | atatttttgg | 540 |
| agcactagac | ttctaatgac | tacacgaarm | cc | | | 572 |

<210> SEQ ID NO 74
<211> LENGTH: 586
<212> TYPE: DNA
<213> ORGANISM: Zea mays

<400> SEQUENCE: 74

| | | | | | |
|---|---|---|---|---|---|
| agckagctac | aggtgacgca | yacawgcata | tatagttgca | tctgcgtgtg | ttagatgagc | 60 |
| actcttgtaa | aagagatcat | gtgatgagag | gggggagag | gaggaagacg | tggccggact | 120 |
| atttagctat | ccgtgtgtga | tgaagggcag | tagcagtata | tgtgctgctt | tgatgaattc | 180 |
| catggttgga | tggcatggag | ggagcgatat | tggcgaggtt | caatcagatg | atgtattttt | 240 |
| cttatatata | aatttgcatg | catgaaggtg | tgaatccagt | gtctgattga | gccgcgccaa | 300 |
| tatcacttcc | ttccaccata | agtttacaca | cagagaggat | tgcagcgagc | gcgtctactt | 360 |
| ccaaaggtta | gaccagtcgt | tatttcctca | tttccaaatt | acacttgtct | attatactcc | 420 |
| ctctgtgcca | tcatagtgtt | cgttttagct | tttctttgtt | catattaaaa | tagatatcar | 480 |
| tgaatatata | tatatatata | tatatataat | atttttggag | cactagactt | ctaatgacta | 540 |
| cacgaagccc | tgacccaacg | gtgccatccg | gttcagccac | atcara | | 586 |

<210> SEQ ID NO 75
<211> LENGTH: 617
<212> TYPE: DNA
<213> ORGANISM: Zea mays

<400> SEQUENCE: 75

| | | | | | |
|---|---|---|---|---|---|
| cagtcggccg | atgctcgcgc | gtgcctcgat | tcttttctcg | aggctagcta | gctacctaca | 60 |
| ggtgacgcat | gcatgcatat | atagttgcat | ctgcgtgtgt | tagatgagca | cttgtaaaag | 120 |
| agatcatgtg | atgaggggg | ggggggggr | gagagagaga | gagagaggag | gaagacgcgg | 180 |
| ccggactatt | tagctatccg | tgtgtgatga | agggcagtag | cagtatatgt | gctgctttga | 240 |
| tgaattccat | ggttggatgg | catggaggga | gcgatattgg | cgaggttcaa | tcagatgatg | 300 |
| tatttttctt | atatataaat | ttgcatgcat | gaaggtgtga | atccagtgtc | tgattgagcc | 360 |
| gcgccaatat | cacttccttc | caccataagt | ttacacacag | agaggattgc | agcgagcgcg | 420 |

| tctacttcca aaggttagac cactcgttat ttcctcattt ccaaattaca cttgtctatt | 480 |
| atactccctc tgtgccatta yastgttcgt tttagctttt ctttgtccat attaaaatag | 540 |
| atatcaatga atatatatat atataatatt tttggagcac tagacttcta atgactacac | 600 |
| gaagccctga cccaamg | 617 |

<210> SEQ ID NO 76
<211> LENGTH: 594
<212> TYPE: DNA
<213> ORGANISM: Zea mays

<400> SEQUENCE: 76

| gtctcgattc ttttctcgag gctagctagc tacaggtgac gcatacaatg catatatagt | 60 |
| tgcatctgcg tgtgttagat gagcactctt gtaaaagaga tcatgtgatg agagggggg | 120 |
| gagaggagga agacgtggcc ggactattta gctatccgtg tgtgatgaag ggcagtagca | 180 |
| gtatatgtgc tgctttgatg aattccatgg ttggatggca tggagggagc gatattggcg | 240 |
| aggttcaatc agatgatgta ttttcttat atataaattt gcatgcatga aggtgtgaat | 300 |
| ccagtgtctg attgagccgc gccaatatca cttccttcca cataagtttt acacacagag | 360 |
| aggattgcag cgagcgcgtc tacttccaaa ggttagacca gtcgttattt cctcatttcc | 420 |
| aaattacact tgtctattat actccctctg tgccatcata gtgttcgttt tagcttttct | 480 |
| ttgttcatat taaatagat atcaatgaat atatatat atatataata ttttggagc | 540 |
| actagacttc taatgactac acgaagccct gacccaacgg tgccatccgg ttca | 594 |

<210> SEQ ID NO 77
<211> LENGTH: 569
<212> TYPE: DNA
<213> ORGANISM: Zea mays

<400> SEQUENCE: 77

| gtgacgcata cratgcatat atagttgcat ctgcgtgtgt tagatgagca ctcttgtaaa | 60 |
| agagatcatg tgatgagagg gggggagag ggagaggagg aagacgtggc cggactattt | 120 |
| agctatccgt gtgtgatgaa gggcagtagc agtatatgtg ctgctttgat gaattccatg | 180 |
| gttggatggc atggagggag cgatattggc gaggttcaat cagatgatgt atttttctta | 240 |
| tataaaattt gcatgcatg aaggtgtgaa tccagtgtct gattgagccg cgccaatatc | 300 |
| acttycttcc accataagtt tacacacaga gaggattgca gcgagcgcgt ctacttccaa | 360 |
| aggttagacc agtcgttatt tcctcatttc caaattacac ttgtctatta tactccctct | 420 |
| gtgccattat agtgttcgtt ttagcttttc tttgttcata ttaaaataga tatcwatgaa | 480 |
| tatatatata tatatataat attttttggag cactagactt ctaatgacta cacgaagccc | 540 |
| tgacccaacg gtgccatccg gttcagcca | 569 |

<210> SEQ ID NO 78
<211> LENGTH: 463
<212> TYPE: DNA
<213> ORGANISM: Zea mays

<400> SEQUENCE: 78

| ggggggggag agagagagag agaggaggaa gacgcggccg gactatttag ctatccgtgt | 60 |
| gtgatgaagg gcagtagcag tatatgtgct gcyttgatga attccatggt tggatggcat | 120 |
| ggagggagcg atattggcga ggttcaatca gatgatgtat ttttcttata tataaatttg | 180 |
| catgcatgaa ggtgtgaatc cagtgtctga ttgagccgcg ccaatatcac ttccttccac | 240 |

```
cataagtttta cacacagaga ggattgcagc gagcgcgtct acttccaaag gttagaccac    300
tcgttatttc ctcatttcca aattacactt gtctattata ctccctctgt gccattatas    360
tgttcgtttt agcttttctt tgtccatatt aaaatagata tcaatgaata tatatatata    420 taatatttt ggagcactag acttctaatg actacacgaa gcc                       463
```

<210> SEQ ID NO 79
<211> LENGTH: 604
<212> TYPE: DNA
<213> ORGANISM: Zea mays

<400> SEQUENCE: 79

```
tcgattctttt tytcgaggct agctagctac aggtgacgca tacaatgcat atatagttgc     60
atctgcgtgt gttagatgag cactcttgta aaagagatca tgtgatgaga ggggggggga    120
gaggaggaag acgtggccgg actatttagc tatccgtgtg tgatgaaggg cagtagcagt    180
atatgtgctg ctttgatgaa ttccatggtt ggatggcatg gagggagcga tattggcgag    240
gttcaatcag atgatgtatt tttcttatat ataaatttgc atgcatgaag gtgtgaatcc    300
agtgtctgat tgagccgcgc caatatcact tccttccacc ataagtttac acacagagag    360
gattgcagcg agcgcgtcta cttccaaagg ttagaccagt cgttatttcc tcatttccaa    420
attacacttg tctattatac tccctctgtg ccatcatagt gttcgtttta gcttttcttt    480
gttcatatta aaatagatat caatgaatat atatatatat ataatatatt tttggagcac    540
tagacttcta atgactacac gaagccctga cccaacggtg ccatccggtt cagccacatc    600
agat                                                                  604
```

<210> SEQ ID NO 80
<211> LENGTH: 612
<212> TYPE: DNA
<213> ORGANISM: Zea mays
<220> FEATURE:
<221> NAME/KEY: misc_feature
<222> LOCATION: (123)..(125)
<223> OTHER INFORMATION: n is a, c, g, or t

<400> SEQUENCE: 80

```
gcgcgtgcct cgattctttt ctcgaggcta gctagctrcc tacaggtgac gcatgcatgc     60
atatatagtt gcatctgcgt gtgttagatg ascacttgta aaagagatca tgtgatgagg    120 ggnnngggggg ggggagaga gagagagaga ggaggaagac gcggccggac tatttagcta    180
tccgtgtgtg atgaagggca gtagcagtat atgtgcygct ttgatgaatt ccatggttgg    240
atggcatgga gggagcgata ttggcgaggt tcaatcagat gatgtattt tcttatatat    300 aaatttgcat gcatgaaggt gtgaatccag tgtctgattg agccgcgcca atatcacttc    360
cttccaccat aagtttacac acagagagga ttgcagcgag cgcgtctact tccaaaggtt    420
agaccactcg ttatttcctc atttccaaat tacacttgtc tattatactc cctctgtgcc    480
attatmgtgt tcgttttagc ttttctttgt ccatattaaa atagatatca atgaatatat    540
atatatataa tattttggga gcactagact tctaatgact acacgaagcc ctgacccaac    600
ggtgccatcc gg                                                         612
```

<210> SEQ ID NO 81
<211> LENGTH: 622
<212> TYPE: DNA
<213> ORGANISM: Zea mays
<220> FEATURE:

<221> NAME/KEY: misc_feature
<222> LOCATION: (87)..(119)
<223> OTHER INFORMATION: n is a, c, g, or t

<400> SEQUENCE: 81

| | | | | | |
|---|---|---|---|---|---|
| gcctckattc | ttttctcgag | gctagctagc | tacctacagg | tgacgcatgc | atgcatatat | 60 |
| wgttgcatct | gcgtgtgtta | gatgagnnnn | nnnnnnnnnn | nnnnnnnnnn | nnnnnnnnnk | 120 |
| gggggggggga | gagagagaga | gagaggagga | agacgcggcc | ggactattta | gctatccgtg | 180 |
| tgtgatgaag | ggcagtagca | gtatatgtgc | tgctttgatg | aattccatgg | ttggatggca | 240 |
| tggagggagc | gatattggcg | aggttcaatc | agatgatgta | tttttcttat | atataaattt | 300 |
| gcatgcatga | aggtgtgaat | ccagtgtctg | attgagccgc | gccaatatca | cttccttcca | 360 |
| ccataagttt | acacacagag | aggattgcag | cgagcgcgtc | tacttccaaa | ggttagacca | 420 |
| ctcgttattt | cctcatttcc | aaattacact | tgtctattat | actccctctg | tgccattata | 480 |
| gtgttcgttt | tagcttttct | ttgtccatat | taaaatagat | atcaatgaat | atatatatat | 540 |
| ataatatttt | tggagcacta | gacttctaat | gactacacga | agccctgacc | caacggtgcc | 600 |
| atccggttca | gccacatcag | at | | | | 622 |

<210> SEQ ID NO 82
<211> LENGTH: 22
<212> TYPE: DNA
<213> ORGANISM: Zea mays

<400> SEQUENCE: 82
tccaaaggga tcgcattgat ct                                              22

<210> SEQ ID NO 83
<211> LENGTH: 126
<212> TYPE: DNA
<213> ORGANISM: Zea mays

<400> SEQUENCE: 83

| | | | | | |
|---|---|---|---|---|---|
| ccaggaagct | ggtggaggac | tccaaaggga | tcgcattgat | ctattctcac | ctgccgcctg | 60 |
| ctgcatgcga | tgcgagtcga | cgacaagatc | agtgcaatcc | ctttggaatt | ttccactcgc | 120 |
| gccttc | | | | | | 126 |

<210> SEQ ID NO 84
<211> LENGTH: 779
<212> TYPE: DNA
<213> ORGANISM: Zea mays

<400> SEQUENCE: 84

| | | | | | |
|---|---|---|---|---|---|
| agcatctccg | tggtgggccc | tccgtgtccc | cttcggcccg | ggatggccca | cgtgcacgtc | 60 |
| gaaagcgtga | gagcgagagg | aggacgccta | cctaagcgag | caatgcaaca | gccatcatcg | 120 |
| tcattcacct | tgcctatcca | tcatcctcgt | cttcttctgt | ctatccatgg | cgatttggcg | 180 |
| ttataaccac | ccccaccccc | acccttctct | ggctacgtcc | tcgctttccc | ttcctcccag | 240 |
| ctgcctgccc | cccttccct | accctagcta | cgcacgctac | cagctgcccc | ccatccatgc | 300 |
| cgtccaggaa | gctggtggag | gactccaaag | ggatcgcatt | gatctattct | cacctgccgc | 360 |
| ctgctgcatg | cgatgcgagt | cgacgacaag | atcagtgcaa | tcccttttgga | attttccact | 420 |
| cgcgccttca | cccccgccgc | acgtgccaca | cgcccctcca | tcttcatgg | attccatctc | 480 |
| tcatcaggta | tctctctctc | tatctgctct | tgcaagctac | ttccatggat | ttgattttttg | 540 |
| ttaagttcgc | ctacttgctc | tccacgtacg | tactggctac | atcgtttctg | cgcaccacac | 600 |

```
acccaccagg ccatgaggaa tcaatttgct catgggagca tgatgatgca gacaagtaca    660
aacatagtat ataataaaaa tagctgccga ttcattcttt cctttcgctc atcgttttcg    720
tagttaattc attcattggc atggttaagt atgtgtaaat acttacatgt agatatatc     779

<210> SEQ ID NO 85
<211> LENGTH: 791
<212> TYPE: DNA
<213> ORGANISM: Zea mays

<400> SEQUENCE: 85
tccgtgtccc cttcggcccg ggatggccca cgtgcacgtc gaaagcgtga gagcgagagg     60
aggacgccta cctaagcgag caatgcaaca gccatcatcg tcattcacct tgcctatcca    120
tcatcctcgt cttcttctgt ctatccatgg cgatttggcg ttataaccac ccccaccccc    180
acccttctct ggctacgtcc tcgctttccc ttcctcccag ctgcctgccc cccctccct    240 acccyagcta cgcacgctac cagctgcccc ccatccatgc cgtccaggaa gctggtggag    300
gactccaaag ggatcgcayt gatmtattct cacctgcmgc ctgytgcayg cgatgcgagt    360
ygacgacaag atcagtgcaa tccctttgga attttccact cgcgccttca ccccgcccc    420 sccctccat gcacgcataa atccaattcc aagctttcca tggattccat ctctcatcag    480
rtatctctct ctctctatct gctcttgcaa gctacttcca tggatttgat ttttgttaag    540
ttcgcctact tgctctccac gtacgtacta gctacatcgt ttccaccagc ccatgaggag    600
ttattcaatc tacgagtctg ctgcctcctt caatttgctc atgggagcat gmtgatagat    660
gcagacaagt acaaacatag tatataataa aaatagctgc cgattcattc ttyccttcg    720 ctcatcgttt tcgtagttaa ttcattcatt ggcatggtta agtatgtgta aatacttaca    780
tgtagatata t                                                         791

<210> SEQ ID NO 86
<211> LENGTH: 765
<212> TYPE: DNA
<213> ORGANISM: Zea mays

<400> SEQUENCE: 86
tggtgggccc tccgtgtccc cttcggcccg ggatggccca cgtgcacgtc gaaagcgtga     60
gagcgagagg aggacgccta cctaagcgag caatgcaaca gccatcatcg tcattcacct    120
tgcctatcca tcatcctcgt cttcttctgt ctatccatgg cgatttggcg ttataaccac    180
ccccaccccc acccttctct ggctacgtcc tcgctttccc ttcctcccag ctgcctgccc    240
ccccttccct acccragcta cgcacgctac cagctgcccc ccatccatgc cgtccaggaa    300
gctggtggag gactccaaag ggatcgcatt gatctattct cacctgccgc ctgctgcatg    360
cgatgcgagt cgacgacaag atcagtgcaa tccctttgga attttccact cgcgccttca    420 ccccgccgc acgtgccaca cgcccctcca tcttccatgg attccatctc tcatcaggta    480
tctctctctc tatctgctct tgcaagctac ttccatggat ttgattttg ttaagttcgc    540 ctacttgctc tccacgtacg tactggctac atcgtttctg cgcaccacac acccaccagg    600
ccatgaggaa tcaatttgct catgggagca tgatgatgca gacaagtaca aacatagtat    660
ataataaaaa tagctgccga ttcattcttt cctttcgctc atcgttttcg tagttaattc    720
attcattggc atggttaagt atgtgtaaat acttacatgt agata                    765

<210> SEQ ID NO 87
```

<211> LENGTH: 756
<212> TYPE: DNA
<213> ORGANISM: Zea mays

<400> SEQUENCE: 87

```
ccgtgtcccc ttcggcccgg gatggcccac gtgcacgtcg aaagcgtgag agcgagagga      60
ggacgcctac ctaagcgagc aatgcaacag ccatcatcgt cattcacctt gcctatccat     120
catcctcgtc ttcttctgtc tatccatggc gatttggcgt tataaccacc cccacccca     180
cccttctctg gctacgtcct cgctttccct tcctcccagc tgcctgcccc ccttcccta     240
ccctagctac gcacgctacc agctgccccc catccatgcc gtccaggaag ctggtggagg     300
actccaaagg gatcgcattg atctattctc acctgccgcc tgctgcatgc gatgcgagtc     360
gacgacaaga tcagtgcaat ccctttggaa ttttccactc gcgccttcac ccccgccgca     420
cgtgccacac gcccctccat cttccatgga ttccatctct catcaggtat ctctctctct     480
atctgctctt gcaagctact tccatggatt tgattttgt taagttcgcc tacttgctct     540
ccacgtacgt actggctaca tcgttctgc gcaccacaca cccaccaggc catgaggaat     600
caatttgctc atgggagcat gatgatgcag acaagtacaa acatagtata taataaaaat     660
agctgccgat tcattctttc ctttcgctca tcgttttcgt agttaattca ttcattggca     720
tggttaagta tgtgtaaata cttacatgta gatata                               756
```

<210> SEQ ID NO 88
<211> LENGTH: 754
<212> TYPE: DNA
<213> ORGANISM: Zea mays

<400> SEQUENCE: 88

```
tcsgtgtccc cttcggcccg ggatggccca cgtgcacgtc gaaagcgtga gagcgagagg      60
aggacggcta cctaagcgag caatgcaaca gccatcatcg tcattcacct tgcctatcca     120
tcatcctcgt cttcttctgt ctatccatgg cgatttggcg ttataaccac ccccaccccc     180
acccttctct ggctacgtcc tcgctttccc ttcctcccag ctgcctgccc cccttccct     240
accctagcta cgcacgctac cagctgcccc ccatccatgc cgtccaggaa gctggtggag     300
gactccaaag ggatcgcatt gatctattct cacctgccgc ctgctgcatg cgatgcgagt     360
cgacgacaag atcagtgcaa tccctttgga attttccact cgcgccttca ccccgccgc     420
acgtgccaca cgcccctcca tcttccatgg attccatctc tcatcaggta tctctctctc     480
tatctgctct gcaagctac ttccatggat ttgattttg ttaagttcgc tacttgctc     540
tccacgtacg tactggctac atcgtttctg cgcaccacac acccaccagg ccatgaggaa     600
tcaatttgct catgggagca tgatgatgca gacaagtaca acatagtat ataataaaaa     660
tagctgccga ttcattcttt cctttcgctc atcgttttcg tagttaattc attcattggc     720
atggttaagt atgtgtaaat acttacatgt agwt                                 754
```

<210> SEQ ID NO 89
<211> LENGTH: 611
<212> TYPE: DNA
<213> ORGANISM: Zea mays

<400> SEQUENCE: 89

```
agccatcatc gtcgtcttct tctgtctatc catggcgatt ggcgttataa ccacccccca      60
cccccaccct tctctggcta cgtcctcgct ttccttcct cccagctgcc tgccccct     120
tccctaccct agctacgcac gctaccagct gccccccatc catgccgtcc aggaagctgg     180
```

```
tggaggactc caaagggatc gcattgatct attctcacct gccgcctgct gcatgcgatg     240
cgagtcgacg acaagatcag tgcaatccct ttggaatttt ccactcgcgc cttcaccccc     300
gccgcacgtg ccacacgccc ctccatcttc catggattcc atctctcatc aggtatctct     360
ctctctatct gctcttgcaa gctacttcca tggatttgat ttttgttaag ttcgcctact     420
tgctctccac gtacgtactg gctacatcgt ttctgcgcac cacacaccca ccaggccatg     480
aggaatcaat ttgctcatgg gagcatgatg atgcagacaa gtacaaacat agtatataat     540
aaaaatagct gccgattcat tctttccttt cgctcatcgt tttcgtagtt aattcattca     600
ttggcatggt t                                                          611

<210> SEQ ID NO 90
<211> LENGTH: 738
<212> TYPE: DNA
<213> ORGANISM: Zea mays

<400> SEQUENCE: 90
ccgtgtcccc ttcggcccgg gatggcccac gtgcacgtcg aaagcgtgag agcgagagga      60
ggaggaggag gcctacctaa gcagcaatg caacagccat catcgtcatt caccttgcct     120
atccatcatc gtcgtcttct tctgtctatc catggcgatt tggcgttata accacccac     180 cccacccttc cctggctacg acctcgcttt cccttcctcc cagctgcctg ccccccccc     240 ttccctaccc tagctacgca cgctaccagc tgcccccat ccatgccgtc caggaagctg     300
gtggaggact ccaaagggat cgcattgatc tattctcacc tgccgcctgc tgcatgcgat     360
gcgagtcgac gacaagatca gtgcaatccc tttggaattt tccactcgcg ccttcacccc     420
cgccgcacgt gccacacgcc cctccatctt ccatggattc catctctcat caggtatctc     480
tctccctata tatctgctct tgcaagctac ttccatggat ttgattttg ttaagttcgc     540 ctacttgctc tccacgtacg tactagctac atcgtttcca ccaggccatg aggagttatt     600
caatctacga gtctgctgcc tccttcaatt tgctcatggg agcatgatga tagatgcaga     660
caagtacaaa catagtatat aataaaaata gcwgccgatt mattcttycc tttcrctcat     720
cgttttcgta gttaattc                                                   738

<210> SEQ ID NO 91
<211> LENGTH: 565
<212> TYPE: DNA
<213> ORGANISM: Zea mays

<400> SEQUENCE: 91
ttcggcccgg gatggcccac gtgcacgtcg aaagcgtgag agcgagagga ggaggaggag      60
gcctacctaa gcagcaatg caacagccat catcgtcatt caccttgcct atccatcatc     120
gtcgtcttct tctgtctatc catggcgatt tggcgttata accacccac cccacccttc     180 cctggctacg acctcgcttt cccttcctcc cagctgcctg ccccccttc cctacctag     240 ctacgcacgc taccagctgc ccccatcca tgccgtccag gaagctggtg gaggactcca     300
aagggatcgc attgatctat tctcacctgc cgcctgctgc atgcgatgcg agtcgacgac     360
aagatcagtg caatccctt ggaattttcc actcgcgcct tcaccccgc cgcacgtgcc     420 acacgcccct ccatcttcca tggattccat ctctcatcag gtatctctct ccctatatat     480
ctgctcttgc aagctacttc catggattg attttgtta agttcgccta cttgctctcc     540
acgtacgtac tagctacatc gtttc                                           565
```

<210> SEQ ID NO 92
<211> LENGTH: 762
<212> TYPE: DNA
<213> ORGANISM: Zea mays

<400> SEQUENCE: 92

```
ttcggcccgg gatggcccac gtgcacgtcg aaagcgtgag agcgagagga ggacgcctac      60
ctaagcgagc aatgcaacag ccatcatcgt cattcacctt gcctatccat catcctcgtc     120
ttcttctgtc tatccatggc gatttggcgt tataaccacc cccaccccca cccttctctg     180
gctacgtcct cgctttccct tcctcccagc tgcctgcccc ccttccccta ccctagctac     240
gcacgctacc agctgccccc catccatgcc gtccaggaag ctggtggagg actccaaagg     300
gatcgcattg atctattctc acctgccgcc tgctgcatgc gatgcgagtc gacgacaaga     360
tcagtgcaat ccctttggaa ttttccactc gcgccttcac ccccgccgca cgtgccacac     420
gcccctccat cttccatgga ttccatctct catcaggtat ctctctctct ctatctgctc     480
ttgcaagcta cttccatgga tttgattttt gttaagttcg cctacttgct ctccacgtac     540
gtactagcta catcgtttcc accagcccat gaggagttat tcaatctacg agtctgctgc     600
ctccttcaat ttgctcatgg gagcatgatg atagatgcag acaagtacaa acatagtata     660
taataaaaat agctgccgat tcattcttyc ctttcgctca tcgttttcgt agttaattca     720
ttcattggca tggttaagta tgtgtaaata cttacatgta ga                        762
```

<210> SEQ ID NO 93
<211> LENGTH: 697
<212> TYPE: DNA
<213> ORGANISM: Zea mays

<400> SEQUENCE: 93

```
cgtgtcccct tcggcccggg atggcccacg tgcacgtcga aagcgtgaga gcgagaggag      60
gacgcctacc taagcgagca atgcaacagc catcatcgtc attcaccttg cctatccatc     120
atcctcgtct tcttctgtct atccatggcg atttggcgtt ataaccaccc caccccccac     180
ccttctctgg ctacgtcctc gctttccctt cctcccagct gcctgccccc cttccctac     240
cctagctacg cacgctacca gctgccccc atccatgccg tccaggaagc tggtggagga     300
ctccaaaggg atcgcattga tctattctca cctgccgcct gctgcatgcg atgcgagtcg     360
acgacaagat cagtgcaatc cctttggaat tttccactcg cgccttcacc cccgccccgc     420
ccctccatcc acgcataaat ccaattccaa atgcttcctt ccatggattc catctctcat     480
caggtatctc tctctctatc tgctcttgca agctacttcc atggatttga ttttgttaa     540
gttcgcctac ttgctctcca cgtacgtact agctacatcg tttccaccaa gccatgagga     600
attattcaat ctacgagtct gctgcctcct tcaatttgct catgggagca tgatgatgca     660
gacaagtaca aacatagtat ataataaaaa tagctgc                              697
```

<210> SEQ ID NO 94
<211> LENGTH: 756
<212> TYPE: DNA
<213> ORGANISM: Zea mays

<400> SEQUENCE: 94

```
cgtgtcccct tcggcccggg atggcccacg tgcacgtcga aagcgtgaga gcgagaggag      60
gacgcctacc taagcgagca atgcaacagc catcatcgtc attcaccttg cctatccatc     120
atcctcgtct tcttctgtct atccatggcg atttggcgtt ataaccaccc caccccccac     180
```

```
ccttctctgg ctacgtcctc gctttcccct cctcccagct gcctgccccc ccttccctac    240
cctagctacg cacgctacca gctgcccccc atccatgccg tccaggaagc tggtggagga    300
ctccaaaggg atcgcattga tctattctca cctgccgcct gctgcatgcg atgcgagtcg    360
acgacaagat cagtgcaatc cctttggaat tttccactcg cgccttcacc cccgccgcac    420
gtgccacacg cccctccatc ttccatggat tccatctctc atcaggtatc tctctctctc    480
tatctgctct tgcaagctac ttccatggat ttgattttg ttaagttcgc ctacttgctc    540
tccacgtacg tactagctac atcgtttcca ccagcccatg aggagttatt caatctacga    600
gtctgctgcc tccttcaatt tgctcatggg agcatgatga tagatgcaga caagtacaaa    660
catagtatat aataaaaata gctgccgatt cattctttcc tttcgctcat cgttttcgta    720
gttaattcat tcattggcat ggttaagtat gtgtaa                              756
```

<210> SEQ ID NO 95
<211> LENGTH: 782
<212> TYPE: DNA
<213> ORGANISM: Zea mays

<400> SEQUENCE: 95

```
csgtgtcccc ttcggcccgg gatggcccac gtgcacgtcg aaagcgtgag agcgagagga    60
ggaggaggag gcctacctaa gcgagcaatg caacagccat catcgtcatt caccttgcct    120
atccatcatc gtcgtcttct tctgtctatc catggcgatt tggcgttata accaccccac    180
cccacccttg cctggctacg acctcgcttt cccttcctcc cagctgcccc ccccccttc    240 cctaccctag ctacgcacgc taccagctgc ccccatcca tgccgtccag gaagctggtg    300
gaggactcca aagggatcgc attgatctat tctcacctgc cgcctgctgc atgcgatgcg    360
agtcgacgac aagatcagtg caatcccttt ggaatttttcc actcgcgcct tcaccccgc    420 cgcacgtgcc acacgcccct ccatcttcca tggattccat ctctcatcag gtatctctct    480
ccctatatat ctgctcttgc aagctacttc catggatttg attttgtta agttcgccta    540 cttgctctcc acgtacgtac tagctacatc gtttccacca ggccatgagg agttatccaa    600
cagacgagta ggatgctgcc tcctcaattt gctcatggga gcatgatgat gcagacaagt    660
acaaacatag tatataataa aaatagctgc cgattcattc tttcctttcg ctcatcgttt    720
tcgtagttaa ttcattcatt ggcatggtta agtatgtgta atacttaca tgtagatata    780 tc                                                                   782
```

<210> SEQ ID NO 96
<211> LENGTH: 565
<212> TYPE: DNA
<213> ORGANISM: Zea mays

<400> SEQUENCE: 96

```
ttcggcccgg gatggcccac gtgcacgtcg aaagcgtgag agcgagagga ggaggaggag    60
gcctacctaa gcgagcaatg caacagccat catcgtcatt caccttgcct atccatcatc    120
gtcgtcttct tctgtctatc catggcgatt tggcgttata accaccccac cccacccttc    180
cctggctacg acctcgcttt ccttcctcc cagctgcctg ccccccctc cctaccctag    240 ctacgcacgc taccagctgc ccccatccat gccgtccag gaagctggtg gaggactcca    300
aagggatcgc attgatctat tctcacctgc cgcctgctgc atgcgatgcg agtcgacgac    360
aagatcagtg caatcccttt ggaatttttcc actcgcgcct tcaccccgc cgcacgtgcc    420
```

```
acacgcccct ccatcttcca tggattccat ctctcatcag gtatctctct ccctatatat    480
ctgctcttgc aagctacttc catggatttg attttttgtta agttcgccta cttgctctcc    540
acgtacgtac tagctacatc gtttc                                           565

<210> SEQ ID NO 97
<211> LENGTH: 732
<212> TYPE: DNA
<213> ORGANISM: Zea mays

<400> SEQUENCE: 97
gtggtgggcc ctcsgtgtcc ccttcggccc gggatggccc acgtgcacgt cgaaagcgtg     60
agagcgagag gaggacgcct acctaagcga gcaatgcaac agccatcatc gtcattcacc    120
ttgcctatcc atcatcctcg tcttcttctg tctatccatg gcgatttggc gttataacca    180
cccccacccc caccccttctc tggctacgtc ctcgctttcc cttcctccca gctgcctgcc    240
cccccttccc tacctagct acgcacgcta ccagctgccc ccatccatg ccgtccagga      300 agctggtgga ggactccaaa gggatcgcat tgatctattc tcacctgccg cctgctgcat    360
gcgatgcgag tcgacgacaa gatcagtgca atccctttgg aattttccac tcgcgccttc    420 accccgccg cacgtgccac acgccctcc atcttccatg gattccatct ctcatcaggt      480
atctctctct ctatctgctc ttgcaagcta cttccatgga tttgattttt gttaagttcg    540
cctacttgct ctccacgtac gtactggcta catcgtttct cgcaccaca cacccaccag     600 gccatgagga atcaatttgc tcatgggagc atgatgawgc agacaagtac aaacatagta    660
tataataaaa atagctgccg attcattctt yccttttcgct catcgttttc gtagttaatt   720
cattcattgg ca                                                         732

<210> SEQ ID NO 98
<211> LENGTH: 761
<212> TYPE: DNA
<213> ORGANISM: Zea mays

<400> SEQUENCE: 98
cgtgtcccct tcggcccggg atggcccacg tgcacgtcga aagcgtgaga gcgagaggag     60
gacgcctacc taagcgagca atgcaacagc catcatcgtc attcaccttg cctatccatc    120
atcctcgtct tcttctgtct atccatggcg atttggcgtt ataaccaccc ccaccccac     180 ccttctctgg ctacgtcctc gctttccctt cctccagct gcctgccccc cccccctac      240 ccwagctacg cacgctacca gctgccccc atccatgccg tccaggaagc tggtggagga     300
ctccaaaggg atcgcattga tctattctca cctgccgcct gctgcatgcg atgcgagtcg    360
acgacaagat cagtgcaatc cctttggaat tttccactcg cgccttcacc ccgccgcac    420 gtgccacacg ccctccatc ttccatggat tccatctctc atcaggtatc tctctctctc    480
tatctgctct tgcaagctac ttccatggat ttgattttg ttaagttcg ctacttgctc    540 tccacgtacg tactagctac atcgtttcca ccagcccatg aggagttatt caatctacga    600
gtctgctgcc tccttcaatt tgctcatggg agcatgatga tagatgcaga caagtacaaa    660
catagtatat aataaaaata gctgccgatt cattctttcc tttcgctcat cgttttcgta   720
gttaattcat tcattggcat ggttaagtat gtgtaaatac t                       761

<210> SEQ ID NO 99
<211> LENGTH: 624
<212> TYPE: DNA
<213> ORGANISM: Zea mays
```

<400> SEQUENCE: 99

```
agccatcatc gtcgtcttct tctgtctatc catggcgatg tggcgttata accaccccca      60
cccccacccc cacycttctc tggctacgtc ctcgctttcc cttcctccca gctgcctgcc     120
cccccttccc tacccctagct acgcacgcta ccagctgccc cccatccatg ccgtccagga    180
agctggtgga ggactccaaa gggatcgcat tgatctattc tcacctgccg cctgctgcat    240
gcgatgcgag tcgacgacaa gatcagtgca atccctttgg aattttccac tcgcgccttc    300
accccgccg cacgtgccac acgcccctcc atcttccatg gattccatct ctcatcaggt    360
atctctctct ctctatctgc tcttgcaagc tacttccatg gatttgattt ttgttaagtt    420
cgcctacttg ctctccacgt acgtacwggc tacatcgttt ctgcgcacca cacacccacc    480
aggccatgag gaatcaatty sctcatggga gcatgatgat gcagacaagt acaaacatag    540
tatataataa aaatagctgc cgattcattc ttyccttcg ctcatcgttt tcgtagttaa    600
ttcattcatt ggcatggtta agta                                            624
```

<210> SEQ ID NO 100
<211> LENGTH: 745
<212> TYPE: DNA
<213> ORGANISM: Zea mays

<400> SEQUENCE: 100

```
agcatctccg tggtgggccc tccgtgtccc cttcggcccg ggatggccca cgtgcacgtc     60
gaaagcgtga gagcgagagg aggacgccta cctaagcgag caatgcaaca gccatcatcg    120
tcattcacct tgcctatcca tcatcctcgt cttcttctgt ctatccatgg cgatttggcg    180
ttataaccac ccccaccccc acccttctct ggctacgtcc tcgctttccc ttcctcccag    240
ctgcctgccc cccttccct accctagcta cgcacgctac cagctgcccc ccatccatgc    300
cgtccaggaa gctggtggag gactccaaag ggatcgcatt gatctattct cacctgccgc    360
ctgctgcatg cgatgcgagt cgacgacaag atcagtgcaa tccctttgga attttccact    420
cgcgccttca ccccgccgc acgtgccaca cgcccctcca tcttccatgg attccatctc    480
tcatcaggta tctctctctc tatctgctct tgcaagctac ttccatggat ttgatttttg    540
ttaagttcgc ctacttgctc tccacgtacg tactggctac atcgtttctg cgcaccacac    600
acccaccagg ccatgaggaa tcaatttgct catgggagca tgatgatgca gacaagtaca    660
aacatagtat ataataaaaa tagctgccga ttcattcttt cctttcgctc atcgttttsg    720
tagttaattc attcattggc atggt                                           745
```

<210> SEQ ID NO 101
<211> LENGTH: 744
<212> TYPE: DNA
<213> ORGANISM: Zea mays

<400> SEQUENCE: 101

```
tgtccccttc ggcccgggat ggcccacgtg cacgtcgaaa gcgtgagagc gagaggagga     60
ggaggaggcc tacctaagcg agcaatgcaa cagccatcat cgtcattcac cttgcctatc    120
catcatcgtc gtcttcttct gtctatccat ggcgatttgg cgttataacc accccaccc    180
acccttgcct ggctacgacc tcgctttccc ttcctcccag ctgcctgccc cccttccc    240
taccctagct acgcacgcta ccagctgccc cccatccatg ccgtccagga agctggtgga    300
ggactccaaa gggatcgcat tgatctattc tcacctgccg cctgctgcat gcgatgcgag    360
```

```
tcgacgacaa gatcagtgca atcccttcgg aattttccac tcgcgccttc acccccgccg    420
cacgtgccac acgcccctcc atcttccatg gattccatct ctcatcaggt atctctctcc    480
ctatatatct gctcttgcaa gctacttcca tggatttgat ttttgttaag ttcgcctact    540
tgctctccac gtacgtacta gctacatcgt ttccaccagg ccatgaggag ttattcaatc    600
tacgagtctg ctgcctcctt caatttgctc atgggagcat gatgatagat gcagacaagt    660
acaaacatag tatataataa aaatagctgc cgattcattc tttcctttcg ctcatcgttt    720
tcgtagttaa ttcattcatt ggca                                          744

<210> SEQ ID NO 102
<211> LENGTH: 757
<212> TYPE: DNA
<213> ORGANISM: Zea mays

<400> SEQUENCE: 102 cccttcggc ccgggatggc ccacgtgcac gtcgaaagcg tgagagcgag aggaggagga     60
ggaggcctac ctaagcgagc aatgcaacag ccatcatcgt cattcaccttg gcctatccat   120 catcctcgtc ttcttctgtc catccatggc gatttggcgt tataaccacc ccaccccacc   180
cttctctggc tacgacctcg ctttcccttc ctcccagctg cctgcccccc ctaccctacc   240
ctagctacgc acgctaccag ctgccccccca tccatgccgt ccaggaagct ggtggaggac   300
tccaaaggga tcgcattgat ctattctcac ctgccgcctg ctgcatgcga tgcgagtcga   360
cgacaagatc agtgcaatcc ctttggaatt ttccactcgc gccttcaccc ccgccgcacg   420
tgccacacgc ccctccatct tccatggatt ccatctctca tcaggtatct ctctctctct   480
ctatctgctc ttgcaagcta cttccatgga tttgattttt gttaagttcg cctacttgct   540
ctccacgtac gtactagcta catcgtttct gcgcaccaca cacccaccag gccatgagga   600
atcaatttgc tcatgggagc atgatgatgc agacaagtac aaacatagta tataataaaa   660
atagctgccg attaattctt cctttcgct catcgttttc gtagttaatt cattcattgg    720
catggttaag tatgtgtaaa tacttacatg tagatat                            757

<210> SEQ ID NO 103
<211> LENGTH: 764
<212> TYPE: DNA
<213> ORGANISM: Zea mays

<400> SEQUENCE: 103
cttcggcccg ggatggccca cgtgcacgtc gaaagcgtga gagcgagagg aggacgccta     60
cctaagcgag caatgcaaca gccatcatcg tcattcacct tgcctatcca tcatcctcgt    120
cttcttctgt ctatccatgg cgatttggcg ttataaccac ccccaccccc acccttctct    180
ggctacgtcc tcgctttccc ttcctcccag ctgcctgccc ccctccct accctagcta     240 cgcacgctac cagctgcccc catccatgc cgtccaggaa gctggtggag gactccaaag    300
ggatcgcatt gatctattct cacctgccgc ctgctgcatg cgatgcgagt cgacgacaag   360
atcagtgcaa tccctttgga attttccact cgcgccttca ccccgccgc acgtgccaca   420 cgcccctcca tcttccatgg attccatctc tcatcaggta tctctctctc tctatctgct   480
cttgcaagct acttccatgg atttgattt tgttaagttc gcctacttgc tctccacgta   540
cgtactagct acatcgtttc tgcgcaccac acacccaccag gccatgaggag              600 atcaatttg ctcatgggag catgatgata gatgcagaca agtacaaaca tagtatataa    660 tataaaaaatagc tgccgattca ttctttcctt tcgctcatcg ttttcgtagt taattcattc   720
```

```
attggcatgg ttaagtatgt gtaaatactt acatgtagat atat              764
```

<210> SEQ ID NO 104
<211> LENGTH: 697
<212> TYPE: DNA
<213> ORGANISM: Zea mays

<400> SEQUENCE: 104

```
ggaggacgcc tacctaagcg agcaatgcaa cagccatcat cgtcattcac cttgcctatc    60
catcatcctc gtcttcttct gtctatccat ggcgatttgg cgttataacc accccaccc   120
ccacccttct ctggctacgt cctcgctttc ccttcctccc agctgcctgc cccccttcc   180
ctaccctagc tacgcacgct accagctgcc ccccatccat gccgtccagg aagctggtgg   240
aggactccaa agggatcgca ttgatctatt ctcacctgcc gcctgctgca tgcgatgcga   300
gtcgacgaca agatcagtgc aatccctttg gaattttcca ctcgcgcctt caccccgcc   360
gcacgtgcca cacgccctc catcttccat ggattccatc tctcatcagg tatctctctc   420
tctatctgct cttgcaagct acttccatgg atttgatttt tgttaagttc gcctacttgc   480
tctccacgta cgtactggct acatcgtttc tgcgcaccac acacccacca ggccatgagg   540
aatcaatttg ctcatgggag catgatgatg cagacaagta caaacatagt atataataaa   600
aatagctgcc gattcattct tyccttcgc tcatcgtttt cgtagttaat tcattcattg   660
gcatggttaa gtatgtgtaa atacttacat gtagata                             697
```

<210> SEQ ID NO 105
<211> LENGTH: 669
<212> TYPE: DNA
<213> ORGANISM: Zea mays

<400> SEQUENCE: 105

```
gtcgaaagcg tgagagcgag aggaggacgc ctacctaagc gagcaatgca acagccatca    60
tcgtcattca ccttgcctat ccatcatcct cgtcttcttc tgtctatcca tggcgatttg   120
gcgttataac cacccccacc cccacccttc tctggctacg tcctcgcttt cccttcctcc   180
cagctgcctg ccccccttc cctacccag ctacgcacgc taccagctgc ccccatcca   240
tgccgtccag gaagctggtg gaggactcca aagggatcgc attgatctat tctcacctgc   300
cgcctgctgc atgcgatgcg agtcgacgac aagatcagtg caatccctt ggaattttcc   360
actcgcgcct tcaccccgc cccgccatgg attccatctc tcatcaggta tctctctctc   420
tctctatctg ctcttgcaag ctacttccat ggatttgatt ttgtaagt cgcctactt   480
gctctccacg tacgtactag ctacatcgtt tctgcgcacc acacacccac caggccatga   540
ggaatcaatt tgctcatggg agcatgatga tgcagacaag tacaaacata gtatataata   600
aaaatagctg ccgattaatt ctttcctttc gctcatcgtt ttcgtagtta attcattcat   660
tggcatggt                                                            669
```

<210> SEQ ID NO 106
<211> LENGTH: 707
<212> TYPE: DNA
<213> ORGANISM: Zea mays

<400> SEQUENCE: 106

```
ccgtgtcccc ttcggcccgg gatggccac gtgcacgtcg aaagcgtgag agcgagagga    60
ggacgcctac ctaagcgagc aatgcaacag ccatcatcgt cattcacctt gcctatccat   120
```

```
catcctcgtc ttcttctgtc tatccatggc gatttggcgt tataaccacc cccacccccca    180
cccttctctg ctacgtcct cgcttccct tcctcccagc tgcctgcccc cccttccta       240
ccctagctac gcacgctacc agctgccccc catccatgcc gtccaggaag ctggtggagg    300
actccaaagg gatcgcattg atctattctc acctgccgcc tgctgcatgc gatgcgagtc    360
gacgacaaga tcagtgcaat ccctttggaa ttttccactc gcgccttcac ccccgccccg    420
ccatggattc catctctcat caggtatctc tctctctctc tatctgctct tgcaagctac    480
ttccatggat ttgattttg ttaagttcgc ctacttgctc tccacgtacg tactagctac    540
atcgtttctg cgcaccacac acccaccagg ccatgaggaa tcaatttgct catgggagca    600
tgatgatgca gacaagtaca acatagtat ataataaaaa tagctgccga ttaattcttt    660
cctttcgctc atcgttttcg tagttaattc attcattggc atggtta                 707
```

<210> SEQ ID NO 107
<211> LENGTH: 697
<212> TYPE: DNA
<213> ORGANISM: Zea mays

<400> SEQUENCE: 107

```
tcccctccgg cccgggatgg cccacgtgca cgtcgaaagc gtgagagcga gaggaggacg     60
cctacctaag cgagcaatgc aacagccatc atcgtcattc accttgccta tccatcatcc    120
tcgtcttctt ctgtctatcc atggcgattt ggcgttataa ccacccccac ccccaccctt    180
ctctggctac gtcctcgctt tcccttcctc ccagctgcct gccccccctt cctaccccta    240
gctacgcacg ctaccagctg cccccatcc atgccgtcca ggaagctggt ggaggactcc    300
aaagggatcg cattgatcta ttctcacctg ccgcctgctg catgcgatgc gagtcgacga    360
caagatcagt gcaatcccctt tggaattttc cactcgcgcc ttcaccccg cccgccatg    420
gattccatct ctcatcaggt atctctctct ctctctatct gctcttgcaa gctacttcca    480
tggatttgat tttgttaag ttcgcctact tgctctccac gtacgtacta gctacatcgt    540
ttctgcgcac cacacaccca ccaggccatg aggaatcaat ttgctcatgg agcatgatg    600
atgcagacaa gtacaaacat agtatataat aaaaatagct gccgattaat tctttccttt    660
cgctcatcgt tttcgtagtt aattcattca ttggcat                            697
```

<210> SEQ ID NO 108
<211> LENGTH: 414
<212> TYPE: DNA
<213> ORGANISM: Zea mays

<400> SEQUENCE: 108

```
cccttcggcc cgggatggcc cacgtgcacg tcgaaagcgt gagagcgaga ggaggacgcc     60
tacctaagcg agcaatgcaa cagccatcat cgtcattcac cttgcctatc catcatcctc    120
gtcttcttct gtctatccat ggcgatttgg cgttataacc accccaccc ccacccttct    180
ctggctacgt cctcgctttc ccttcctccc agctgcctgc ccccccttcc taccctagc    240
tacgcacgct accagctgcc cccatccat gccgtccagg aagctggtgg aggactccaa    300
agggatcgca ttgatctatt ctcacctgcc gcctgctgca tgcgatgcga gtcgacgaca    360
agatcagtgc aatccctttg gaattttcca ctcgcgcctt caccccgcc ccgc         414
```

<210> SEQ ID NO 109
<211> LENGTH: 876
<212> TYPE: DNA
<213> ORGANISM: Zea mays

<400> SEQUENCE: 109

```
ctttaaatag tggcgcgtga cgctgactcc tcgcagaaga atcgtcagcg accccagagc    60
agggcaggga gtccttcctc ccaccagcta gctagcgata ctactatcca aagagaatat   120
ggagagattt ccctgagatt gcgcgaatca gtcactgcac gtacgtgtgg agcttttctg   180
ttttctcata acggcaaat gcagcagcag gaggctttgg gtattttat tttctctcaa    240
cgattggtaa tcagtatctg ggaaagctgt ggatgtggta gaccgacgtg cgttgagtcg   300
gcatcgtccg gttcatccta tgtattccct ttcctgctat aaataccggc cgggccgagg   360
gtgtcgaagc cgcagatcaa tgcatggccg cgcgccggcg ccgtaggga tggaggagga    420
ggaagaagag gcggccttgc atgagggcca gagctagcct gcctctggta gccaaggatg   480
acttgcctac atggtctcgc tagttccggt tgttgcatgc atgccactat gccagtcctg   540
ctgggtttgt gggcggtctc cttggctagc ctgagtggct cttgcctgtc atggaaggcc   600
tcttcttctc tgccacgtac tctcgcctag ctagtcgcct tatggtacgt accgtctgcc   660
tcagtggctc tggcctgtgc ttcgttgggt ttgccaggta agtatggctg tcgttcattg   720
ctgattcatc agctggctca tatatatgta atgctgcatg caacgctaat atcgttttct   780
taattatttt gttattacct gtgcgtgctt gcagattgtt ctgaattctg aaatgtatgg   840
gttggacatt catcatcttg taccgttgtg ctgcat                             876
```

<210> SEQ ID NO 110
<211> LENGTH: 764
<212> TYPE: DNA
<213> ORGANISM: Zea mays

<400> SEQUENCE: 110

```
gatccgattg tcctgcgtat ggctggcagc aggacggagg atctgaagat ctttgaatca    60
ccagtcggcc gatgctcgcg cgtgcctcga ttctttctc gaggctagct agctacctac   120
aggtgacgca tgcatgcata tatagttgca tctgcgtgtg ttagatgagc acttgtaaaa   180
gagatcatgt gatgagggggg gggggggggg gggagagaga gagagagagg aggaagacgc   240
ggccggacta tttagctatc cgtgtgtgat gaagggcagt agcagtatat gtgctgcttt   300
gatgaattcc atggttggat ggcatggagg gagcgatatt ggcgaggttc aatcagatga   360
tgtattttc ttatatataa atttgcatgc atgaaggtgt gaatccagtg tctgattgag    420
ccgcgccaat atcacttcct tccaccataa gtttacacac agagaggatt gcagcgagcg   480
cgtctacttc caaaggttag accactcgtt atttcctcat ttccaaatta cacttgtcta   540
ttatactccc tctgtgccat tatagtgttc gttttagctt ttctttgtcc atattaaaat   600
agatatcaat gaatatatat atatataata tttttggagc actagacttc taatgactac   660
acgaagccct gacccaacgg tgccatccgg ttcagccaca tcagattcgg ccggctataa   720
aaacactcac acgctaccag agattaggtt ttaacgacgg cgat                    764
```

<210> SEQ ID NO 111
<211> LENGTH: 864
<212> TYPE: DNA
<213> ORGANISM: Zea mays

<400> SEQUENCE: 111

```
gacctcacat gacgcttgtc gaccgcggga agcagcatct ccgtggtggg ccctccgtgt    60
cccccttcggc ccgggatggc ccacgtgcac gtcgaaagcg tgagagcgag aggaggacgc   120
```

-continued

```
ctacctaagc gagcaatgca acagccatca tcgtcattca ccttgcctat ccatcatcct    180
cgtcttcttc tgtctatcca tggcgatttg gcgttataac cacccccacc cccacccttc    240
tctggctacg tcctcgcttt cccttcctcc cagctgcctg cccccccttc cctaccctag    300
ctacgcacgc taccagctgc cccccatcca tgccgtccag gaagctggtg gaggactcca    360
aagggatcgc attgatctat tctcacctgc cgcctgctgc atgcgatgcg agtcgacgac    420
aagatcagtg caatcccttt ggaattttcc actcgcgcct tcaccccgc cgcacgtgcc     480 acacgcccct ccatcttcca tggattccat ctctcatcag gtatctctct ctctatctgc    540
tcttgcaagc tacttccatg gatttgattt ttgttaagtt cgcctacttg ctctccacgt    600
acgtactggc tacatcgttt ctgcgcacca cacacccacc aggccatgag gaatcaattt    660
gctcatggga gcatgatgat gcagacaagt acaaacatag tatataataa aaatagctgc    720
cgattcattc tttcctttcg ctcatcgttt tcgtagttaa ttcattcatt ggcatggtta    780
agtatgtgta aatacttaca tgtagatata tcagggtaaa ggtccagaca ggacccattt    840
aagaggattg aatatgcctg cagc                                          864
```